US009546368B2

(12) United States Patent
Bennett et al.

(10) Patent No.: US 9,546,368 B2
(45) Date of Patent: Jan. 17, 2017

(54) METHODS FOR MODULATING METASTASIS-ASSOCIATED-IN-LUNG-ADENOCARCINOMA-TRANSCRIPT-1 (MALAT-1) EXPRESSION

(71) Applicant: Ionis Pharmaceuticals, Inc., Carlsbad, CA (US)

(72) Inventors: C. Frank Bennett, Carlsbad, CA (US); Susan M. Freier, San Diego, CA (US); Eric G. Marcusson, San Francisco, CA (US); Ssucheng J. Hsu, Pinole, CA (US); Robert A. MacLeod, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/368,269

(22) PCT Filed: Dec. 21, 2012

(86) PCT No.: PCT/US2012/071371
§ 371 (c)(1),
(2) Date: Jun. 23, 2014

(87) PCT Pub. No.: WO2013/096837
PCT Pub. Date: Jun. 27, 2013

(65) Prior Publication Data
US 2014/0371296 A1   Dec. 18, 2014

Related U.S. Application Data

(60) Provisional application No. 61/579,343, filed on Dec. 22, 2011.

(51) Int. Cl.
*A61K 31/70* (2006.01)
*C07H 21/02* (2006.01)
*C07H 21/04* (2006.01)
*C12N 15/113* (2010.01)
*A61K 31/711* (2006.01)
*C12N 5/00* (2006.01)

(52) U.S. Cl.
CPC ......... *C12N 15/1136* (2013.01); *A61K 31/711* (2013.01); *C12N 15/113* (2013.01); *C12N 2310/11* (2013.01); *C12N 2310/113* (2013.01); *C12N 2310/315* (2013.01); *C12N 2310/3341* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS

| | | |
|---|---|---|
| 4,981,957 A | 1/1991 | Lebleu et al. |
| 5,034,506 A | 7/1991 | Summerton et al. |
| 5,118,800 A | 6/1992 | Smith et al. |
| 5,166,315 A | 11/1992 | Summerton et al. |
| 5,185,444 A | 2/1993 | Summerton et al. |
| 5,319,080 A | 6/1994 | Leumann |
| 5,359,044 A | 10/1994 | Cook et al. |
| 5,393,878 A | 2/1995 | Leumann |
| 5,446,137 A | 8/1995 | Maag et al. |
| 5,466,786 A | 11/1995 | Buhr et al. |
| 5,514,785 A | 5/1996 | Van Ness et al. |
| 5,519,134 A | 5/1996 | Acevedo et al. |
| 5,567,811 A | 10/1996 | Mistura et al. |
| 5,576,427 A | 11/1996 | Cook et al. |
| 5,591,722 A | 1/1997 | Montgomery et al. |
| 5,597,909 A | 1/1997 | Urdea et al. |
| 5,610,300 A | 3/1997 | Altmann et al. |
| 5,627,053 A | 5/1997 | Usman et al. |
| 5,639,873 A | 6/1997 | Barascut et al. |
| 5,646,265 A | 7/1997 | McGee |
| 5,670,633 A | 9/1997 | Cook et al. |
| 5,698,685 A | 12/1997 | Summerton et al. |
| 5,700,920 A | 12/1997 | Altmann et al. |
| 5,792,847 A | 8/1998 | Buhr et al. |
| 6,268,490 B1 | 7/2001 | Imanishi et al. |
| 6,525,191 B1 | 2/2003 | Ramasamy |
| 6,600,032 B1 | 7/2003 | Manoharan et al. |
| 6,670,461 B1 | 12/2003 | Nielsen et al. |
| 6,770,748 B2 | 8/2004 | Imanishi et al. |
| 6,794,499 B2 | 9/2004 | Wengel et al. |
| 7,034,133 B2 | 4/2006 | Wengel et al. |

(Continued)

FOREIGN PATENT DOCUMENTS

| | | |
|---|---|---|
| WO | WO 98/39352 | 9/1998 |
| WO | WO 99/14226 | 3/1999 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — Sean McGarry
(74) *Attorney, Agent, or Firm* — Knobbe, Martens, Olson & Bear, LLP

(57) ABSTRACT

The present embodiments provide compounds and methods for reducing expression of Metastasis-Associated-in-Lung-Adenocarcinoma-Transcript-1 (MALAT-1) RNA and/or protein in an animal. Such methods are useful for treating cancer, such as colon cancer, intestinal cancer, lung cancer (e.g. non-small cell lung cancer), liver cancer, and/or prostate cancer. In various aspects, the cancer is a primary cancer.

20 Claims, No Drawings

(56) References Cited

U.S. PATENT DOCUMENTS

| | | |
|---|---|---|
| 7,053,207 B2 | 5/2006 | Wengel |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 2004/0171570 A1 | 9/2004 | Allerson et al. |
| 2005/0130923 A1 | 6/2005 | Bhat et al. |
| 2008/0039618 A1 | 2/2008 | Allerson et al. |
| 2009/0012281 A1 | 1/2009 | Swayze et al. |
| 2009/0239816 A1 | 9/2009 | Rivory et al. |
| 2011/0301052 A1 | 12/2011 | McNeel et al. |
| 2012/0021515 A1 | 1/2012 | Swayze et al. |

FOREIGN PATENT DOCUMENTS

| | | |
|---|---|---|
| WO | WO 00/63364 | 10/2000 |
| WO | WO 01/49687 | 7/2001 |
| WO | WO 03/004602 | 1/2003 |
| WO | WO 2004/035765 | 10/2003 |
| WO | WO 2004/011624 | 2/2004 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |
| WO | WO 2011/139702 | 11/2011 |
| WO | WO 2012/012467 | 1/2012 |

OTHER PUBLICATIONS

Allshire, "Molecular biology. RNAi and heterochromatin—a hushed-up affair" Science (2002) 297(5588):1818-1819.

Altmann et al., "Second Generation Antisense Oligonucleotides Inhibition of PKC-α and c-raf Kinase Expression by Chimeric Oligonucleotides Incorporating 6"-Substituted Carbocyclic Nucleosides and 2"-O- Ethylene Glycol Substituted Ribonucleosides" Nuclewsodies Nucleotides. (1997) 16:917-926.

Altmann et al., "Second Generation of Antisense Oligonucleotides: From Nuclease Resistance to Biological Efficacy in Animals " Chimia. (1996) 50(4):168-176.

Altmann et al., "Second-generation antisense oligonucleotides: structure—activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2'-O-(2 Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Braasch et al., "Locked nucleic acid (LNA): fine-tuning the recognition of DNA and RNA" Chem. Biol. (2001) 8:1-7.

Braasch et al., "Novel antisense and peptide nucleic acid strategies for controlling gene expression" Biochemistry (2002) 41(14):4503-4510.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Pharmacokinetic Properties of Several Novel Oligonucleotide Analogs in mice" J. Pharmacol. Exp. Ther. (1996) 277(2):923-937.

Elayadi et al., "Application of PNA and LNA oligomers to chemotherapy" Curr. Opinion Invens. Drugs (2001) 2:558-561.

Freier et al., "The ups and downs of nucleic acid duplex stability: structure-stability studies on chemically-modified DNA:RNA duplexes" Nucleic Acids Research (1997) 25(22 :4429-4443.

Frieden et al., "Expanding the design horizon of antisense oligonucleotides with alpha-L-LNA" Nucleic Acids Research (2003) 31(21):6365-6372.

Gautschi et al., "Activity of a novel bcl-2/bcl-xLbispecific antisense oligonucleotide against tumors of diverse histologic origins" J. Natl. Cancer Inst. (2001) 93:463-471.

Gu et al., "Base pairing properties of D- and L-cyclohexene nucleic acids (CeNA)" Oligonucleotides (2003) 13(6):479-489.

Gu et al., "Enzymatic resolution and base pairing properties of D- and L-cyclohexenyl nucleic acids (CeNA)" Nucleosides Nucleotides Nucleic Acids (2005) 24(5-7):993-998.

Gu et al., "Synthesis of enantiomeric-pure cyclohexenyl nucleoside building blocks for oligonucleotide synthesis" Tetrahedron (2004) 60(9):2111-2123.

Hall et al., "Establishment and maintenance of a heterochromatin domain" Science (2002) 297(5590):2232-2237.

Horvath et al., "Stereoselective synthesis of (−)-ara-cyclohexenyl-adenine" Tetrahedron Letters (2007) 48:3621-3623.

Jenuwein, "Molecular biology. An RNA-guided pathway for the epigenome" Science (2002) 297(5590):2215-2218.

Jones et al., "RNA quantitation by fluorescence-based solution assay: RiboGreen reagent characterization" Analytical Biochemistry (1998) 265(2):368-374.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Letsinger et al., "Cholesteryl-conjugated oligonucleotides: Synthesis, properties, and activity as inhibitors of replication of human immunodeficiency virus in cell culture" PNAS (1989) 86:6553-6556.

Leumann et al., "DNA Analogues: From Supramolecular Principles to Biological Properties" Bioorganic & Medicinal Chemistry (2002) 10:841-854.

Maher et al., "Comparative hybrid arrest by tandem antisense oligodeoxyribonucleotides or oligodeoxyribonucleoside methylpbosphonates in a cell-free system" Nucl. Acid. Res. (1998) 16(8):3341-3358.

Manoharan et al., "Chemical Modifications to Improve Uptake and Bioavailability of Antisense Oligonucleotides" Arm. N.Y. Acad. Sci. (1992) 660: 306-309.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Martin, "New acces to 2'-O-alkylated ribonucleosides and properties of 2'-O-alkylated oligoribonucleotides" Helv. Chim. Acta. (1995) 78:486-504.

Mishra et al., "Improved leishmanicidal effect of phosphorotioate antisense oligonucleotides by LDL-mediated delivery" Biochim. Biophys. Acta (1995) 1264:229-237.

Moolenbeek et al., "The "Swiss roll": a simple technique for histological studies of the rodent intestine" Lab Anim (1981) 15(1):57-59.

(56) References Cited

OTHER PUBLICATIONS

Moser et al., "ApcMin, a mutation in the murine Apc gene, predisposes to mammary carcinomas and focal alveolar hyperplasias" Proc. Natl. Acad. Sci. (1993) 90(19):8977-8981.

Nauwelaerts et al., "Cyclohexenyl nucleic acids: conformationally flexible oligonucleotides" Nucleic Acids Res. (2005) 33(8):2452-2463.

Nauwelaerts et al., "Structural characterization and biological evaluation of small interfering RNAs containing cyclohexenyl nucleosides" J. Am. Chem. Soc. (2007) 129(30):9340-9348.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3:239-243.

Pal-Bhadra et al., "Heterochromatic silencing and HP1 localization in Drosophila are dependent on the RNAi machinery" Science (2004) 303(5658):669-672.

Park et al., "Diethylnitrosamine (DEN) induces irreversible hepatocellular carcinogenesis through overexpression of G1/S-phase regulatory proteins in rat" Toxicol. Lett. (2009) 191:321-326.

Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.

Robeyns et al., "Structure of the fully modified left-handed cyclohexene nucleic acid sequence GTGTACAC" J. Am. Chem. Soc. (2008) 130(6):1979-1984.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Shea et al., "Synthesis, hybridization properties and antiviral activity of lipid-oligodeoxynucleotide conjugates" Nucl. Acids Res. (1990) 18(13):3777-3783.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Smith et al., "Comparison of biosequences" Adv. Appl. Math. (1981) 2(4):482-489.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Tripathi et al., "The nuclear-retained noncoding RNA MALAT1 regulates alternative splicing by modulating SR splicing factor phosphorylation" Mol. Cell (2010) 39(6):925-938.

Verbeure et al., "RNase H mediated cleavage of RNA by cyclohexene nucleic acid (CeNA)" Nucleic Acids Res. (2001) 29(24):4941-4947.

Verdel et al., "RNAi-mediated targeting of heterochromatin by the RITS complex" Science (2004) 303(5668):672-676.

Volpe et al., "Regulation of heterochromatic silencing and histone H3 lysine-9 methylation by RNAi" Science (2002) 297(5588):1833:1837.

Wahlestedt et al., "Potent and nontoxic antisense oligonucleotide containing locked nucleic acids" Proc. Natl. Acad. Sci. USA (2000) 97: 5633-5638.

Wang et al., "A straightforward stereoselective synthesis of D- and L-5-hydroxy-4-hydroxymethyl-2-cyclohexenylguanine" J. Org. Chem. (2001) 66(25):8478-8482.

Wang et al., "Cyclohexene nucleic acids (CeNA) form stable duplexes with RNA and induce RNase H activity" Nucleosides Nucleotides Nucleic Acids (2001) 20(4-7):785-788.

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.

Wang et al., "Stereocontrolled synthesis of ara-type cyclohexenyl nucleosides" J. Org. Chem. (2003) 68(11):4499-4505.

Woolf et al., "Specificity of antisense oligonucleotides in vivo" Proc. Natl. Acad. Sci. (1992) 89(16):7305-7309.

Yao et al., "A novel orthotopic tumor model to study growth factors and oncogenes in hepatocarcinogenesis" Clin. Cancer. Res. (2003) 9(7):2719-2726.

Zhang et al., "PowerBLAST: A New Network BLAST Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Guo et al., "Inhibition of metastasis-associated lung adenocarcinoma transcript 1 in CaSki human cervical cancer cells suppresses cell proliferation and invasion" Acta Biochimica et Biophysica Sinica (2010) 42(3): 224-229.

Lai et al., "Long non-coding RNA MALAT-1 overexpression predicts tumor recurrence of hepatocellular carcinoma after liver transplantation." Med. Oncol. (2012) 29(3): 1810-1816.

Schmidt et al., "The long non-coding MALAT-1 RNA indicates a poor prognosis in Non-small Cell Lung Cancer and induces migration and tumor growth" Journal of Thoracic Oncology (2011) 6(12): 1984-1992.

Tano et al., "MALAT-1 enhances cell motility of lung adenocarcinoma cells by influencing the expression of motility-related genes" FEBS Letters (2010) 584(22): 4575-4580.

International Search Report for application PCT/US12/71371 dated Apr. 2, 2013.

Feng et al., "Expression of long non-coding ribonucleic acid metastasis-associated lung adenocarcinoma transcript-1 is correlated with progress and apoptosis of laryngeal squamous cell carcinoma" Head Neck Oncol. (2012) 4:46.

Ying et al., "Uprgulated MALAT-1 contributes to bladder cancer cell migration by inducing epithelial-tomesenchymal transition." Mol. Biosyst. (2012) 8(9):2289-94.

SEQUENCE LISTING

<160> NUMBER OF SEQ ID NOS: 29

<210> SEQ ID NO 1
<211> LENGTH: 8708
<212> TYPE: DNA
<213> ORGANISM: Homo sapiens

<400> SEQUENCE: 1

```
gtaaaggact ggggccccgc aactggcctc tcctgccctc ttaagcgcag cgccatttta      60
gcaacgcaga agcccggcgc cgggaagcct cagctcgcct gaaggcaggt cccctctgac     120
gcctccggga gcccaggttt cccagagtcc ttgggacgca gcgacgagtt gtgctgctat     180
cttagctgtc cttataggct ggccattcca ggtggtggta tttagataaa accactcaaa     240
ctctgcagtt tggtcttggg gtttggagga aagcttttat ttttcttcct gctccggttc     300
agaaggtctg aagctcatac ctaaccaggc ataacacaga atctgcaaaa caaaaacccc     360
taaaaaagca gacccagagc agtgtaaaca cttctgggtg tgtccctgac tggctgccca     420
aggtctctgt gtcttcggag acaaagccat tcgcttagtt ggtctacttt aaaaggccac     480
ttgaactcgc tttccatggc gatttgcctt gtgagcactt tcaggagagc ctggaagctg     540
aaaaacggta gaaaaatttc cgtgcgggcc gtgggggggct ggcggcaact ggggggccgc     600
agatcagagt gggccactgg cagccaacgg cccccgggc tcaggcgggg agcagctctg     660
tggtgtggga ttgaggcgtt ttccaagagt gggttttcac gtttctaaga tttcccaagc     720
agacagcccg tgctgctccg atttctcgaa caaaaaagca aaacgtgtgg ctgtcttggg     780
agcaagtcgc aggactgcaa gcagttgggg gagaaagtcc gccattttgc cacttctcaa     840
ccgtccctgc aaggctgggg ctcagttgcg taatggaaag taaagccctg aactatcaca     900 cttaatctt ccttcaaaag gtggtaaact atacctactg tccctcaaga gaacacaaga     960
agtgctttaa gaggtatttt aaaagttccg ggggttttgt gaggtgtttg atgacccgtt    1020
taaaatatga tttccatgtt tcttttgtct aaagtttgca gctcaaatct ttccacacgc    1080
tagtaattta agtatttctg catgtgtagt ttgcattcaa gttccataag ctgttaagaa    1140
aaatctagaa aagtaaaact agaacctatt tttaaccgaa gaactacttt ttgcctccct    1200
cacaaaggcg gcggaaggtg atcgaattcc ggtgatgcga gttgttctcc gtctataaat    1260
acgcctcgcc cgagctgtgc ggtaggcatt gaggcagcca gcgcaggggc ttctgctgag    1320
ggggcaggcg gagcttgagg aaaccgcaga taagtttttt tctctttgaa agatagagat    1380
taatacaact acttaaaaaa tatagtcaat aggttactaa gatattgctt agcgttaagt    1440
ttttaacgta attttaatag cttaagattt taagagaaaa tatgaagact tagaagagta    1500
gcatgaggaa ggaaaagata aaaggtttct aaaacatgac ggaggttgag atgaagcttc    1560
ttcatggagt aaaaaatgta tttaaaagaa aattgagaga aaggactaca gagcccgaa    1620 ttaataccaa tagaagggca atgcttttag attaaaatga aggtgactta aacagcttaa    1680
```

```
agtttagttt aaaagttgta ggtgattaaa ataatttgaa ggcgatcttt taaaaagaga    1740
ttaaaccgaa ggtgattaaa agaccttgaa atccatgacg cagggagaat tgcgtcattt    1800
aaagcctagt taacgcattt actaaacgca gacgaaaatg gaaagattaa ttgggagtgg    1860
taggatgaaa caatttggag aagatagaag tttgaagtgg aaaactggaa gacagaagta    1920
cgggaaggcg aagaaaagaa tagagaagat agggaaatta gaagataaaa acatactttt    1980
agaagaaaaa agataaattt aaacctgaaa agtaggaagc agaagaaaaa agacaagcta    2040
ggaaacaaaa agctaagggc aaaatgtaca aacttagaag aaaattggaa gatagaaaca    2100
agatagaaaa tgaaaatatt gtcaagagtt tcagatagaa aatgaaaaac aagctaagac    2160
aagtattgga gaagtataga agatagaaaa atataaagcc aaaaattgga taaaatagca    2220
ctgaaaaaat gaggaaatta ttggtaacca atttatttta aaagcccatc aatttaattt    2280
ctggtggtgc agaagttaga aggtaaagct tgagaagatg agggtgttta cgtagaccag    2340
aaccaattta gaagaatact tgaagctaga aggggaagtt ggttaaaaat cacatcaaaa    2400
agctactaaa aggactggtg taatttaaaa aaaactaagg cagaaggctt ttggaagagt    2460
tagaagaatt tggaaggcct taaatatagt agcttagttt gaaaaatgtg aaggactttc    2520
gtaacggaag taattcaaga tcaagagtaa ttaccaactt aatgttttg cattggactt    2580 tgagttaaga ttattttta aatcctgagg actagcatta attgacagct gacccaggtg    2640
ctacacagaa gtggattcag tgaatctagg aagacagcag cagacaggat tccaggaacc    2700
agtgtttgat gaagctagga ctgaggagca agcgagcaag cagcagttcg tggtgaagat    2760
aggaaaagag tccaggagcc agtgcgattt ggtgaaggaa gctaggaaga aggaaggagc    2820
gctaacgatt tggtggtgaa gctaggaaaa aggattccag gaaggagcga gtgcaatttg    2880
gtgatgaagg tagcaggcgg cttggcttgg caaccacacg gaggaggcga gcaggcgttg    2940
tgcgtagagg atcctagacc agcatgccag tgtgccaagg ccacagggaa agcgagtggt    3000
tggtaaaaat ccgtgaggtc ggcaatatgt tgttttctg gaacttactt atggtaacct    3060
tttatttatt ttctaatata atgggggagt ttcgtactga ggtgtaaagg gatttatatg    3120
gggacgtagc ccgatttccg ggtgttgtag gtttctcttt ttcaggctta tactcatgaa    3180
tcttgtctga agcttttgag ggcagactgc caagtcctgg agaaatagta gatggcaagt    3240
ttgtgggttt ttttttttta cacgaatttg aggaaaacca aatgaatttg atagccaaat    3300
tgagacaatt tcagcaaatc tgtaagcagt ttgtatgttt agttggggta atgaagtatt    3360
tcagttttgt gaatagatga cctgttttta cttcctcacc ctgaattcgt tttgtaaatg    3420
tagagtttgg atgtgtaact gaggcggggg ggagttttca gtattttttt ttgtgggggt    3480
gggggcaaaa tatgttttca gttctttttc ccttaggtct gtctagaatc ctaaaggcaa    3540
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt ttcccccac cccttaatc agactttaaa    3720 agtgcttaac cccttaaact tgttatttt tacttgaagc attttgggat ggtcttaaca    3780
gggaagagag agggtggggg agaaaatgtt tttttctaag attttccaca gatgctatag    3840
tactattgac aaactggggtt agagaaggag tgtaccgctg tgctgttggc acgaacacct    3900
tcagggactg gagctgcttt tatccttgga agagtattcc cagttgaagc tgaaaagtac    3960
agcacagtgc agctttggtt catattcagt catctcagga gaacttcaga agagcttgag    4020
taggccaaat gttgaagtta agttttccaa taatgtgact tcttaaaagt tttattaaag    4080
```

```
gggaggggca aatattggca attagttggc agtggcctgt tacgttggg attggtgggg    4140
tgggtttagg taattgttta gtttatgatt gcagataaac tcatgccaga gaacttaaag    4200
tcttagaatg gaaaagtaa agaaatatca acttccaagt tggcaagtaa ctcccaatga    4260
tttagttttt ttcccccag tttgaattgg gaagctgggg gaagttaaat atgagccact    4320
gggtgtacca gtgcattaat ttgggcaagg aaagtgtcat aatttgatac tgtatctgtt    4380
ttccttcaaa gtatagagct tttggggaag gaaagtattg aactgggggt tggtctggcc    4440
tactgggctg acattaacta caattatggg aaatgcaaaa gttgtttgga tatggtagtg    4500
tgtggttctc ttttggaatt tttttcaggt gatttaataa taatttaaaa ctactataga    4560
aactgcagag caaaggaagt ggcttaatga tcctgaaggg atttcttctg atggtagctt    4620
ttgtattatc aagtaagatt ctattttcag ttgtgtgtaa gcaagttttt ttttagtgta    4680
ggagaaatac ttttccattg tttaactgca aaacaagatg ttaaggtatg cttcaaaaat    4740
tttgtaaatt gttatttta aacttatctg tttgtaaatt gtaactgatt aagaattgtg    4800
atagttcagc ttgaatgtct cttagagggt gggcttttgt tgatgaggga ggggaaactt    4860
ttttttttc tatagacttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaattt taagcaaatg aaagctacca atttaaagtt    5100
acggaatcta ccatttaaa gttaattgct tgtcaagcta taaccacaaa aataatgaat    5160
tgatgagaaa tacaatgaag aggcaatgtc catctcaaaa tactgctttt acaaaagcag    5220
aataaaagcg aaagaaatg aaaatgttac actacattaa tcctggaata aaagaagccg    5280
aaataaatga gagatgagtt gggatcaagt ggattgagga ggctgtgctg tgtgccaatg    5340
tttcgtttgc ctcagacagg tatctcttcg ttatcagaag agttgcttca tttcatctgg    5400
gagcagaaaa cagcaggcag ctgttaacag ataagtttaa cttgcatctg cagtattgca    5460
tgttagggat aagtgcttat ttttaagagc tgtggagttc ttaaatatca accatggcac    5520
tttctcctga ccccttccct aggggatttc aggattgaga aattttttcca tcgagccttt    5580
ttaaaattgt aggacttgtt cctgtgggct tcagtgatgg gatagtacac ttcactcaga    5640
ggcatttgca tctttaaata atttcttaaa agcctctaaa gtgatcagtg ccttgatgcc    5700
aactaaggaa atttgtttag cattgaatct ctgaaggctc tatgaaagga atagcatgat    5760
gtgctgttag aatcagatgt tactgctaaa atttacatgt tgtgatgtaa attgtgtaga    5820
aaaccattaa atcattcaaa ataataaact attttttatta gagaatgtat acttttagaa    5880
agctgtctcc ttatttaaat aaaatagtgt ttgtctgtag ttcagtgttg gggcaatctt    5940
gggggggatt cttctctaat cttttcagaaa cttttgtctgc gaacactctt taatggacca    6000
gatcaggatt tgagcggaag aacgaatgta actttaaggc aggaaagaca aattttattc    6060
ttcataaagt gatgagcata taataattcc aggcacatgg caatagaggc cctctaaata    6120
aggaataaat aacctcttag acaggtggga gattatgatc agagtaaaag gtaattacac    6180
atttatttc cagaaagtca ggggtctata aattgacagt gattagagta atactttttc    6240
acatttccaa agtttgcatg ttaactttaa atgcttacaa tcttagagtg gtaggcaatg    6300
ttttacacta ttgaccttat ataggaagg gaggggtgc ctgtgggtt ttaaagaatt    6360
ttcctttgca gaggcatttc atccttcatg aagccattca ggattttgaa ttgcatatga    6420
```

-continued

```
gtgcttggct cttccttctg ttctagtgag tgtatgagac cttgcagtga gtttatcagc   6480
atactcaaaa tttttttcct ggaatttgga gggatgggag gagggggtgg ggcttacttg   6540
ttgtagcttt tttttttttt acagacttca cagagaatgc agttgtcttg acttcaggtc   6600
tgtctgttct gttggcaagt aaatgcagta ctgttctgat cccgctgcta ttagaatgca   6660
ttgtgaaacg actggagtat gattaaaagt tgtgttcccc aatgcttgga gtagtgattg   6720
ttgaaggaaa aaatccagct gagtgataaa ggctgagtgt tgaggaaatt tctgcagttt   6780
taagcagtcg tatttgtgat tgaagctgag tacattttgc tggtgtattt ttaggtaaaa   6840
tgctttttgt tcatttctgg tggtgggagg ggactgaagc ctttagtctt ttccagatgc   6900
aaccttaaaa tcagtgacaa gaaacattcc aaacaagcaa cagtcttcaa gaaattaaac   6960
tggcaagtgg aaatgtttaa acagttcagt gatctttagt gcattgttta tgtgtgggtt   7020
tctctctccc ctcccttggt cttaattctt acatgcagga acactcagca gacacacgta   7080
tgcgaagggc cagagaagcc agacccagta agaaaaaata gcctatttac tttaaataaa   7140
ccaaacattc cattttaaat gtggggattg ggaaccacta gttctttcag atggtattct   7200
tcagactata gaaggagctt ccagttgaat tcaccagtgg acaaaatgag gaaaacaggt   7260
gaacaagctt tttctgtatt tacatacaaa gtcagatcag ttatgggaca atagtattga   7320
atagatttca gctttatgct ggagtaactg gcatgtgagc aaactgtgtt ggcgtggggg   7380
tggaggggtg aggtgggcgc taagcctttt tttaagattt ttcaggtacc cctcactaaa   7440
ggcaccgaag gcttaaagta ggacaaccat ggagccttcc tgtggcagga gagacaacaa   7500
agcgctatta tcctaaggtc aagagaagtg tcagcctcac ctgattttta ttagtaatga   7560
ggacttgcct caactccctc tttctggagt gaagcatccg aaggaatgct tgaagtaccc   7620
ctgggcttct cttaacattt aagcaagctg tttttatagc agctcttaat aataaagccc   7680
aaatctcaag cggtgcttga aggggaggga aagggggaaa gcgggcaacc acttttccct   7740
agcttttcca gaagcctgtt aaaagcaagg tctccccaca agcaacttct ctgccacatc   7800
gccaccccgt gccttttgat ctagcacaga cccttcaccc ctcacctcga tgcagccagt   7860
agcttggatc cttgtgggca tgatccataa tcggtttcaa ggtaacgatg gtgtcgaggt   7920
ctttggtggg ttgaactatg ttagaaaagg ccattaattt gcctgcaaat tgttaacaga   7980
agggtattaa aaccacagct aagtagctct attataatac ttatccagtg actaaaacca   8040
acttaaacca gtaagtggag aaataacatg ttcaagaact gtaatgctgg gtgggaacat   8100
gtaacttgta gactggagaa gataggcatt tgagtggctg agagggcttt tgggtgggaa   8160
tgcaaaaatt ctctgctaag actttttcag gtgaacataa cagacttggc caagctagca   8220
tcttagcgga agctgatctc caatgctctt cagtagggtc atgaaggttt ttcttttcct   8280
gagaaaacaa cacgtattgt tttctcaggt tttgcttttt ggcctttttc tagcttaaaa   8340
aaaaaaaaag caaaagatgc tggtggttgg cactcctggt ttccaggacg gggttcaaat   8400
ccctgcggcg tctttgcttt gactactaat ctgtcttcag gactctttct gtatttctcc   8460
ttttctctgc aggtgctagt tcttggagtt ttggggaggt gggaggtaac agcacaatat   8520
ctttgaacta tatacatcct tgatgtataa tttgtcagga gcttgacttg attgtatatt   8580
catatttaca cgagaaccta atataactgc cttgtctttt tcaggtaata gcctgcagct   8640
ggtgttttga gaagccctac tgctgaaaac ttaacaattt tgtgtaataa aaatggagaa   8700
gctctaaa                                                            8708
```

<210> SEQ ID NO 2
<211> LENGTH: 8110
<212> TYPE: DNA
<213> ORGANISM: Homo sapiens

<400> SEQUENCE: 2

```
gatcagagtg ggccactgcc agccaacggc ccccggggct caggcgggga gcagctctgt      60
ggtgtgggat tgaggcgttt tccaagagtg ggttttcacg tttctaagat ttcccaagca     120
gacagcccgt gctgctccga tttctcgaac aaaaaagcaa aacgtgtggc tgtcttggga     180
gcaagtcgca ggactgcaag cagttggggg agaaagtccg ccattttgcc acttctcaac     240
cgtccctgca aggctgggc tcagttgcgt aatggaaagt aaagccctga actatcacac      300
tttaatcttc cttcaaaagg tggtaaacta tacctactgt ccctcaagag aacacaagaa     360
gtgctttaag aggcggcgga aggtgatcga attccggtga tgcgagttgt tctccgtcta     420
taaatacgcc tcgcccgagc tgtgcggtag gcattgaggc agccagcgca ggggcttctg     480 ctgaggggc aggcggagct tgaggaaacc gcagataagt ttttttctct ttgaaagata      540
gagattaata caactactta aaaaatatag tcaataggtt actaagatat tgcttagcgt     600
taagttttta acgtaatttt aatagcttaa gattttaaga gaaatatga agacttagaa      660 gagtagcatg aggaaggaaa agataaaagg tttctaaaac atgacggagg ttgagatgaa     720
gcttcttcat ggagtaaaaa atgtatttaa aagaaaattg agagaaagga ctacagagcc     780
ccgaattaat accaatagaa gggcaatgct tttagattaa aatgaaggtg acttaaacag     840
cttaaagttt agtttaaaag ttgtaggtga ttaaaataat ttgaaggcga tcttttaaaa     900
agagattaaa ccgaaggtga ttaaaagacc ttgaaatcca tgacgcaggg agaattgcgt     960
catttaaagc ctagttaacg catttactaa acgcagacga aaatggaaag attaattggg    1020
agtggtagga tgaaacaatt tggagaagat agaagtttga agtggaaaac tggaagacag    1080
aagtacggga aggcgaagaa aagaatagag aagataggga aattagaaga taaaaacata    1140
cttttagaag aaaaaagata aatttaaacc tgaaaagtag gaagcagaag agaaaagaca    1200
agctaggaaa caaaaagcta agggcaaaat gtacaaactt agaagaaaat tggaagatag    1260
aaacaagata gaaaatgaaa atattgtcaa gagtttcaga tagaaaatga aaaacaagct    1320
aagacaagta ttggagaagt atagaagata gaaaatatata aagccaaaaa ttggataaaa    1380
tagcactgaa aaaatgagga aattattggt aaccaattta ttttaaaagc ccatcaattt    1440
aatttctggt ggtgcagaag ttagaaggta aagcttgaga agatgagggt gtttacgtag    1500
accagaacca atttagaaga atacttgaag ctagaagggg aagttggtta aaaatcacat    1560
caaaaagcta ctaaaaggac tggtgtaatt taaaaaaac taaggcagaa ggcttttgga    1620
agagttagaa gaatttggaa ggccttaaat atagtagctt agtttgaaaa atgtgaagga    1680
ctttcgtaac ggaagtaatt caagatcaag agtaattacc aacttaatgt ttttgcattg    1740
gactttgagt taagattatt ttttaaatcc tgaggactag cattaattga cagctgaccc    1800
aggtgctaca cagaagtgga ttcagtgaat ctaggaagac agcagcagac aggattccag    1860
gaaccagtgt ttgatgaagc taggactgag gagcaagcga gcaagcagca gttcgtggtg    1920
aagataggaa aagagtccag gagccagtgc gatttggtga aggaagctag gaagaaggaa    1980
ggagcgctaa cgatttggtg gtgaagctag gaaaaaggat tccaggaagg agcgagtgca    2040
atttggtgat gaaggtagca ggcggcttgg cttggcaacc acacggagga ggcgagcagg    2100
cgttgtgcgt agaggatcct agaccagcat gccagtgtgc caaggccaca gggaaagcga    2160
```

-continued

```
gtggttggta aaaatccgtg aggtcggcaa tatgttgttt ttctggaact tacttatggt      2220 aacctttat ttattttcta atataatggg ggagtttcgt actgaggtgt aaagggattt      2280
atatggggac gtaggccgat ttccgggtgt tgtaggtttc tcttttcag gcttatactc      2340 atgaatcttg tctgaagctt ttgagggcag actgccaagt cctggagaaa tagtagatgg      2400
caagtttgtg ggtttttttt ttttacacga atttgaggaa aaccaaatga atttgatagc      2460
caaattgaga caatttcagc aaatctgtaa gcagtttgta tgtttagttg gggtaatgaa      2520
gtatttcagt tttgtgaata atgaccctgt ttttacttcc tcaccctgaa ttcgttttgt      2580
aaatgtagag tttggatgtg taactgaggc ggggggagt tttcagtatt ttttttgtg       2640 ggggtggggg caaaatatgt tttcagttct tttccctta ggtctgtcta gaatcctaaa      2700
ggcaaatgac tcaaggtgta acagaaaaca agaaaatcca atatcaggat aatcagacca      2760
ccacaggttt acagttata gaaactagag cagttctcac gttgaggtct gtggaagaga      2820
tgtccattgg agaaatggct ggtagttact ctttttcc cccacccct taatcagact       2880 ttaaaagtgc ttaacccctt aaacttgtta ttttttactt gaagcatttt gggatggtct     2940
taacagggaa gagagagggt ggggagaaa atgttttttt ctaagatttt ccacagatgc      3000
tatagtacta ttgacaaact gggttagaga aggagtgtac cgctgtgctg ttggcacgaa      3060 cacctttcagg gactggagct gcttttatcc ttggaagagt attcccagtt gaagctgaaa    3120
agtacagcac agtgcagctt tggttcatat tcagtcatct caggagaact tcagaagagc     3180
ttgagtaggc caaatgttga agttaagttt tccaataatg tgacttctta aaagttttat     3240
taaaggggag gggcaaatat tggcaattag ttggcagtgg cgtgttacgg tgggattggt     3300
ggggtgggtt taggtaattg tttagtttat gattgcagat aaactcatgc cagagaactt     3360
aaagtcttag aatggaaaaa gtaaagaaat atcaacttcc aagttggcaa gtaactccca    3420
atgatttagt ttttttcccc ccagtttgaa ttgggaagct gggggaagtt aaatatgagc     3480
cactgggtgt accagtgcat taatttgggc aaggaaagtg tcataatttg atactgtatc    3540
tgttttcctt caaagtatag agcttttggg gaaggaaagt attgaactgg gggttggtct    3600
ggcctactgg gctgacatta actacaatta tgggaaatgc aaaagttgtt tggatatggt    3660
agtgtgtggt tctcttttgg aatttttttc aggtgattta ataataattt aaaactacta    3720
tagaaactgc agagcaaagg aagtggctta atgatcctga agggattct tctgatggta     3780 gcttttgtat tatcaaactt ttttcagata acatcttctg agtcataacc agcctggcag    3840
tatgatggcc tagatgcaga gaaaacagct ccttggtgaa ttgataagta aaggcagaaa    3900
agattatatg tcatacctcc attgggggaat aagcataacc ctgagattct tactactgat    3960
gagaacatta tctgcatatg ccaaaaaatt ttaagcaaat gaaagctacc aatttaaagt    4020
tacggaatct accatttaa agttaattgc ttgtcaagct ataaccacaa aataatgaa      4080 ttgatgagaa atacaatgaa gaggcaatgt ccatctcaaa atactgcttt tacaaaagca    4140
gaataaaagc gaaagaaat gaaaatgtta cactacatta atcctggaat aaaagaagcc     4200
gaaataaatg agagatgagt tgggatcaag tggattgagg aggctgtgct gtgtgccaat    4260
gtttcgtttg cctcagacag gtatctcttc gttatcagaa gagttgcttc atttcatctg    4320
ggagcagaaa acagcaggca gctgttaaca gataagttta acttgcatct gcagtattgc    4380
atgttaggga taagtgctta ttttttaagag ctgtggagtt cttaaatatc aaccatggca    4440
ctttctcctg acccccttccc tagggattt caggattgag aaattttcc atcgagcctt     4500 tttaaaattg taggacttgt tcctgtgggc ttcagtgatg ggatagtaca cttcactcag    4560
```

```
aggcatttgc atctttaaat aatttcttaa aagcctctaa agtgatcagt gccttgatgc    4620
caactaagga aatttgttta gcattgaatc tctgaaggct ctatgaaagg aatagcatga    4680
tgtgctgtta gaatcagatg ttactgctaa aatttacatg ttgtgatgta aattgtgtag    4740
aaaaccatta aatcattcaa aataataaac tattttatt agagaatgta acttttaga     4800 aagctgtctc cttatttaaa taaaatagtg tttgtctgta gttcagtgtt ggggcaatct    4860
tgggggggat tcttctctaa tctttcagaa actttgtctg cgaacactct ttaatggacc    4920
agatcaggat ttgagcggaa gaacgaatgt aactttaagg caggaaagac aaattttatt    4980
cttcataaag tgatgagcat ataataattc caggcacatg gcaatagagg ccctctaaat    5040
aaggaataaa taacctctta gacaggtggg agattatgat cagagtaaaa ggtaattaca    5100
cattttattt ccagaaagtc aggggtctat aaattgacag tgattagagt aatactttt    5160 cacatttcca aagtttgcat gttaaccttta aatgcttaca atcttagagt ggtaggcaat    5220
gttttacact attgacctta tagggaag ggaggggtg cctgtggggt tttaaagaat     5280
tttcctttgc agaggcattt catccttcat gaagccattc aggattttga attgcatatg    5340
agtgcttggc tcttccttct gttctagtga gtgtatgaga ccttgcagtg agtttatcag    5400
catactcaaa attttttcc tggaatttgg agggatggga ggaggggtg gggcttactt    5460 gttgtagctt tttttttttt tacagacttc acagagaatg cagttgtctt gacttcaggt    5520
ctgtctgttc tgttggcaag taaatgcagt actgttctga tcccgctgct attagaatgc    5580
attgtgaaac gactggagta tgattaaaag ttgtgttccc caatgcttgg agtagtgatt    5640
gttgaaggaa aaaatccagc tgagtgataa aggctgagtg ttgaggaaat ttctgcagtt    5700
ttaagcagtc gtatttgtga ttgaagctga gtacattttg ctggtgtatt tttaggtaaa    5760 atgcttttg ttcattctg gtggtgggag gggactgaag cctttagtct tttccagatg    5820
caaccttaaa atcagtgaca agaaacattc caaacaagca acagtcttca agaaattaaa    5880
ctggcaagtg gaaatgttta aacagttcag tgatctttag tgcattgttt atgtgtgggt    5940
ttctctctcc cctcccttgg tcttaattct tacatgcagg aacactcagc agacacacgt    6000
atgcgaaggg ccagagaagc cagacccagt aagaaaaaat agcctattta ctttaaataa    6060
accaaacatt ccattttaaa tgtggggatt gggaaccact agttctttca gatggtattc    6120
ttcagactat agaaggagct tccagttgaa ttccaccgtg acaaaatga ggaaaacagg     6180 tgaacaagct ttttctgtat ttacatacaa agtcagatca gttatgggac aatagtattg    6240
aatagatttc agctttatgc tggagtaact ggcatgtgag caaactgtgt tggcgtgggg    6300 gtggagggt gaggtgggcg ctaagccttt ttttaagatt tttcaggtac ccctcactaa    6360
aggcaccgaa ggcttaaagt aggacaacca tggagccttc ctgtggcagg agagacaaca    6420
aagcgctatt atcctaaggt caagagaagt gtcagcctca cctgatttt attagtaatg     6480 aggacttgcc tcaactccct ctttctggag tgaagcatcc gaaggaatgc ttgaagtacc    6540
cctgggcttc tcttaacatt taagcaagct gttttatag cagctcttaa taataaagcc     6600
caaatctcaa gcggtgcttg aaggggaggg aaggggggaa agcgggcaac cacttttccc    6660
tagcttttcc agaagcctgt taaaagcaag gtctccccac aagcaacttc tctgccacat    6720
cgccaccccg tgccttttga tctagcacag acccttcacc cctcacctcg atgcagccag    6780
tagcttggat ccttgtgggc atgatccata atcggtttca aggtaacgat ggtgtcgagg    6840
tctttggtgg gttgaactat gttagaaaag gccattaatt tgcctgcaaa ttgttaacag    6900
```

```
aagggtatta aaaccacagc taagtagctc tattataata cttatccagt gactaaaacc    6960
aacttaaacc agtaagtgga gaaataacat gttcaagaac tgtaatgctg ggtgggaaca    7020
tgtaacttgt agactggaga agataggcat ttgagtggct gagagggctt ttgggtggga    7080
atgcaaaaat tctctgctaa gacttttttca ggtgaacata acagacttgg ccaagctagc    7140
```
(reading) atgcaaaaat tctctgctaa gacttttttca ggtgaacata acagacttgg ccaagctagc    7140

```
atcttagcgg aagctgatct ccaatgctct tcagtagggt catgaaggtt tttcttttcc    7200
tgagaaaaca acacgtattg ttttctcagg ttttgctttt tggccttttt ctagcttaaa    7260
aaaaaaaaaa gcaaagatg ctggtggttg gcactcctgg tttccaggac ggggttcaaa    7320
tccctgcggt gtctttgctt tgactactaa tctgtcttca ggactctttc tgtatttctc    7380
cttttctctg caggtgctag ttcttggagt tttggggagg tgggaggtaa cagcacaata    7440
tctttgaact atatacatcc ttgatgtata atttgtcagg agcttgactt gattgtatat    7500
tcatatttac acgagaacct aatataactg ccttgtcttt ttcaggtaat agcctgcagc    7560
tggtgttttg agaagcccta ctgctgaaaa cttaacaatt ttgtgtaata aaaatggaga    7620
agctctaaat tgttgtggtt cttttggaat aaaaaaatct tgattgggaa aaaagatggg    7680
tgttctgtgg gcttgttctg ttaaatctgt ggtctataaa cacagcaccc ataattacag    7740
cataatcttc aagtagggta cggactttgg gggattggtg cgagggtagt gggtgagtgg    7800
cctactaaaa agcccagtaa cccccacagg aaaataggga acttcttttt aagtagcctc    7860
ctttccacta tttagtaatt ggctgtgagc tgggctgggg gagaaatggg gcggggtgtg    7920
tgtgtcattg gaaagctctc tttttttgttt ttttgagaca gtctcacttt gtcccccagg    7980
ctggagtgta gtggcatgat ctctgcaaac tgcaacctcc acttgtgggg tccaagtggt    8040
tgtcctgctt caccctccct gtagctggga ctacaggtgc acaccaccac gcctggctaa    8100
tttttgtatt                                                          8110
```

<210> SEQ ID NO 3
<211> LENGTH: 836
<212> TYPE: DNA
<213> ORGANISM: Homo sapiens
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t

<400> SEQUENCE: 3

```
gggaggactg gggccccgca actggcctct cctgccctct taagcgcagc gccatttttag     60 caacgcagaa gcccggcgcc gggaagcctc agctcgcctg aaggtggtaa actataccta    120
ctgtccctca agagaacaca agaagtgctt taagaggcgg cggaaggtga tcgaattccg    180
gtgatgcgag ttgttctccg tctataaata cgcctcgccc gagctgtgcg gtaggcattg    240
aggcagccag cgcaggggct tctgctgagg nggcaggcgg agcttgagga naccgcagat    300
aagttttttt ctctttgana gatagagatt aatacaacta cttaaaaaat atagtccata    360
ggttactaag atattgcttt agcgtaagtt tttaacgtaa ttttaatagc ttaggattct    420
aagagaaaat atggagactt agaagagtag catgagggag gaaaagataa aagggttcta    480
aaacatgacg ggaggttgag atgaagcttt cttcatggag taaaaaatgt atctaaaaag    540
```

```
aaatttgaga gaaaggacta ccgagccccc gaaattaata ccaataggaa gggccaatgc    600 ttttttagaat taaaatgaaa ggtggacctt aaaacaactt taaaagttta gttttaaaag   660
ttggaaaggt gattaaaaat aatttggaag ggcgatcttt tttaaaaaga ggattaaacc   720
cgaaagggaa ttaaaagaac ccttgaaatc cttgaaccca gggaaaaaat tgcgtccatt   780
ttaaagccct aagttaacgc attttcctaa aaccccaaca aaaaagtgga aaaatt       836
```

```
<210> SEQ ID NO 4
<211> LENGTH: 1082
<212> TYPE: DNA
<213> ORGANISM: Homo sapiens
<220> FEATURE:
<221> NAME/KEY: misc_feature
<222> LOCATION: (797)..(797)
<223> OTHER INFORMATION: n is a, c, g, or t
<220> FEATURE:
<221> NAME/KEY: misc_feature
<222> LOCATION: (1082)..(1082)
<223> OTHER INFORMATION: n is a, c, g, or t

<400> SEQUENCE: 4
```

```
gggcagcctg cagcccgaga cttctgtaaa ggactggggc cccgcaactg gcctctcctg    60
ccctcttaag cgcagcgcca ttttagcaac gcagaagccc ggcgccggga agcctcagct   120
cgcctgaagg cggcggaagg tgatcgaatt ccggtgatgc gagttgttct ccgtctataa   180
atacgcctcg cccgagctgt gcggtaggca ttgaggcagc cagcgcaggg gcttctgctg   240 aggggggcagg cggagcttga ggaaaccgca cataagtttt tttctctttg aaagatagag   300
attaatacaa cctacttaaa aaatataagc cactaggcta ctaacaaaat tggcttaacc   360
gctaaggttt tttaaccgaa attttttaata agccttaaga attttttaaga agaaaaatat   420 ggaagaaaact tgggaaacaa gtcaccctgt ggcggaaggg gaaaaacgga tttaataggg   480
ggttttcttt aaaaaacaat tgaaccggca cgggcgtcga aaaatatga aaaaaccttt    540 cccttcccac ttggggaagc tcaacaacaa ccacgcgggg aacgttgttt aaacaaatag   600
gaaaaaaaaa aatttgttgg cgacaaagag aaaacagggg ggaaccttag aacccggaag   660
agccccgccc ccggcaggaa ttttctacct cacccccct agatatagaa aaagggggg    720 gccacaacaa gggcattttc tttttttaaga gaatctctaa tccaccttgg ggagaggggg   780
gtggacacct ctataanaaa aaccaggcgt gtttagaaaa gcgttttctt atgatttttt    840
catacacaaa agatttgggt ataaagggag gtcgaccatc tacacacata aaaagaattt    900
ttttctcaaa aaccgcgcag taaacctctt cttttttacc cccaggagca ggcattattt    960 tatataccccc cgccgaggcg tgggggttat ttaaacacac cgagcctcat tctgttaata   1020
gatttcccca ctggagcgcc cccggtgggg ggagcactaa ctggtgtccg cgccttcttt   1080 tn                                                                 1082
```

```
<210> SEQ ID NO 5
<211> LENGTH: 13001
<212> TYPE: DNA
<213> ORGANISM: Homo sapiens

<400> SEQUENCE: 5
```

```
attactccct cattaataca atataaaaat tatttacgtt gtattaggta ttataagcaa     60
actagagatg atttaaggga tatgggagga tatctgtagg ttacataagg aacttgagca   120
tcttcagatt ttagcatccg aggagaggtt ttagaaccaa ggccccatgg ataccaaggg   180
```

| | |
|---|---|
| atgactgtac aacattctgg cggctgggca cagtggctca agcctgtaat cccagcactt | 240 |
| tgggaggccg aggcgggcgg atcacgaggt caggagatcc agaccatcct ggttaacacg | 300 |
| gtgaaaccct gtctctgcta aaactacaaa aaattagtcg ggcgtggtgg cgggcgcctg | 360 |
| tagtaccagc tactcgggag gctgaggcaa gtgaattgct tgaaccaggg aggcggaggt | 420 |
| tacggtgagc cgagatcccg ccactgcact ccagcctcag cgatagagtg agacttcgtc | 480 |
| tcaaaaaaaa aaaaaagaa acattctgta atctgtcaag gtaatggaaa ttaatgcagt | 540 |
| gacactgaca ataatttaaa gcattttagg gctcttaacg ttcatctcac tcgctctaga | 600 |
| gtgaaggaga gagcagagag tacagagcag gtcctaggtc ctcccccaga tatagaaaaa | 660 |
| ccgcagttgg agagactgac agaagtgctg gagaggaagg gaggcagcag gacgtggaaa | 720 |
| atctgggatt caagaacagc ttctgctatt aattagctgt gtgtcatttc aggcaaatca | 780 |
| caaaatctcc aggcccccaa atcccatt gcgaaacgag gtgacctgcc tcagttttcc | 840 |
| ttcatccagc gataaaattc tactaaaaaa tttccaaccc cagagcaagc atcaggactg | 900 |
| tgcctgaagg gatccggctg catctcagta atattccact cttacaggct taaaaataaa | 960 |
| aaagaaaaga aaagaaaaca gaacagtttt caccagcgtc aattgagaac agctgcttca | 1020 |
| acaggccctg ctttatgtgg gcaggtgggg acagggagtt ggcccagaaa acaggaccct | 1080 |
| catttcctgg agccccccagg gcagctcccc aacaccgtac acaacctgca tcatttacag | 1140 |
| gagccaaagg agttttagaa atcaacttca tagagttgct gtatcattgt gttagttttg | 1200 |
| ccatcctaac ctatacagcg tcactaatct ctcccctcgg agttgactgc ctaaaaacaa | 1260 |
| gccatggata caggttccaa agacccgggg gtgagggagc ggagagggtg ggtgtcacca | 1320 |
| ccccgtccag ctccaagctt tgtgtgccct ggaactctcc atttaggtc attgcttcag | 1380 |
| tttcttttct aaaaaattag gctgctgcaa ggtcagcctg agaccacttc tgccccgaga | 1440 |
| attctagact agtaagacct ggtgacatac aaacgacgaa gatattttac aataatgcca | 1500 |
| tggcccttga tagctacacg aggtttgtgt tctgatttta aattaatgga tgacgtcgag | 1560 |
| actatatgga ggaaatgaca aaggacagga gagaggtggg aaaggaagac ctagactgaa | 1620 |
| aatggaagtt gggcagcagc tccacgaaag aaagaccagc ccccaagtgc agtgacagcg | 1680 |
| cagagtagcg accgagaagt tcccaggcca gctgccaccc cgcccccatg ccattcccca | 1740 |
| gaacaggcac aggcgttagg gcggggcgcg cgtgcgcagt cacgcgctgc gccaaccgcc | 1800 |
| acagctccgg gaaggcggcc aggaccggct agagccggtt agaaccagtg gcgcccgccc | 1860 |
| acgagccagc gcctcacaaa gggagggcgg ctcacggccc tcgcgtatcc ctgcgcggcg | 1920 |
| ctcgcgagcc gccccctcccc cggcgtttgt ccctgacgca gccccaccgg ttgcgcagtc | 1980 |
| cctccccgcc ccgctctcc cctccgcagc ctgcagcccg agacttctgt aaaggactgg | 2040 |
| ggccccgcaa ctggcctctc ctgccctctt aagcgcagcg ccattttagc aacgcagaag | 2100 |
| cccggcgccg ggaagcctca gctcgcctga aggcaggtcc cctctgacgc ctccgggagc | 2160 |
| ccaggtttcc cagagtccctt gggacgcagc gacgagttgt gctgctatct tagctgtcct | 2220 |
| tataggctgg ccattccagg tggtggtatt tagataaaac cactcaaact ctgcagtttg | 2280 |
| gtcttggggt ttggaggaaa gcttttattt ttcttcctgc tccggttcag aaggtctgaa | 2340 |
| gctcatacct aaccaggcat aacacagaat ctgcaaaaca aaaccccta aaaaagcaga | 2400 |
| cccagagcag tgtaaacact tctgggtgtg tccctgactg gctgcccaag gtctctgtgt | 2460 |
| cttcggagac aaagccattc gcttagtggg tctactttaa aaggccactt gaactcgctt | 2520 |
| tccatggcga tttgccttgt gagcactttc aggagagcct ggaagctgaa aaacggtaga | 2580 |

```
aaaatttccg tgcgggccgt ggggggctgg cggcaactgg ggggccgcag atcagagtgg    2640
gccactggca gccaacggcc cccgggtc aggcggggag cagctctgtg gtgtgggatt    2700
gaggcgtttt ccaagagtgg gttttcacgt ttctaagatt tcccaagcag acagcccgtg    2760
ctgctccgat ttctcgaaca aaaaagcaaa acgtgtggct gtcttgggag caagtcgcag    2820
gactgcaagc agttggggga gaaagtccgc cattttgcca cttctcaacc gtccctgcaa    2880
ggctggggct cagttgcgta atggaaagta aagccctgaa ctatcacact ttaatcttcc    2940
ttcaaaaggt ggtaaactat acctactgtc cctcaagaga acacaagaag tgctttaaga    3000
ggtattttaa aagttccggg ggttttgtga ggtgtttgat gacccgttta aaatatgatt    3060
tccatgtttc ttttgtctaa agtttgcagc tcaaatcttt ccacacgcta gtaatttaag    3120
tatttctgca tgtgtagttt gcattcaagt tccataagct gttaagaaaa atctagaaaa    3180
gtaaaactag aacctatttt taaccgaaga actacttttt gcctccctca caaaggcggc    3240
ggaaggtgat cgaattccgg tgatgcgagt tgttctccgt ctataaatac gcctcgcccg    3300
agctgtgcgg taggcattga ggcagccagc gcagggcctt ctgctgaggg ggcaggcgga    3360
gcttgaggaa accgcagata agttttttc tctttgaaag atagagatta atacaactac    3420
ttaaaaaata tagtcaatag gttactaaga tattgcttag cgttaagttt ttaacgtaat    3480
tttaatagct taagatttta agagaaaata tgaagactta aagagtagc atgaggaagg    3540 aaaagataaa aggtttctaa acatgacgg aggttgagat gaagcttctt catggagtaa    3600
aaaatgtatt taaagaaaa ttgagagaaa ggactacaga gccccgaatt aataccaata    3660
gaagggcaat gcttttagat taaaatgaag gtgacttaaa cagcttaaag tttagtttaa    3720
aagttgtagg tgattaaaat aatttgaagg cgatctttta aaagagatt aaaccgaagg    3780 tgattaaaag accttgaaat ccatgacgca gggagaattg cgtcatttaa agcctagtta    3840
acgcatttac taaacgcaga cgaaaatgga aagattaatt gggagtggta ggatgaaaca    3900
atttggagaa gatagaagtt tgaagtggaa aactggaaga cagaagtacg ggaaggcgaa    3960
gaaaagaata gagaagatag ggaaattaga agataaaaac atactttag aagaaaaag    4020 ataaatttaa acctgaaaag taggaagcag aagaaaaag acaagctagg aaacaaaaag    4080
ctaagggcaa aatgtacaaa cttagaagaa aattggaaga tagaaacaag atagaaaatg    4140
aaaatattgt caagagtttc agatagaaaa tgaaaaacaa gctaagacaa gtattggaga    4200
agtatagaag atagaaaaat ataaagccaa aaattggata aaatagcact gaaaaatga    4260 ggaaattatt ggtaaccaat ttatttaaa agcccatcaa tttaatttct ggtggtgcag    4320
aagttagaag gtaaagcttg agaagatgag ggtgtttacg tagaccagaa ccaatttaga    4380
agaatacttg aagctagaag gggaagttgg ttaaaaatca catcaaaaag ctactaaaag    4440
gactggtgta atttaaaaaa aactaaggca gaaggctttt ggaagagtta aagaatttg    4500 gaaggcctta aatatagtag cttagtttga aaaatgtgaa ggactttcgt aacgaagta    4560 attcaagatc aagagtaatt accaacttaa tgttttgca ttggactttg agttaagatt    4620
attttttaaa tcctgaggac tagcattaat tgacagctga cccaggtgct acacagaagt    4680
ggattcagtg aatctaggaa gacagcagca gacaggattc caggaaccag tgtttgatga    4740
agctaggact gaggagcaag cgagcaagca gcagttcgtg gtgaagatag gaaaagagtc    4800
caggagccag tgcgatttgg tgaaggaagc taggaagaag gaaggagcgc taacgatttg    4860
gtggtgaagc taggaaaaag gattccagga aggagcgagt gcaatttggt gatgaaggta    4920
```

```
gcaggcggct tggcttggca accacacgga ggaggcgagc aggcgttgtg cgtagaggat    4980
cctagaccag catgccagtg tgccaaggcc acagggaaag cgagtggttg gtaaaaatcc    5040
gtgaggtcgg caatatgttg tttttctgga acttacttat ggtaaccttt tatttatttt    5100
ctaatataat gggggagttt cgtactgagg tgtaaaggga tttatatggg gacgtaggcc    5160
gatttccggg tgttgtaggt ttctcttttt caggcttata ctcatgaatc ttgtctgaag    5220
cttttgaggg cagactgcca agtcctggag aaatagtaga tggcaagttt gtgggttttt    5280
tttttttaca cgaatttgag gaaaaccaaa tgaatttgat agccaaattg agacaatttc    5340
agcaaatctg taagcagttt gtatgtttag ttggggtaat gaagtatttc agttttgtga    5400
atagatgacc tgttttttact tcctcaccct gaattcgttt tgtaaatgta gagtttggat    5460
gtgtaactga ggcgggggggg agttttcagt attttttttt gtggggtggg ggcaaaata    5520 tgttttcagt tctttttccc ttaggtctgt ctagaatcct aaaggcaaat gactcaaggt    5580
gtaacagaaa acaagaaaat ccaatatcag gataatcaga ccaccacagg tttacagttt    5640
atagaaacta gagcagttct cacgttgagg tctgtggaag agatgtccat tggagaaatg    5700
gctggtagtt actcttttt cccccacccc ccttaatcag actttaaaag tgcttaaccc    5760
cttaaacttg ttattttta cttgaagcat tttgggatgg tcttaacagg gaagagagag    5820
ggtgggggag aaaatgtttt tttctaagat tttccacaga tgctatagta ctattgacaa    5880
actgggttag agaaggagtg taccgctgtg ctgttggcac gaacaccttc agggactgga    5940 gctgcttta tccttggaag agtattccca gttgaagctg aaaagtacag cacagtgcag    6000
ctttggttca tattcagtca tctcaggaga acttcagaag agcttgagta ggccaaatgt    6060
tgaagttaag ttttccaata atgtgacttc ttaaaagttt tattaaaggg gagggggcaaa    6120 tattggcaat tagttggcag tggcctgtta cggttgggat tggtggggtg ggtttaggta    6180
attgtttagt ttatgattgc agataaactc atgccagaga acttaaagtc ttagaatgga    6240
aaaagtaaag aaatatcaac ttccaagttg gcaagtaact cccaatgatt tagttttttt    6300 cccccccagtt tgaattggga agctgggga agttaaatat gagccactgg gtgtaccagt    6360
gcattaattt gggcaaggaa agtgtcataa tttgatactg tatctgtttt ccttcaaagt    6420
atagagcttt tggggaagga aagtattgaa ctgggggttg gtctggccta ctgggctgac    6480
attaactaca attatgggaa atgcaaaagt tgtttggata tggtagtgtg tggttctctt    6540
ttggaatttt tttcaggtga tttaataata atttaaaact actatagaaa ctgcagagca    6600
aaggaagtgg cttaatgatc ctgaagggat ttccttctgat ggtagctttt gtattatcaa    6660
gtaagattct attttcagtt gtgtgtaagc aagtttttt ttagtgtagg agaaatactt    6720
ttccattgtt taactgcaaa acaagatgtt aaggtatgct tcaaaaattt tgtaaattgt    6780
ttattttaaa cttatctgtt tgtaaattgt aactgattaa gaattgtgat agttcagctt    6840
gaatgtctct tagagggtgg gcttttgttg atgagggagg ggaaactttt tttttttcta    6900
tagacttttt tcagataaca tcttctgagt cataaccagc ctggcagtat gatggcctag    6960
atgcagagaa aacagctcct tggtgaattg ataagtaaag gcagaaaaga ttatatgtca    7020
tacctccatt ggggaataag cataaccctg agattcttac tactgatgag aacattatct    7080
gcatatgcca aaaaatttta agcaaatgaa agctaccaat ttaaagttac ggaatctacc    7140
attttaaagt taattgcttg tcaagctata accacaaaaa taatgaattg atgagaaata    7200
caatgaagag gcaatgtcca tctcaaaata ctgctttttac aaaagcagaa taaaagcgaa    7260
aagaaatgaa aatgttacac tacattaatc ctggaataaa agaagccgaa ataaatgaga    7320
```

```
gatgagttgg gatcaagtgg attgaggagg ctgtgctgtg tgccaatgtt tcgtttgcct    7380
cagacaggta tctcttcgtt atcagaagag ttgcttcatt tcatctggga gcagaaaaca    7440
gcaggcagct gttaacagat aagtttaact tgcatctgca gtattgcatg ttagggataa    7500
gtgcttattt ttaagagctg tggagttctt aaatatcaac catggcactt tctcctgacc    7560
ccttccctag gggatttcag gattgagaaa ttttccatc gagcctttt aaaattgtag    7620 gacttgttcc tgtgggcttc agtgatggga tagtacactt cactcagagg catttgcatc    7680
tttaaataat ttcttaaaag cctctaaagt gatcagtgcc ttgatgccaa ctaaggaaat    7740
ttgtttagca ttgaatctct gaaggctcta tgaaaggaat agcatgatgt gctgttagaa    7800
tcagatgtta ctgctaaaat ttacatgttg tgatgtaaat tgtgtagaaa accattaaat    7860
cattcaaaat aataaactat ttttattaga gaatgtatac ttttagaaag ctgtctcctt    7920
atttaaataa aatagtgttt gtctgtagtt cagtgttggg gcaatcttgg gggggattct    7980
tctctaatct ttcagaaact ttgtctgcga acactcttta atggaccaga tcaggatttg    8040
agcggaagaa cgaatgtaac tttaaggcag gaaagacaaa ttttattctt cataaagtga    8100
tgagcatata ataattccag gcacatggca atagaggccc tctaaataag gaataaataa    8160
cctcttagac aggtgggaga ttatgatcag agtaaaaggt aattacacat tttatttcca    8220
gaaagtcagg ggtctataaa ttgacagtga ttagagtaat acttttttcac atttccaaag    8280 tttgcatgtt aactttaaat gcttacaatc ttagagtggt aggcaatgtt ttacactatt    8340
gaccttatat agggaaggga gggggtgcct gtggggtttt aaagaatttt cctttgcaga    8400
ggcatttcat ccttcatgaa gccattcagg atttttgaatt gcatatgagt gcttggctct    8460
tccttctgtt ctagtgagtg tatgagacct tgcagtgagt ttatcagcat actcaaaatt    8520 ttttttcctgg aatttggagg gatgggagga ggggtgggg cttacttgtt gtagcttttt    8580 tttttttttac agacttcaca gagaatgcag ttgtcttgac ttcaggtctg tctgttctgt    8640
tggcaagtaa atgcagtact gttctgatcc cgctgctatt agaatgcatt gtgaaacgac    8700
tggagtatga ttaaaagttg tgttccccaa tgcttggagt agtgattgtt gaaggaaaaa    8760
atccagctga gtgataaagg ctgagtgttg aggaaatttc tgcagtttta agcagtcgta    8820
tttgtgattg aagctgagta cattttgctg gtgtattttt aggtaaaatg cttttttgttc    8880 atttctggtg gtgggagggg actgaagcct ttagtctttt ccagatgcaa ccttaaaatc    8940
agtgacaaga acattccaa acaagcaaca gtcttcaaga aattaaactg gcaagtggaa    9000
atgtttaaac agttcagtga tctttagtgc attgtttatg tgtgggtttc tctctcccct    9060
cccttggtct taattcttac atgcaggaac actcagcaga cacacgtatg cgaagggcca    9120
gagaagccag acccagtaag aaaaaatagc ctatttactt taaataaacc aaacattcca    9180
ttttaaatgt ggggattggg aaccactagt tctttcagat ggtattcttc agactataga    9240
aggagcttcc agttgaattc accagtggac aaaatgagga aaacaggtga caagcttttt    9300
tctgtattta catacaaagt cagatcagtt atgggacaat agtattgaat agatttcagc    9360
tttatgctgg agtaactggc atgtgagcaa actgtgttgg cgtgggggtg gaggggtgag    9420
gtgggcgcta agccttttt taagatttt caggtacccc tcactaaagg caccgaaggc    9480
ttaaagtagg acaaccatgg agccttcctg tggcaggaga gacaacaaag cgctattatc    9540
ctaaggtcaa gagaagtgtc agcctcacct gattttttatt agtaatgagg acttgcctca    9600
actccctctt tctggagtga agcatccgaa ggaatgcttg aagtacccct gggcttctct    9660
```

```
taacatttaa gcaagctgtt tttatagcag ctcttaataa taaagcccaa atctcaagcg   9720
gtgcttgaag gggagggaaa gggggaaagc gggcaaccac ttttccctag cttttccaga   9780
agcctgttaa aagcaaggtc tccccacaag caacttctct gccacatcgc caccccgtgc   9840
cttttgatct agcacagacc cttcacccct cacctcgatg cagccagtag cttggatcct   9900
tgtgggcatg atccataatc ggtttcaagg taacgatggt gtcgaggtct ttggtgggtt   9960
gaactatgtt agaaaaggcc attaatttgc ctgcaaattg ttaacagaag ggtattaaaa  10020
ccacagctaa gtagctctat tataatactt atccagtgac taaaaccaac ttaaaccagt  10080
aagtggagaa ataacatgtt caagaactgt aatgctgggt gggaacatgt aacttgtaga  10140
ctggagaaga taggcatttg agtggctgag agggcttttg ggtgggaatg caaaaattct  10200
ctgctaagac ttttcaggt gaacataaca gacttggcca agctagcatc ttagcggaag  10260
ctgatctcca atgctcttca gtagggtcat gaaggttttt cttttcctga gaaacaaca   10320 cgtattgttt tctcaggttt tgcttttttgg ccttttttcta gcttaaaaaa aaaaaagca  10380 aaagatgctg gtggttggca ctcctggttt ccaggacggg gttcaaatcc ctgcggcgtc  10440
tttgctttga ctactaatct gtcttcagga ctctttctgt atttctcctt ttctctgcag  10500
gtgctagttc ttggagtttt ggggaggtgg gaggtaacag cacaatatct ttgaactata  10560
tacatccttg atgtataatt tgtcaggagc ttacttgat tgtatattca tatttacacg   10620
agaacctaat ataactgcct tgtctttttc aggtaatagc ctgcagctgg tgttttgaga  10680
agccctactg ctgaaaactt aacaattttg tgtaataaaa atggagaagc tctaaattgt  10740
tgtggttctt ttgtgaataa aaaaatcttg attgggaaa aaagatgggt gttctgtggg  10800
cttgttctgt taaatctgtg gtctataaac acagcaccca taattacagc ataatcttca  10860
agtagggtac ggactttggg ggattggtgc gagggtagtg ggtgagtggc ctactaaaaa  10920
gcccagtaac ccccacagga aaatagggaa cttcttttta agtagcctcc tttccactat  10980
ttagtaattg gctgtgagct gggctgggg agaaatgggg cggggtgtgt gtgtcattgg  11040
aaagctctct ttttttgtttt tttgagacag tctcactttg tcccccaggc tggagtgtag  11100
tggcatgatc tctgcaaact gcaacctcca cttctgggt ccaagtggtt gtcctgcttc   11160
accctccctg tagctgggac tacaggtgca caccaccacg cctggctaat ttttgtattt  11220
tcagttagag acgtggtttt accatattgg ccaggctggt ctcaaactcc tgacctcgtg  11280
tgatccaccc gcctgggcct ctgaaagtgc tgggattaca ggtgtgagcc accaagcctg  11340
gccgatcctt ttaagttttt aaaccagtta agctctttgg ttcccctca gagtcccaag  11400 gtcctgggtc actcaggatc acatttttcct ttaatcagtt gtcactggtc cccttttgtc  11460
cctttgaacg tgctgtggga ttagtagcag catctggctg ttggaaggac tggctgggat  11520
ctcaggtgaa ataccctccc tggccctcct tacccttaag atctccctga aaagtcagac  11580
cttgcttatt ggagtttgag atgcattcta gtaaacccag acctaccaga gagagggacc  11640
cacgtctgaa gaatcttcca gcctggggaa cctgtgactg gccacaccct tagcctaatg  11700
gaggggcctc agaagcagaa ctacctttt tttttttttt aatggtatta cattttgcaa  11760
atggagaggt agactctgat tgggcccctt ttgacaacgc agcagagctg aggtttgaat  11820
cctagtcagt caacacttca acccctatgt tgctgtttct tcaatgtcta gaatgttctg  11880
atagatgaag caatggcccg gcaggtcagc agcacaccaa ccccccaacct acccagcctg  11940 tataggcctt ggccacagga gctttctctt cccttgaagt gatctaatgg gggatggggt  12000
atctgtctcg ctggttatga aagaagctga gctaggtgct ctcctaagtt gcttaagtgt  12060
```

```
cttctgaatt gatgcccagt cagtttcgta tggagaaagg tctctgtttt tccaaagcag    12120
aaggttctgt ggaagcacaa atactttact ggagagcaaa ggagtacgag taggaattgg    12180
gggccacgca cagtggctca cgcctataat cccaggactt gggaggccg aggtgggcag     12240 atcacctgag gtcaggagtt cgagaccagc ctgaccaaca tggagaaacc ccatctctac    12300
taaaaataca aaattagccg ggcgtggtgg cgtatgtctg taaccccagc tattcgagag    12360
gctgaggtag gagaatcgct tggacccggg aggcggaggt tgcagtgagc tgagattgcg    12420
ccactgcact ccagcctggg caacaagagc gaaactgtct caaaaaaaaa aaaaaagaa     12480 gaagaaaggc tgggcacggt ggctcaagcc tgtaatccca gcactttggg aggccgaggc    12540
gggcggatca cgaagtcagg agattgaaac catcctggct aacacggtga aaccccgtct    12600
ctactacaca cacacacaca cacacacaca cacacacaca cacacacaca atttgctggg    12660
cgtggtggag ggcgcctgta gtcctagcta ctcgtgaggc tgaggcagga aatggcgtg    12720 aacctgggag gcggagcttg ccgtgaggtg agatcgggcc actgcactcc agcctgggcg    12780
acagagcgag actccgtctt aaaaaaaaaa aaaaaaaaa aaagagtagg agctgggcat     12840
tcgccagggg ctacgtagtt cctggagttg aggaagttct ccaggattga aaaatgtaaa    12900
gatcagacac tgatcacagc aacaggagga ggcagaaaag taggccggaa gtcatttcca    12960
ccctctgagc acaaaatgga gagcataaat tccccaaaag c                        13001

<210> SEQ ID NO 6
<211> LENGTH: 8986
<212> TYPE: DNA
<213> ORGANISM: Homo sapiens

<400> SEQUENCE: 6
ctctcccctc cgcagcctgc agcccgagac ttctgtaaag gactggggcc ccgcaactgg      60
cctctcctgc cctcttaagc gcagcgccat tttagcaacg cagaagcccg cgccgggaa     120 gcctcagctc gcctgaaggc aggtcccctc tgacgcctcc gggagcccag gtttcccaga    180
gtccttggga cgcagcgacg agttgtgctg ctatcttagc tgtccttata ggctggccat    240
tccaggtggt ggtatttaga taaaaccact caaactctgc agtttggtct tggggtttgg    300
aggaaagctt ttatttttct tcctgctccg gttcagaagg tctgaagctc atacctaacc    360
aggcataaca cagaatctgc aaaacaaaaa cccctaaaaa agcagaccca gagcagtgta    420
aacacttctg ggtgtgtccc tgactggctg cccaaggtct ctgtgtcttc ggagacaaag    480
ccattcgctt agttggtcta cttttaaaagg ccacttgaac tcgctttcca tggcgatttg    540
ccttgtgagc actttcagga gagcctggaa gctgaaaaac ggtagaaaaa tttccgtgcg    600
ggccgtgggg ggctggcggc aactgggggg ccgcagatca gagtgggcca ctggcagcca    660
acggcccccg gggctcaggc ggggagcagc tctgtggtgt gggattgagg cgttttccaa    720
gagtgggttt tcacgtttct aagatttccc aagcagacag cccgtgctgc tccgatttct    780
cgaacaaaaa agcaaaacgt gtggctgtct tgggagcaag tcgcaggact gcaagcagtt    840
gggggagaaa gtccgccatt ttgccacttc tcaaccgtcc ctgcaaggct ggggctcagt    900
tgcgtaatgg aaagtaaagc cctgaactat cacactttaa tcttccttca aaaggtggta    960
aactatacct actgtccctc aagagaacac aagaagtgct ttaagaggcg gcggaaggtg   1020
atcgaattcc ggtgatgcga gttgttctcc gtctataaat acgcctcgcc cgagctgtgc   1080
ggtaggcatt gaggcagcca gcgcaggggc ttctgctgag ggggcaggcg gagcttgagg   1140
```

```
aaaccgcaga taagttttttt tctctttgaa agatagagat taatacaact acttaaaaaa    1200
tatagtcaat aggttactaa gatattgctt agcgttaagt ttttaacgta attttaatag    1260
cttaagattt taagagaaaa tatgaagact tagaagagta gcatgaggaa ggaaaagata    1320
aaaggtttct aaaacatgac ggaggttgag atgaagcttc ttcatggagt aaaaaatgta    1380
tttaaaagaa aattgagaga aaggactaca gagccccgaa ttaataccaa tagaagggca    1440
atgcttttag attaaaatga aggtgactta aacagcttaa agtttagttt aaagttgta    1500 ggtgattaaa ataatttgaa ggcgatcttt taaaaagaga ttaaaccgaa ggtgattaaa    1560
agaccttgaa atccatgacg cagggagaat tgcgtcattt aaagcctagt taacgcattt    1620
actaaacgca gacgaaaatg gaaagattaa ttgggagtgg taggatgaaa caatttggag    1680
aagatagaag tttgaagtgg aaaactggaa gacagaagta cgggaaggcg aagaaaagaa    1740
tagagaagat agggaaatta gaagataaaa acatactttt agaagaaaaa agataaattt    1800
aaacctgaaa agtaggaagc agaagaaaaa agacaagcta ggaaacaaaa agctaagggc    1860
aaaatgtaca aacttagaag aaaattggaa gatagaaaca agatagaaaa tgaaaatatt    1920
gtcaagagtt tcagatagaa aatgaaaaac aagctaagac aagtattgga gaagtataga    1980
agatagaaaa atataaagcc aaaaattgga taaaatagca ctgaaaaaat gaggaaatta    2040
ttggtaacca atttatttta aaagcccatc aatttaattt ctggtggtgc agaagttaga    2100
aggtaaagct tgaagagatg agggtgttta cgtagaccag aaccaattta gaagaatact    2160
tgaagctaga aggggaagtt ggttaaaaat cacatcaaaa agctactaaa aggactggtg    2220
taatttaaaa aaaactaagg cagaaggctt ttggaagagt tagaagaatt tggaaggcct    2280
taaatatagt agcttagttt gaaaaatgtg aaggactttc gtaacggaag taattcaaga    2340
tcaagagtaa ttaccaactt aatgttttg cattggactt tgagttaaga ttattttta    2400 aatcctgagg actagcatta attgacagct gacccaggtg ctacacagaa gtggattcag    2460
tgaatctagg aagacagcag cagacaggat tccaggaacc agtgtttgat gaagctagga    2520
ctgaggagca agcgagcaag cagcagttcg tggtgaagat aggaaaagag tccaggagcc    2580
agtgcgattt ggtgaaggaa gctaggaaga aggaaggagc gctaacgatt tggtggtgaa    2640
gctaggaaaa aggattccag gaaggagcga gtgcaatttg gtgatgaagg tagcaggcgg    2700
cttggcttgg caaccacacg gaggaggcga gcaggcgttg tgcgtagagg atcctagacc    2760
agcatgccag tgtgccaagg ccacagggaa agcgagtggt tggtaaaaat ccgtgaggtc    2820
ggcaatatgt tgttttttctg gaacttactt atggtaacct tttatttatt ttctaatata    2880 atggggagt ttcgtactga ggtgtaaagg gatttatatg gggacgtagg ccgatttccg    2940
ggtgttgtag gtttctcttt ttcaggctta tactcatgaa tcttgtctga agcttttgag    3000
ggcagactgc caagtcctgg agaaatagta gatggcaagt ttgtgggttt ttttttttta    3060
cacgaatttg aggaaaacca aatgaatttg atagccaaat tgagacaatt tcagcaaatc    3120
tgtaagcagt ttgtatgttt agttgggta atgaagtatt tcagttttgt gaatagatga    3180
cctgttttta cttcctcacc ctgaattcgt tttgtaaatg tagagtttgg atgtgtaact    3240
gaggcggggg ggagttttca gtatttttt ttgtgggggt ggggcaaaa tatgttttca    3300 gttcttttc ccttaggtct gtctagaatc ctaaaggcaa atgactcaag gtgtaacaga    3360
aaacaagaaa atccaatatc aggataatca gaccaccaca ggtttacagt ttatagaaac    3420
tagagcagtt ctcacgttga ggtctgtgga agagatgtcc attggagaaa tggctggtag    3480
ttactctttt ttccccccac ccccttaatc agactttaaa agtgcttaac cccttaaact    3540
```

```
tgttattttt tacttgaagc attttgggat ggtcttaaca gggaagagag agggtggggg    3600
agaaaatgtt tttttctaag attttccaca gatgctatag tactattgac aaactgggtt    3660
agagaaggag tgtaccgctg tgctgttggc acgaacacct tcagggactg gagctgcttt    3720
tatccttgga agagtattcc cagttgaagc tgaaaagtac agcacagtgc agctttggtt    3780
catattcagt catctcagga gaacttcaga agagcttgag taggccaaat gttgaagtta    3840
agttttccaa taatgtgact tcttaaaagt tttattaaag gggaggggca aatattggca    3900
attagttggc agtggcctgt tacggttggg attggtgggg tgggtttagg taattgttta    3960
gtttatgatt gcagataaac tcatgccaga gaacttaaag tcttagaatg gaaaagtaa     4020 agaaatatca acttccaagt tggcaagtaa ctcccaatga tttagttttt ttccccccag    4080
tttgaattgg gaagctgggg gaagttaaat atgagccact gggtgtacca gtgcattaat    4140
ttgggcaagg aaagtgtcat aatttgatac tgtatctgtt ttccttcaaa gtatagagct    4200
tttggggaag gaaagtattg aactgggggt tggtctggcc tactgggctg acattaacta    4260
caattatggg aaatgcaaaa gttgtttgga tatggtagtg tgtggttctc ttttggaatt    4320
tttttcaggt gatttaataa taatttaaaa ctactataga aactgcagag caaaggaagt    4380
ggcttaatga tcctgaaggg atttcttctg atggtagctt ttgtattatc aagtaagatt    4440
ctattttcag ttgtgtgtaa gcaagttttt ttttttagtgt aggagaaata cttttccatt    4500
gtttaactgc aaaacaagat gttaaggtat gcttcaaaaa ttttgtaaat tgtttatttt    4560
aaacttatct gtttgtaaat tgtaactgat taagaattgt gatagttcag cttgaatgtc    4620
tcttagaggg tgggctttttg ttgatgaggg aggggaaact ttttttttttt ctatagactt    4680 ttttcagata acatcttctg agtcataacc agcctggcag tatgatggcc tagatgcaga    4740
gaaaacagct ccttggtgaa ttgataagta aaggcagaaa agattatatg tcatacctcc    4800
attggggaat aagcataacc ctgagattct tactactgat gagaacatta tctgcatatg    4860
ccaaaaaatt ttaagcaaat gaaagctacc aatttaaagt tacggaatct accattttaa    4920
agttaattgc ttgtcaagct ataaccacaa aaataatgaa ttgatgagaa atacaatgaa    4980
gaggcaatgt ccatctcaaa atactgcttt tacaaaagca gaataaaagc gaaagaaat     5040 gaaaatgtta cactacatta atcctggaat aaaagaagcc gaaataaatg agagatgagt    5100
tgggatcaag tggattgagg aggctgtgct gtgtgccaat gtttcgtttg cctcagacag    5160
gtatctcttc gttatcagaa gagttgcttc atttcatctg ggagcagaaa acagcaggca    5220
gctgttaaca gataagttta acttgcatct gcagtattgc atgttaggga taagtgctta    5280
tttttaagag ctgtggagtt cttaaatatc aaccatggca ctttctcctg accccttccc    5340 tagggggattt caggattgag aaattttttcc atcgagcctt tttaaaattg taggacttgt    5400
tcctgtgggc ttcagtgatg ggatagtaca cttcactcag aggcatttgc atctttaaat    5460
aatttcttaa aagcctctaa agtgatcagt gccttgatgc caactaagga aatttgttta    5520
gcattgaatc tctgaaggct ctatgaaagg aatagcatga tgtgctgtta gaatcagatg    5580
ttactgctaa aatttacatg ttgtgatgta aattgtgtag aaaaccatta aatcattcaa    5640
aataataaac tattttttatt agagaatgta tacttttaga aagctgtctc cttatttaaa    5700
taaaatagtg tttgtctgta gttcagtgtt ggggcaatct tggggggat tcttctctaa     5760 tctttcagaa acttttgtctg cgaacactct ttaatggacc agatcaggat ttgagcggaa    5820
gaacgaatgt aactttaagg caggaaagac aaatttatt cttcataaag tgatgagcat     5880
```

```
ataataattc caggcacatg gcaatagagg ccctctaaat aaggaataaa taacctctta    5940
gacaggtggg agattatgat cagagtaaaa ggtaattaca cattttattt ccagaaagtc    6000
aggggtctat aaattgacag tgattagagt aatactttt cacatttcca aagtttgcat    6060
gttaacttta aatgcttaca atcttagagt ggtaggcaat gttttacact attgaccttta   6120 tatagggaag ggaggggtg cctgtggggt tttaaagaat tttccttttgc agaggcattt    6180 catccttcat gaagccattc aggattttga attgcatatg agtgcttggc tcttccttct    6240
gttctagtga gtgtatgaga ccttgcagtg agtttatcag catactcaaa attttttcc     6300 tggaatttgg agggatggga ggagggggtg gggcttactt gttgtagctt ttttttttt     6360 tacagacttc acagagaatg cagttgtctt gacttcaggt ctgtctgttc tgttggcaag    6420
taaatgcagt actgttctga tcccgctgct attagaatgc attgtgaaac gactggagta    6480
tgattaaaag ttgtgttccc caatgcttgg agtagtgatt gttgaaggaa aaaatccagc    6540
tgagtgataa aggctgagtg ttgaggaaat ttctgcagtt ttaagcagtc gtatttgtga    6600
ttgaagctga gtacattttg ctggtgtatt tttaggtaaa atgcttttg ttcatttctg     6660 gtggtgggag gggactgaag cctttagtct tttccagatg caaccttaaa atcagtgaca    6720
agaaacattc caaacaagca acagtcttca agaaattaaa ctggcaagtg gaaatgttta    6780
aacagttcag tgatctttag tgcattgttt atgtgtgggt ttctctctcc cctcccttgg    6840
tcttaattct tacatgcagg aacactcagc agacacacgt atgcgaaggg ccagagaagc    6900
cagacccagt aagaaaaaat agcctattta ctttaaataa accaaacatt ccatttaaa    6960 tgtgggatt gggaaccact agttctttca gatggtattc ttcagactat agaaggagct     7020
tccagttgaa ttcaccagtg gacaaaatga ggaaaacagg tgaacaagct ttttctgtat    7080
ttacatacaa agtcagatca gttatgggac aatagtattg aatagatttc agctttatgc    7140
tggagtaact ggcatgtgag caaactgtgt tggcgtgggg gtggaggggt gaggtgggcg    7200
ctaagccttt ttttaagatt tttcaggtac ccctcactaa aggcaccgaa ggcttaaagt    7260
aggacaacca tggagccttc ctgtggcagg agagacaaca aagcgctatt atcctaaggt    7320
caagagaagt gtcagcctca cctgattttt attagtaatg aggacttgcc tcaactccct    7380
ctttctggag tgaagcatcc gaaggaatgc ttgaagtacc cctgggcttc tcttaacatt    7440
taagcaagct gttttttatag cagctcttaa taataaagcc caaatctcaa gcggtgcttg    7500 aagggagg aaaggggaa agcgggcaac cacttttccc tagctttcc agaagcctgt        7560 taaaagcaag gtctccccac aagcaacttc tctgccacat cgccaccccg tgccttttga    7620
tctagcacag acccttcacc cctcacctcg atgcagccag tagcttggat ccttgtgggc    7680
atgatccata atcggtttca aggtaacgat ggtgtcgagg tctttggtgg ttgaactat     7740 gttagaaaag gccattaatt tgcctgcaaa ttgttaacag aagggtatta aaaccacagc    7800
taagtagctc tattataata cttatccagt gactaaaacc aacttaaacc agtaagtgga    7860
gaaataacat gttcaagaac tgtaatgctg ggtgggaaca tgtaacttgt agactggaga    7920
agataggcat ttgagtggct gagagggctt ttgggtggga atgcaaaaat tctctgctaa    7980 gacttttca ggtgaacata acagacttgg ccaagctagc atcttagcgg aagctgatct     8040
ccaatgctct tcagtagggt catgaaggtt tttcttttcc tgagaaaaca acacgtattg    8100
ttttctcagg ttttgctttt tggccttttt ctagcttaaa aaaaaaaaa gcaaagatg      8160 ctggtggttg gcactcctgg tttccaggac ggggttcaaa tccctgcggc gtctttgctt    8220
tgactactaa tctgtcttca ggactctttc tgtatttctc cttttctctg caggtgctag    8280
```

| | |
|---|---|
| ttcttggagt tttggggagg tgggaggtaa cagcacaata tctttgaact atatacatcc | 8340 |
| ttgatgtata atttgtcagg agcttgactt gattgtatat tcatatttac acgagaacct | 8400 |
| aatataactg ccttgtcttt ttcaggtaat agcctgcagc tggtgttttg agaagcccta | 8460 |
| ctgctgaaaa cttaacaatt ttgtgtaata aaaatggaga agctctaaat tgttgtggtt | 8520 |
| cttttgtgaa taaaaaaatc ttgattgggg aaaaaagatg ggtgttctgt gggcttgttc | 8580 |
| tgttaaatct gtggtctata aacacagcac ccataattac agcataatct tcaagtaggg | 8640 |
| tacggacttt gggggattgg tgcgagggta gtgggtgagt ggcctactaa aaagcccagt | 8700 |
| aaccccaca ggaaaatagg gaacttcttt ttaagtagcc tcctttccac tatttagtaa | 8760 |
| ttggctgtga gctgggctgg gggagaaatg gggcggggtg tgtgtgtcat tggaaagctc | 8820 |
| tcttttttgt tttttttgaga cagtctcact ttgtccccca ggctggagtg tagtggcatg | 8880 |
| atctctgcaa actgcaacct ccacttctgg ggtccaagtg gttgtcctgc ttcaccctcc | 8940 |
| ctgtagctgg gactacaggt gcacaccacc acgcctggct aatttt | 8986 |

<210> SEQ ID NO 7
<211> LENGTH: 8708
<212> TYPE: DNA
<213> ORGANISM: Homo sapiens

<400> SEQUENCE: 7

| | |
|---|---|
| gtaaaggact ggggccccgc aactggcctc tcctgccctc ttaagcgcag cgccatttta | 60 |
| gcaacgcaga agcccggcgc cgggaagcct cagctcgcct gaaggcaggt cccctctgac | 120 |
| gcctccggga gcccaggttt cccagagtcc ttgggacgca gcgacgagtt gtgctgctat | 180 |
| cttagctgtc cttataggct ggccattcca ggtggtggta tttagataaa accactcaaa | 240 |
| ctctgcagtt tggtcttggg gtttggagga aagcttttat ttttcttcct gctccggttc | 300 |
| agaaggtctg aagctcatac ctaaccaggc ataacacaga atctgcaaaa caaaaacccc | 360 |
| taaaaagca gacccagagc agtgtaaaca cttctgggtg tgtccctgac tggctgccca | 420 |
| aggtctctgt gtcttcggag acaaagccat tcgcttagtt ggtctacttt aaaaggccac | 480 |
| ttgaactcgc tttccatggc gatttgcctt gtgagcactt tcaggagagc ctggaagctg | 540 |
| aaaaacggta gaaaaatttc cgtgcgggcc gtgggggggct ggcggcaact gggggccgc | 600 |
| agatcagagt gggccactgg cagccaacgg ccccgggc tcaggcgggg agcagctctg | 660 |
| tggtgtggga ttgaggcgtt ttccaagagt gggttttcac gtttctaaga tttcccaagc | 720 |
| agacagcccg tgctgctccg atttctcgaa caaaaaagca aaacgtgtgg ctgtcttggg | 780 |
| agcaagtcgc aggactgcaa gcagttgggg gagaaagtcc gccattttgc cacttctcaa | 840 |
| ccgtccctgc aaggctgggg ctcagttgcg taatggaaag taaagccctg aactatcaca | 900 |
| cttttaatctt ccttcaaaag gtggtaaact atacctactg tccctcaaga gaacacaaga | 960 |
| agtgctttaa gaggtatttt aaaagttccg ggggttttgt gaggtgtttg atgaccccgtt | 1020 |
| taaaatatga tttccatgtt tcttttgtct aaagtttgca gctcaaatct ttccacacgc | 1080 |
| tagtaattta agtatttctg catgtgtagt ttgcattcaa gttccataag ctgttaagaa | 1140 |
| aaatctagaa aagtaaaact agaacctatt tttaaccgaa gaactacttt ttgcctccct | 1200 |
| cacaaaggcg gcggaaggtg atcgaattcc ggtgatgcga ttgttctcc gtctataaat | 1260 |
| acgcctcgcc cgagctgtgc ggtaggcatt gaggcagcca gcgcagggc ttctgctgag | 1320 |
| ggggcaggcg gagcttgagg aaaccgcaga taagtttttt tctctttgaa agatagagat | 1380 |

```
taatacaact acttaaaaaa tatagtcaat aggttactaa gatattgctt agcgttaagt    1440 tttttaacgta attttaatag cttaagattt taagagaaaa tatgaagact tagaagagta    1500
gcatgaggaa ggaaaagata aaaggtttct aaaacatgac ggaggttgag atgaagcttc    1560
ttcatggagt aaaaaatgta tttaaaagaa aattgagaga aaggactaca gagccccgaa    1620
ttaataccaa tagaagggca atgctttag  attaaaatga aggtgactta aacagcttaa    1680
agtttagttt aaaagttgta ggtgattaaa ataatttgaa ggcgatcttt taaaaagaga    1740
ttaaaccgaa ggtgattaaa agaccttgaa atccatgacg cagggagaat tgcgtcattt    1800
aaagcctagt taacgcattt actaaacgca gacgaaaatg gaaagattaa ttgggagtgg    1860
taggatgaaa caatttggag aagatagaag tttgaagtgg aaaactggaa gacagaagta    1920
cgggaaggcg aagaaaagaa tagagaagat agggaaatta aagataaaa  acatactttt    1980 agaagaaaaa agataaattt aaacctgaaa agtaggaagc agaagaaaaa agacaagcta    2040
ggaaacaaaa agctaagggc aaaatgtaca aacttagaag aaaattggaa gatagaaaca    2100
agatagaaaa tgaaaatatt gtcaagagtt tcagatagaa aatgaaaaac aagctaagac    2160
aagtattgga gaagtataga agatagaaaa atataaagcc aaaaattgga taaaatagca    2220
ctgaaaaaat gaggaaatta ttggtaacca atttatttta aaagcccatc aatttaattt    2280
ctggtggtgc agaagttaga aggtaaagct tgagaagatg agggtgttta cgtagaccag    2340
aaccaattta gaagaatact tgaagctaga aggggaagtt ggttaaaaat cacatcaaaa    2400
agctactaaa aggactggtg taatttaaaa aaaactaagg cagaaggctt ttggaagagt    2460
tagaagaatt tggaaggcct taaatatagt agcttagttt gaaaaatgtg aaggactttc    2520
gtaacggaag taattcaaga tcaagagtaa ttaccaactt aatgttttg  cattggactt    2580 tgagttaaga ttatttttta aatcctgagg actagcatta attgacagct gacccaggtg    2640
ctacacagaa gtggattcag tgaatctagg aagacagcag cagacaggat tccaggaacc    2700
agtgtttgat gaagctagga ctgaggagca agcgagcaag cagcagttcg tggtgaagat    2760
aggaaaagag tccaggagcc agtgcgattt ggtgaaggaa gctaggaaga aggaaggagc    2820
gctaacgatt tggtggtgaa gctaggaaaa aggattccag gaaggagcga gtgcaatttg    2880
gtgatgaagg tagcaggcgg cttggcttgg caaccacacg gaggaggcga gcaggcgttg    2940
tgcgtagagc atcctagacc agcatgccag tgtgccaagg ccacagggaa agcgagtggt    3000
tggtaaaaat ccgtgaggtc ggcaatatgt tgttttctg  gaacttactt atggtaacct    3060
tttatttatt ttctaatata atgggggagt ttcgtactga ggtgtaaagg gatttatatg    3120
gggacgtagg ccgatttccg ggtgttgtag gtttctcttt ttcaggctta tactcatgaa    3180
tcttgtctga agcttttgag ggcagactgc caagtcctgg agaaatagta gatggcaagt    3240
ttgtgggttt ttttttttta cacgaatttg aggaaaacca aatgaatttg atagccaaat    3300
tgagacaatt tcagcaaatc tgtaagcagt ttgtatgttt agttgggta  atgaagtatt    3360 tcagttttgt gaatagatga cctgttttta cttcctcacc ctgaattcgt tttgtaaatg    3420
tagagtttgg atgtgtaact gaggcggggg ggagttttca gtatttttt  ttgtggggt    3480 ggggggcaaaa tatgttttca gttctttttc ccttaggtct gtctagaatc ctaaaggcaa    3540
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt ttccccccac cccttaatc  agactttaaa    3720 agtgcttaac cccttaaact tgttattttt tacttgaagc attttgggat ggtcttaaca    3780
```

```
gggaagagag agggtggggg agaaaatgtt ttttctaag attttccaca gatgctatag   3840
tactattgac aaactgggtt agagaaggag tgtaccgctg tgctgttggc acgaacacct   3900
tcagggactg gagctgcttt tatccttgga agagtattcc cagttgaagc tgaaaagtac   3960
agcacagtgc agctttggtt catattcagt catctcagga gaacttcaga agagcttgag   4020
taggccaaat gttgaagtta agttttccaa taatgtgact tcttaaaagt tttattaaag   4080
gggaggggca aatattggca attagttggc agtggcctgt tacggttggg attggtgggg   4140
tgggtttagg taattgttta gtttatgatt gcagataaac tcatgccaga gaacttaaag   4200
tcttagaatg gaaaaagtaa agaaatatca acttccaagt tggcaagtaa ctcccaatga   4260
tttagttttt ttccccccag tttgaattgg gaagctgggg gaagttaaat atgagccact   4320
gggtgtacca gtgcattaat ttgggcaagg aaagtgtcat aatttgatac tgtatctgtt   4380
ttccttcaaa gtatagagct tttggggaag gaaagtattg aactgggggt tggtctggcc   4440
tactgggctg acattaacta caattatggg aaatgcaaaa gttgtttgga tatggtagtg   4500
tgtggttctc ttttggaatt ttttttcaggt gatttaataa taatttaaaa ctactataga   4560
aactgcagag caaggaagt ggcttaatga tcctgaaggg atttcttctg atggtagctt   4620
ttgtattatc aagtaagatt ctattttcag ttgtgtgtaa gcaagttttt ttttagtgta   4680
ggagaaatac ttttccattg tttaactgca aaacaagatg ttaaggtatg cttcaaaaat   4740
tttgtaaatt gtttatttta aacttatctg tttgtaaatt gtaactgatt aagaattgtg   4800
atagttcagc ttgaatgtct cttagagggt gggcttttgt tgatgaggga ggggaaactt   4860 ttttttttc tatagacttt tttcagataa catcttctga gtcataacca gcctggcagt   4920
atgatggcct agatgcagag aaaacagctc cttggtgaat tgataagtaa aggcagaaaa   4980
gattatatgt catacctcca ttggggaata agcataaccc tgagattctt actactgatg   5040
agaacattat ctgcatatgc caaaaaattt taagcaaatg aaagctacca atttaaagtt   5100
acggaatcta ccatttaaa gttaattgct tgtcaagcta taaccacaaa aataatgaat   5160
tgatgagaaa tacaatgaag aggcaatgtc catctcaaaa tactgctttt acaaaagcag   5220
aataaaagcg aaaagaaatg aaaatgttac actacattaa tcctggaata aaagaagccg   5280
aaataaatga gagatgagtt gggatcaagt ggattgagga ggctgtgctg tgtgccaatg   5340
tttcgtttgc ctcagacagg tatctcttcg ttatcagaag agttgcttca tttcatctgg   5400
gagcagaaaa cagcaggcag ctgttaacag ataagtttaa cttgcatctg cagtattgca   5460
tgttagggat aagtgcttat ttttaagagc tgtggagttc ttaaatatca accatggcac   5520
tttctcctga cccccttccct agggatttc aggattgaga aatttttcca tcgagccttt   5580
ttaaaattgt aggacttgtt cctgtgggct tcagtgatgg gatagtacac ttcactcaga   5640
ggcatttgca tcttaaata atttcttaaa agcctctaaa gtgatcagtg ccttgatgcc   5700
aactaaggaa atttgtttag cattgaatct ctgaaggctc tatgaaagga atagcatgat   5760
gtgctgttag aatcagatgt tactgctaaa atttacatgt tgtgatgtaa attgtgtaga   5820
aaaccattaa atcattcaaa ataataaact attttattta gagaatgtat acttttagaa   5880
agctgtctcc ttatttaaat aaaatagtgt ttgtctgtag ttcagtgttg gggcaatctt   5940 ggggggggatt cttctctaat ctttcagaaa ctttgtctgc gaacactctt taatggacca   6000
gatcaggatt tgagcggaag aacgaatgta actttaaggc aggaaagaca aattttattc   6060
ttcataaagt gatgagcata taataattcc aggcacatgg caatagaggc cctctaaata   6120
```

```
aggaataaat aacctcttag acaggtggga gattatgatc agagtaaaag gtaattacac    6180
attttatttc cagaaagtca ggggtctata aattgacagt gattagagta atacttttc     6240 acatttccaa agtttgcatg ttaactttaa atgcttacaa tcttagagtg gtaggcaatg    6300
ttttacacta ttgaccttat atagggaagg gaggggtgc ctgtgggtt ttaaagaatt      6360 ttcctttgca gaggcatttc atccttcatg aagccattca ggattttgaa ttgcatatga    6420
gtgcttggct cttccttctg ttctagtgag tgtatgagac cttgcagtga gtttatcagc    6480
atactcaaaa ttttttttcct ggaatttgga gggatgggag gaggggtgg ggcttacttg    6540 ttgtagcttt tttttttttt acagacttca cagagaatgc agttgtcttg acttcaggtc    6600
tgtctgttct gttggcaagt aaatgcagta ctgttctgat cccgctgcta ttagaatgca    6660
ttgtgaaacg actggagtat gattaaaagt tgtgttcccc aatgcttgga gtagtgattg    6720
ttgaaggaaa aaatccagct gagtgataaa ggctgagtgt tgaggaaatt tctgcagttt    6780
taagcagtcg tatttgtgat tgaagctgag tacattttgc tggtgtattt ttaggtaaaa    6840 tgcttttttgt tcatttctgg tggtgggagg ggactgaagc ctttagtctt ttccagatgc   6900
aaccttaaaa tcagtgacaa gaaacattcc aaacaagcaa cagtcttcaa gaaattaaac    6960
tggcaagtgg aaatgtttaa acagttcagt gatctttagt gcattgttta tgtgtgggtt    7020
tctctctccc ctcccttggt cttaattctt acatgcagga acactcagca gacacacgta    7080
tgcgaagggc cagagaagcc agacccagta agaaaaaata gcctatttac tttaaataaa    7140
ccaaacattc cattttaaat gtggggattg ggaaccacta gttctttcag atggtattct    7200
tcagactata gaaggagctt ccagttgaat tcaccagtgg acaaaatgag gaaaacaggt    7260
gaacaagctt tttctgtatt tacatacaaa gtcagatcag ttatgggaca atagtattga    7320
atagatttca gctttatgct ggagtaactg gcatgtgagc aaactgtgtt ggcgtggggg    7380 tggagggtg aggtgggcgc taagcctttt tttaagattt ttcaggtacc cctcactaaa     7440
ggcaccgaag gcttaaagta ggacaaccat ggagccttcc tgtggcagga gagacaacaa    7500
agcgctatta tcctaaggtc aagagaagtg tcagcctcac ctgatttttaa ttagtaatga   7560 ggacttgcct caactccctc tttctggagt gaagcatccg aaggaatgct tgaagtaccc    7620
ctgggcttct cttaacattt aagcaagctg tttttatagc agctcttaat aataaagccc    7680
aaatctcaag cggtgcttga aggggaggga aaggggggaaa gcgggcaacc acttttccct   7740
agcttttcca gaagcctgtt aaaagcaagg tctccccaca agcaacttct ctgccacatc    7800 gccacccgt gccttttgat ctagcacaga cccttcaccc ctcacctcga tgcagccagt     7860
agcttggatc cttgtgggca tgatccataa tcggtttcaa ggtaacgatg gtgtcgaggt    7920
ctttggtggg ttgaactatg ttagaaaagg ccattaattt gcctgcaaat tgttaacaga    7980
agggtattaa aaccacagct aagtagctct attataatac ttatccagtg actaaaacca    8040 acttaaaacca gtaagtggag aaataacatg ttcaagaact gtaatgctgg gtgggaacat   8100
gtaacttgta gactggagaa gataggcatt tgagtggctg agagggcttt tgggtgggaa    8160
tgcaaaaatt ctctgctaag acttttcag gtgaacataa cagacttggc caagctagca    8220
tcttagcgga agctgatctc caatgctctt cagtagggtc atgaaggttt ttcttttcct    8280
gagaaaacaa cacgtattgt tttctcaggt tttgctttt ggcctttttc tagcttaaaa     8340
aaaaaaaaag caaagatgc tggtggttgg cactcctggt ttccaggacg gggttcaaat     8400
ccctgcggcg tctttgcttt gactactaat ctgtcttcag gactctttct gtatttctcc    8460
ttttctctgc aggtgctagt tcttggagtt ttggggaggt gggaggtaac agcacaatat    8520
```

```
ctttgaacta tatacatcct tgatgtataa tttgtcagga gcttgacttg attgtatatt    8580
catatttaca cgagaaccta atataactgc cttgtctttt tcaggtaata gcctgcagct    8640
ggtgttttga gaagccctac tgctgaaaac ttaacaattt tgtgtaataa aaatggagaa    8700
gctctaaa                                                             8708
```

<210> SEQ ID NO 8
<211> LENGTH: 8708
<212> TYPE: DNA
<213> ORGANISM: Homo sapiens

<400> SEQUENCE: 8

```
gtaaaggact ggggccccgc aactggcctc tcctgccctc ttaagcgcag cgccatttta      60
gcaacgcaga agcccggcgc cgggaagcct cagctcgcct gaaggcaggt cccctctgac     120
gcctccggga gcccaggttt cccagagtcc ttgggacgca gcgacgagtt gtgctgctat     180
cttagctgtc cttataggct ggccattcca gtggtggta tttagataaa accactcaaa     240
ctctgcagtt tggtcttggg gtttggagga aagcttttat ttttcttcct gctccggttc     300
agaaggtctg aagctcatac ctaaccaggc ataacacaga atctgcaaaa caaaaacccc     360 taaaaagca gacccagagc agtgtaaaca cttctgggtg tgtccctgac tggctgccca     420
aggtctctgt gtcttcggag acaaagccat tcgcttagtt ggtctacttt aaaaggccac     480
ttgaactcgc tttccatggc gatttgcctt gtgagcactt tcaggagagc ctggaagctg     540
aaaaacggta gaaaaatttc cgtgcgggcc gtgggggct gcggcaact gggggccgc      600 agatcagagt gggccactgg cagccaacgg ccccgggc tcaggcgggg agcagctctg      660
tggtgtggga ttgaggcgtt ttccaagagt gggttttcac gtttctaaga tttcccaagc     720
agacagcccg tgctgctccg atttctcgaa caaaaaagca aaacgtgtgg ctgtcttggg     780
agcaagtcgc aggactgcaa gcagttgggg gagaaagtcc gccattttgc cacttctcaa     840
ccgtccctgc aaggctgggg ctcagttgcg taatggaaag taaagccctg aactatcaca     900
ctttaatctt ccttcaaaag gtggtaaact atacctactg tccctcaaga gaacacaaga     960
agtgctttaa gaggtatttt aaaagttccg ggggttttgt gaggtgtttg atgacccgtt    1020
taaaatatga tttccatgtt tcttttgtct aaagtttgca gctcaaatct ttccacacgc    1080
tagtaattta agtatttctg catgtgtagt ttgcattcaa gttccataag ctgttaagaa    1140
aaatctagaa aagtaaaact agaaccatt tttaaccgaa gaactacttt ttgcctccct    1200
cacaaaggcg gcgaaggtg atcgaattcc ggtgatgcga gttgttctcc gtctataaat    1260
acgcctcgcc cgagctgtgc ggtaggcatt gaggcagcca gcgcaggggc ttctgctgag    1320
ggggcaggcg gagcttgagg aaaccgcaga taagttttt tctctttgaa agatagagat    1380
taatacaact acttaaaaaa tatagtcaat aggttactaa gatattgctt agcgttaagt    1440
ttttaacgta atttaatag cttaagattt taagagaaaa tatgaagact tagaagagta    1500
gcatgaggaa ggaaaagata aaaggtttct aaaacatgac ggaggttgag atgaagcttc    1560
ttcatggagt aaaaaatgta tttaaaagaa aattgagaga aaggactaca gagccccgaa    1620
ttaataccaa tagaagggca atgctttag attaaaatga aggtgactta aacagcttaa    1680
agtttagttt aaaagttgta ggtgattaaa ataatttgaa ggcgatcttt taaaaagaga    1740
ttaaaccgaa ggtgattaaa agaccttgaa atccatgacg cagggagaat tgcgtcattt    1800
aaagcctagt taacgcattt actaaacgca gacgaaaatg gaaagattaa ttgggagtgg    1860
```

| | |
|---|---|
| taggatgaaa caatttggag aagatagaag tttgaagtgg aaaactggaa gacagaagta | 1920 |
| cgggaaggcg aagaaaagaa tagagaagat agggaaatta gaagataaaa acatactttt | 1980 |
| agaagaaaaa agataaattt aaacctgaaa agtaggaagc agaagaaaaa agacaagcta | 2040 |
| ggaaacaaaa agctaagggc aaaatgtaca aacttagaag aaaattggaa gatagaaaca | 2100 |
| agatagaaaa tgaaatatat gtcaagagtt tcagatagaa aatgaaaaac aagctaagac | 2160 |
| aagtattgga gaagtataga agatagaaaa atataaagcc aaaaattgga taaaatagca | 2220 |
| ctgaaaaaat gaggaaatta ttggtaacca atttatttta aaagcccatc aatttaattt | 2280 |
| ctggtggtgc agaagttaga aggtaaagct tgagaagatg agggtgttta cgtagaccag | 2340 |
| aaccaattta gaagaatact tgaagctaga aggggaagtt ggttaaaaat cacatcaaaa | 2400 |
| agctactaaa aggactggtg taatttaaaa aaaactaagg cagaaggctt ttggaagagt | 2460 |
| tagaagaatt tggaaggcct taaatatagt agcttagttt gaaaaatgtg aaggactttc | 2520 |
| gtaacggaag taattcaaga tcaagagtaa ttaccaactt aatgttttg cattggactt | 2580 |
| tgagttaaga ttattttta aatcctgagg actagcatta attgacagct gacccaggtg | 2640 |
| ctacacagaa gtggattcag tgaatctagg aagacagcag cagacaggat tccaggaacc | 2700 |
| agtgtttgat gaagctagga ctgaggagca agcgagcaag cagcagttcg tggtgaagat | 2760 |
| aggaaaagag tccaggagcc agtgcgattt ggtgaaggaa gctaggaaga aggaaggagc | 2820 |
| gctaacgatt tggtggtgaa gctaggaaaa aggattccag gaaggagcga gtgcaatttg | 2880 |
| gtgatgaagg tagcaggcgg cttggcttgg caaccacacg gaggaggcga gcaggcgttg | 2940 |
| tgcgtagagg atcctagacc agcatgccag tgtgccaagg ccacagggaa agcgagtggt | 3000 |
| tggtaaaaat ccgtgaggtc ggcaatatgt tgttttctg gaacttactt atggtaacct | 3060 |
| tttatttatt ttctaatata atgggggagt ttcgtactga ggtgtaaagg gatttatatg | 3120 |
| gggacgtagg ccgatttccg ggtgttgtag gtttctcttt ttcaggctta tactcatgaa | 3180 |
| tcttgtctga agcttttgag ggcagactgc caagtcctgg agaaatagta gatggcaagt | 3240 |
| ttgtgggttt ttttttttta cacgaatttg aggaaaacca aatgaatttg atagccaaat | 3300 |
| tgagacaatt tcagcaaatc tgtaagcagt ttgtatgttt agttgggta atgaagtatt | 3360 |
| tcagttttgt gaatagatga cctgttttta cttcctcacc ctgaattcgt tttgtaaatg | 3420 |
| tagagtttgg atgtgtaact gaggcggggg ggagttttca gtattttttt ttgtgggggt | 3480 |
| ggggggcaaaa tatgttttca gttctttttc ccttaggtct gtctagaatc ctaaaggcaa | 3540 |
| atgactcaag gtgtaacaga aaacaagaaa atccaatatc aggataatca gaccaccaca | 3600 |
| ggtttacagt ttatagaaac tagagcagtt ctcacgttga ggtctgtgga agagatgtcc | 3660 |
| attggagaaa tggctggtag ttactctttt ttccccccac cccttaatc agactttaaa | 3720 |
| agtgcttaac cccttaaact tgttatttt tacttgaagc attttgggat ggtcttaaca | 3780 |
| gggaagagag agggtggggg agaaaatgtt tttttctaag attttccaca gatgctatag | 3840 |
| tactattgac aaactgggtt agagaaggag tgtaccgctg tgctgttggc acgaacacct | 3900 |
| tcagggactg gagctgcttt tatccttgga agagtattcc cagttgaagc tgaaaagtac | 3960 |
| agcacagtgc agctttggtt catattcagt catctcagga gaacttcaga agagcttgag | 4020 |
| taggccaaat gttgaagtta agttttccaa taatgtgact tcttaaaagt tttattaaag | 4080 |
| gggaggggca atattggca attagttggc agtggcctgt tacggttggg attggtgggg | 4140 |
| tgggtttagg taattgttta gtttatgatt gcagataaac tcatgccaga gaacttaaag | 4200 |
| tcttagaatg gaaaaagtaa agaaatatca acttccaagt tggcaagtaa ctcccaatga | 4260 |

```
tttagttttt ttcccccccag tttgaattgg gaagctgggg gaagttaaat atgagccact    4320
gggtgtacca gtgcattaat ttgggcaagg aaagtgtcat aatttgatac tgtatctgtt    4380
ttccttcaaa gtatagagct tttggggaag gaaagtattg aactgggggt tggtctggcc    4440
tactgggctg acattaacta caattatggg aaatgcaaaa gttgtttgga tatggtagtg    4500
tgtggttctc ttttggaatt tttttcaggt gatttaataa taatttaaaa ctactataga    4560
aactgcagag caaaggaagt ggcttaatga tcctgaaggg atttcttctg atggtagctt    4620
ttgtattatc aagtaagatt ctattttcag ttgtgtgtaa gcaagttttt tttagtgta    4680
ggagaaatac ttttccattg tttaactgca aaacaagatg ttaaggtatg cttcaaaaat    4740
tttgtaaatt gtttatttta aacttatctg tttgtaaatt gtaactgatt aagaattgtg    4800
atagttcagc ttgaatgtct cttagagggt gggcttttgt tgatgaggga ggggaaactt    4860
tttttttttc tatagacttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaaattt taagcaaatg aaagctacca atttaaagtt    5100
acggaatcta ccattttaaa gttaattgct tgtcaagcta taaccacaaa aataatgaat    5160
tgatgagaaa tacaatgaag aggcaatgtc catctcaaaa tactgctttt acaaaagcag    5220
aataaaagcg aaagaaatg aaaatgttac actacattaa tcctggaata aaagaagccg    5280
aaataaatga gagatgagtt gggatcaagt ggattgagga ggctgtgctg tgtgccaatg    5340
tttcgtttgc ctcagacagg tatctcttcg ttatcagaag agttgcttca tttcatctgg    5400
gagcagaaaa cagcaggcag ctgttaacag ataagtttaa cttgcatctg cagtattgca    5460
tgttagggat aagtgcttat ttttaagagc tgtggagttc ttaaatatca accatggcac    5520
tttctcctga ccccttccct aggggatttc aggattgaga aattttttcca tcgagccttt    5580
ttaaaattgt aggacttgtt cctgtgggct tcagtgatgg gatagtacac ttcactcaga    5640
ggcatttgca tctttaaata atttcttaaa agcctctaaa gtgatcagtg ccttgatgcc    5700
aactaaggaa atttgtttag cattgaatct ctgaaggctc tatgaaagga atagcatgat    5760
gtgctgttag aatcagatgt tactgctaaa atttacatgt tgtgatgtaa attgtgtaga    5820
aaaccattaa atcattcaaa ataataaact attttattta gagaatgtat acttttagaa    5880
agctgtctcc ttatttaaat aaaatagtgt ttgtctgtag ttcagtgttg gggcaatctt    5940
ggggggggatt cttctctaat ctttcagaaa cttttgtctgc gaacactctt taatggacca    6000
gatcaggatt tgagcggaag aacgaatgta actttaaggc aggaaagaca aattttattc    6060
ttcataaagt gatgagcata taataattcc aggcacatgg caatagaggc cctctaaata    6120
aggaataaat aacctcttag acaggtggga gattatgatc agagtaaaag gtaattacac    6180
attttatttc cagaaagtca ggggtctata aattgacagt gattagagta atactttttc    6240
acatttccaa agtttgcatg ttaactttaa atgcttacaa tcttagagtg gtaggcaatg    6300
ttttacacta ttgaccttat atagggaagg gaggggtgc ctgtgggtt ttaaagaatt    6360
ttcctttgca gaggcatttc atccttcatg aagccattca ggattttgaa ttgcatatga    6420
gtgcttggct cttccttctg ttctagtgag tgtatgagac cttgcagtga gtttatcagc    6480
atactcaaaa ttttttttcct ggaatttgga gggatgggag gaggggtgg ggcttacttg    6540
ttgtagcttt tttttttttt acagacttca cagagaatgc agttgtcttg acttcaggtc    6600
```

```
tgtctgttct gttggcaagt aaatgcagta ctgttctgat cccgctgcta ttagaatgca    6660
ttgtgaaacg actggagtat gattaaaagt tgtgttcccc aatgcttgga gtagtgattg    6720
ttgaaggaaa aaatccagct gagtgataaa ggctgagtgt tgaggaaatt tctgcagttt    6780
taagcagtcg tatttgtgat tgaagctgag tacattttgc tggtgtattt ttaggtaaaa    6840 tgcttttgt tcatttctgg tggtgggagg ggactgaagc ctttagtctt ttccagatgc     6900
aaccttaaaa tcagtgacaa gaaacattcc aaacaagcaa cagtcttcaa gaaattaaac    6960
tggcaagtgg aaatgtttaa acagttcagt gatctttagt gcattgttta tgtgtgggtt    7020
tctctctccc ctcccttggt cttaattctt acatgcagga acactcagca gacacacgta    7080
tgcgaagggc cagagaagcc agacccagta agaaaaaata gcctatttac tttaaataaa    7140
ccaaacattc cattttaaat gtggggattg ggaaccacta gttctttcag atggtattct    7200
tcagactata gaaggagctt ccagttgaat tcaccagtgg acaaaatgag gaaaacaggt    7260
gaacaagctt tttctgtatt tacatacaaa gtcagatcag ttatgggaca atagtattga    7320
atagatttca gctttatgct ggagtaactg gcatgtgagc aaactgtgtt ggcgtggggg    7380
tggaggggtg aggtgggcgc taagccttt tttaagattt ttcaggtacc cctcactaaa     7440
ggcaccgaag gcttaaagta ggacaaccat ggagccttcc tgtggcagga gagacaacaa    7500
agcgctatta tcctaaggtc aagagaagtg tcagcctcac ctgattttta ttagtaatga    7560
ggacttgcct caactccctc tttctggagt gaagcatccg aaggaatgct tgaagtaccc    7620
ctgggcttct cttaacattt aagcaagctg tttttatagc agctcttaat aataaagccc    7680
aaatctcaag cggtgcttga aggggaggga aaggggggaaa gcggcaacc acttttccct    7740 agcttttcca gaagcctgtt aaaagcaagg tctccccaca agcaacttct ctgccacatc    7800
gccaccccgt gccttttgat ctagcacaga cccttcaccc ctcacctcga tgcagccagt    7860
agcttggatc cttgtgggca tgatccataa tcggtttcaa ggtaacgatg gtgtcgaggt    7920 cttttggtggg ttgaactatg ttagaaaagg ccattaattt gcctgcaaat tgttaacaga    7980
agggtattaa aaccacagct aagtagctct attataatac ttatccagtg actaaaacca    8040 acttaaaacca gtaagtggag aaataacatg ttcaagaact gtaatgctgg gtgggaacat    8100
gtaacttgta gactggagaa gataggcatt tgagtggctg agagggcttt tgggtgggaa    8160
tgcaaaaatt ctctgctaag acttttttcag gtgaacataa cagacttggc caagctagca    8220
tcttagcgga agctgatctc caatgctctt cagtagggtc atgaaggttt ttcttttcct    8280
gagaaaacaa cacgtattgt tttctcaggt tttgcttttt ggccttttttc tagcttaaaa    8340 aaaaaaaaag caaaagatgc tggtggttgg cactcctggt ttccaggacg gggttcaaat    8400
ccctgcggcg tctttgcttt gactactaat ctgtcttcag gactctttct gtatttctcc    8460
ttttctctgc aggtgctagt tcttggagtt ttggggaggt gggaggtaac agcacaatat    8520
ctttgaacta tatacatcct tgatgtgtaa tttgtcagga gcttgacttg attgtatatt    8580
catatttaca cgagaaccta atataactgc cttgtctttt tcaggtaata gcctgcagct    8640
ggtgttttga gaagccctac tgctgaaaac ttaacaattt tgtgtaataa aaatggagaa    8700
gctctaaa                                                            8708
```

<210> SEQ ID NO 9
<211> LENGTH: 8708
<212> TYPE: DNA
<213> ORGANISM: Homo sapiens

<400> SEQUENCE: 9

-continued

```
gtaaaggact ggggccccgc aactggcctc tcctgccctc ttaagcgcag cgccatttta      60
gcaacgcaga agcccggcgc cgggaagcct cagctcgcct gaaggcaggt ccctctgac     120
gcctccggga gcccaggttt cccagagtcc ttgggacgca gcgacgagtt gtgctgctat     180
cttagctgtc cttataggct ggccattcca ggtggtggta tttagataaa accactcaaa     240
ctctgcagtt tggtcttggg gtttggagga aagcttttat ttttcttcct gctccggttc     300
agaaggtctg aagctcatac ctaaccaggc ataacacaga atctgcaaaa caaaaacccc     360
taaaaaagca gacccagagc agtgtaaaca cttctgggtg tgtccctgac tggctgccca     420
aggtctctgt gtcttcggag acaaagccat tcgcttagtt ggtctacttt aaaaggccac     480
ttgaactcgc tttccatggc gatttgcctt gtgagcactt tcaggagagc ctggaagctg     540
aaaaacggta gaaaaatttc cgtgcgggcc gtgggggggct ggcggcaact gggggggccgc    600
agatcagagt gggccactgg cagccaacgg cccccggggc tcaggcgggg agcagctctg     660
tggtgtggga ttgaggcgtt ttccaagagt gggttttcac gtttctaaga tttcccaagc     720
agacagcccg tgctgctccg atttctcgaa caaaaaagca aaacgtgtgg ctgtcttggg     780
agcaagtcgc aggactgcaa gcagttgggg gagaaagtcc gccatttttgc cacttctcaa    840
ccgtccctgc aaggctgggg ctcagttgcg taatggaaag taaagccctg aactatcaca     900
ctttaatctt ccttcaaaag gtggtaaact atacctactg tccctcaaga gaacacaaga     960
agtgctttaa gaggtatttt aaaagttccg ggggttttgt gaggtgtttg atgacccgtt    1020
taaaatatga tttccatgtt tcttttgtct aaagtttgca gctcaaatct ttccacacgc    1080
tagtaattta agtatttctg catgtgtagt ttgcattcaa gttccataag ctgttaagaa    1140
aaatctagaa aagtaaaact agaacctatt tttaaccgaa gaactacttt ttgcctccct    1200
cacaaaggcg gcggaaggtg atcgaattcc ggtgatgcga gttgttctcc gtctataaat    1260
acgcctcgcc cgagctgtgc ggtaggcatt gaggcagcca gcgcaggggc ttctgctgag    1320
ggggcaggcg gagcttgagg aaaccgcaga taagtttttt tctctttgaa agatagagat    1380
taatacaact acttaaaaaa tatagtcaat aggttactaa gatattgctt agcgttaagt    1440
ttttaacgta atttaatag cttaagattt taagagaaaa tatgaagact agaagagta    1500
gcatgaggaa ggaaaagata aaaggtttct aaaacatgac ggaggttgag atgaagcttc    1560
ttcatggagt aaaaaatgta tttaaaagaa aattgagaga aaggactaca gagccccgaa    1620
ttaataccaa tagaagggca atgctttag attaaaatga aggtgactta aacagcttaa    1680
agtttagttt aaaagttgta ggtgattaaa ataatttgaa ggcgatcttt taaaagaga    1740
ttaaaccgaa ggtgattaaa agaccttgaa atccatgacg cagggagaat tgcgtcattt    1800
aaagcctagt taacgcattt actaaacgca gacgaaaatg gaaagattaa ttgggagtgg    1860
taggatgaaa caatttggag aagatagaag tttgaagtgg aaaactggaa gacagaagta    1920
cgggaaggcg aagaaaagaa tagaagagat agggaaatta aagataaaa acatactttt    1980
agaagaaaaa agataaattt aaacctgaaa agtaggaagc agaagaaaaa agacaagcta    2040
ggaaacaaaa agctaagggc aaaatgtaca aacttagaag aaaattggaa gatagaaaca    2100
agatagaaaa tgaaaatatt gtcaagagtt tcagataaaa aatgaaaaac aagctaagac    2160
aagtattgga gaagtataga agatagaaaa atataaagcc aaaaattgga taaaatagca    2220
ctgaaaaaat gaggaaatta ttggtaacca atttatttta aaagcccatc aatttaattt    2280
ctggtggtgc agaagttaga aggtaaagct tgagaagatg agggtgttta cgtagaccag    2340
```

```
aaccaattta gaagaatact tgaagctaga aggggaagtt ggttaaaaat cacatcaaaa    2400
agctactaaa aggactggtg taatttaaaa aaaactaagg cagaaggctt ttggaagagt    2460
tagaagaatt tggaaggcct taaatatagt agcttagttt gaaaaatgtg aaggactttc    2520
gtaacggaag taattcaaga tcaagagtaa ttaccaactt aatgttttg cattggactt     2580 tgagttaaga ttatttttta aatcctgagg actagcatta attgacagct gacccaggtg    2640
ctacacagaa gtggattcag tgaatctagg aagacagcag cagacaggat tccaggaacc    2700
agtgtttgat gaagctagga ctgaggagca agcgagcaag cagcagttcg tggtgaagat    2760
aggaaaagag tccaggagcc agtgcgattt ggtgaaggaa gctaggaaga aggaaggagc    2820
gctaacgatt tggtggtgaa gctaggaaaa aggattccag gaaggagcga gtgcaatttg    2880
gtgatgaagg tagcaggcgg cttggcttgg caaccacacg gaggaggcga gcaggcgttg    2940
tgcgtagagg atcctagacc agcatgccag tgtgccaagg ccacagggaa agcgagtggt    3000
tggtaaaaat ccgtgaggtc ggcaatatgt tgtttttctg gaacttactt atggtaacct    3060
tttatttatt ttctaatata atgggggagt ttcgtactga ggtgtaaagg gatttatatg    3120
gggacgtagg ccgatttccg ggtgttgtag gtttctcttt ttcaggctta tactcatgaa    3180
tcttgtctga agcttttgag ggcagactgc caagtcctgg agaaatagta gatggcaagt    3240
ttgtgggttt tttttttta cacgaatttg aggaaaacca aatgaatttg atagccaaat    3300
tgagacaatt tcagcaaatc tgtaagcagt ttgtatgttt agttggggta atgaagtatt    3360
tcagttttgt gaatagatga cctgttttta cttcctcacc ctgaattcgt tttgtaaatg    3420
tagagtttgg atgtgtaact gaggcggggg ggagttttca gtattttttt ttgtgggggt    3480
gggggcaaaa tatgttttca gttctttttc ccttaggtct gtctagaatc ctaaaggcaa    3540
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt tccccccac ccccttaatc agactttaaa     3720
agtgcttaac ccccttaaact tgttattttt tacttgaagc attttgggat ggtcttaaca    3780
gggaagagag agggtggggg agaaaatgtt tttttctaag attttccaca gatgctatag    3840
tactattgac aaactgggtt agagaaggag tgtaccgctg tgctgttggc acgaacacct    3900
tcagggactg gagctgcttt tatccttgga agagtattcc cagttgaagc tgaaaagtac    3960
agcacagtgc agctttggtt catattcagt catctcagga gaacttcaga agagcttgag    4020
taggccaaat gttgaagtta agttttccaa taatgtgact tcttaaaagt tttattaaag    4080 gggagggca aatattggca attagttggc agtggcctgt tacggttggg attggtgggg    4140
tgggtttagg taattgttta gtttatgatt gcagataaac tcatgccaga gaacttaaag    4200
tcttagaatg gaaaaagtaa agaaatatca acttccaagt tggcaagtaa ctcccaatga    4260
tttagttttt ttcccccag tttgaattgg gaagctgggg gaagttaaat atgagccact     4320
gggtgtacca gtgcattaat ttgggcaagg aaagtgtcat aatttgatac tgtatctgtt    4380
ttccttcaaa gtatagagct tttggggaag gaaagtattg aactgggggt tggtctggcc    4440
tactgggctg acattaacta caattatggg aaatgcaaaa gttgtttgga tatggtagtg    4500
tgtggttctc ttttggaatt ttttcaggt gatttaataa taatttaaaa ctactataga     4560
aactgcagag caaggaagt ggcttaatga tcctgaaggg atttcttctg atggtagctt     4620
ttgtattatc aagtaagatt ctattttcag ttgtgtgtaa gcaagttttt ttttagtgt     4680 aggagaaata cttttccatt gtttaactgc aaaacaagat gttaaggtat gcttcaaaaa    4740
```

```
ttttgtaaat tgtttatttt aaacttatct gtttgtaaat tgtaactgat taagaattgt   4800
gatagttcag cttgaatgtc tcttagaggg tgggcttttg ttgatgaggg aggggaaact   4860
tttttttttc tatagacttt tttcagataa catcttctga gtcataacca gcctggcagt   4920
atgatggcct agatgcagag aaaacagctc cttggtgaat tgataagtaa aggcagaaaa   4980
gattatatgt catacctcca ttggggaata agcataaccc tgagattctt actactgatg   5040
agaacattat ctgcatatgc caaaaaattt aagcaaatg aaagctacca atttaaagtt    5100
acggaatcta ccatttttaaa gttaattgct tgtcaagcta taaccacaaa aataatgaat  5160
tgatgagaaa tacaatgaag aggcaatgtc catctcaaaa tactgctttt acaaaagcag   5220
aataaaagcg aaagaaaatg aaaatgttac actacattaa tcctggaata aagaagccg    5280 aaaataaatga gagatgagtt gggatcaagt ggattgagga ggctgtgctg tgtgccaatg   5340
tttcgtttgc ctcagacagg tatctcttcg ttatcagaag agttgcttca tttcatctgg   5400
gagcagaaaa cagcaggcag ctgttaacag ataagtttaa cttgcatctg cagtattgca   5460
tgttagggat aagtgcttat ttttaagagc tgtggagttc ttaaatatca accatggcac   5520
tttctcctga cccccttccct aggggatttc aggattgaga aatttttcca tcgagccttt   5580
ttaaaattgt aggacttgtt cctgtgggct tcagtgatgg gatagtacac ttcactcaga   5640
ggcatttgca tctttaaata atttcttaaa agcctctaaa gtgatcagtg ccttgatgcc   5700
aactaaggaa atttgtttag cattgaatct ctgaaggctc tatgaaagga atagcatgat   5760
gtgctgttag aatcagatgt tactgctaaa atttacatgt tgtgatgtaa attgtgtaga   5820
aaaccattaa atcattcaaa ataataaact attttattta gagaatgtat acttttagaa   5880
agctgtctcc ttatttaaat aaaatagtgt ttgtctgtag ttcagtgttg ggcaatcttt   5940
gggggggatt cttctctaat ctttcagaaa ctttgtctgc gaacactctt taatggacca   6000
gatcaggatt tgagcggaag aacgaatgta actttaaggc aggaaagaca aattttattc   6060
ttcataaagt gatgagcata taataattcc aggcacatgg caatagaggc cctctaaata   6120
aggaataaat aacctcttag acaggtggga gattatgatc agagtaaaag gtaattacac   6180
attttatttc cagaaagtca ggggtctata aattgacagt gattagagta atactttttc   6240
acatttccaa agtttgcatg ttaacttttaa atgcttacaa tcttagagtg gtaggcaatg   6300
ttttacacta ttgaccttat ataggaagg gagggggtgc ctgtggggtt ttaaagaatt    6360
ttcctttgca gaggcatttc atccttcatg aagccattca ggattttgaa ttgcatatga   6420
gtgcttggct cttccttctg ttctagtgag tgtatgagac cttgcagtga gtttatcagc   6480
atactcaaaa ttttttttcct ggaatttgga gggatgggag gaggggtgg ggcttacttg    6540 ttgtagcttt ttttttttttt acagacttca cagagaatgc agttgtcttg acttcaggtt   6600
tgtctgttct gttggcaagt aaatgcagta ctgttctgat cccgctgcta ttagaatgca   6660
ttgtgaaacg actggagtat gattaaaagt tgtgttcccc aatgcttgga gtagtgattg   6720
ttgaaggaaa aaatccagct gagtgataaa ggctgagtgt tgaggaaatt tctgcagttt   6780
taagcagtcg tatttgtgat tgaagctgag tacattttgc tggtgtattt ttaggtaaaa   6840 tgcttttttgt tcatttctgg tggtgggagg ggactgaagc ctttagtctt ttccagatgc   6900
aaccttaaaa tcagtgacaa gaaacattcc aaacaagcaa cagtcttcaa gaaattaaac   6960
tggcaagtgg aaatgtttaa acagttcagt gatctttagt gcattgttta tgtgtgggtt   7020
tctctctccc ctcccttggt cttaattctt acatgcagga acactcagca gacacacgta   7080
```

| | |
|---|---|
| tgcgaagggc cagagaagcc agacccagta agaaaaaata gcctatttac tttaaataaa | 7140 |
| ccaaacattc cattttaaat gtggggattg ggaaccacta gttcttttcag atggtattct | 7200 |
| tcagactata gaaggagctt ccagttgaat tcaccagtgg acaaaatgag gaaaacaggt | 7260 |
| gaacaagctt tttctgtatt tacatacaaa gtcagatcag ttatgggaca atagtattga | 7320 |
| atagatttca gctttatgct ggagtaactg gcatgtgagc aaactgtgtt ggcgtggggg | 7380 |
| tggagggggtg aggtgggcgc taagcctttt tttaagatttt ttcaggtacc cctcactaaa | 7440 |
| ggcaccgaag gcttaaagta ggacaaccat ggagccttcc tgtggcagga gagacaacaa | 7500 |
| agcgctatta tcctaaggtc aagagaagtg tcagcctcac ctgatttttta ttagtaatga | 7560 |
| ggacttgcct caactccctc tttctggagt gaagcatccg aaggaatgct tgaagtaccc | 7620 |
| ctgggcttct cttaacattt aagcaagctg ttttttatagc agctcttaat aataaagccc | 7680 |
| aaatctcaag cggtgcttga aggggaggga aaggggggaaa gcggcaacc acttttccct | 7740 |
| agcttttcca gaagcctgtt aaaagcaagg tctccccaca agcaacttct ctgccacatc | 7800 |
| gccaccccgt gccttttgat ctagcacaga cccttcaccc ctcacctcga tgcagccagt | 7860 |
| agcttggatc cttgtgggca tgatccataa tcggtttcaa ggtaacgatg gtgtcgaggt | 7920 |
| cttttggtggg ttgaactatg ttagaaaagg ccattaattt gcctgcaaat tgttaacaga | 7980 |
| agggtattaa aaccacagct aagtagctct attataatac ttatccagtg actaaaacca | 8040 |
| acttaaacca gtaagtggag aaataacatg ttcaagaact gtaatgctgg gtgggaacat | 8100 |
| gtaacttgta gactggagaa gataggcatt tgagtggctg agagggcttt tgggtgggaa | 8160 |
| tgcaaaaatt ctctgctaag acttttttcag gtgaacataa cagacttggc caagctagca | 8220 |
| tcttagcgga agctgatctc caatgctctt cagtagggtc atgaaggttt ttcttttcct | 8280 |
| gagaaaacaa cacgtattgt tttctcaggt tttgcttttt ggccttttttc tagcttaaaa | 8340 |
| aaaaaaaaag caaaagatgc tggtggttgg cactcctggt ttccaggacg gggttcaaat | 8400 |
| ccctgcggcg tctttgcttt gactactaat ctgtcttcag gactcttttct gtatttctcc | 8460 |
| ttttctctgc aggtgctagt tcttggagtt ttggggaggt gggaggtaac agcacaatat | 8520 |
| ctttgaacta tatacatcct tgatgtataa tttgtcagga gcttgacttg attgtatatt | 8580 |
| catatttaca cgagaaccta atataactgc cttgtctttt tcaggtaata gcctgcagct | 8640 |
| ggtgttttga gaagccctac tgctgaaaac ttaacaattt tgtgtaataa aaatggagaa | 8700 |
| gctctaaa | 8708 |

<210> SEQ ID NO 10
<211> LENGTH: 6982
<212> TYPE: DNA
<213> ORGANISM: Mus musculus

<400> SEQUENCE: 10

| | |
|---|---|
| aggcattcag gcagcgagag cagagcagcg tagagcagca cagctgagct cgtgaggcag | 60 |
| gagactcagc ccgaggaaat cgcagataag tttttaatta aaaagattga gcagtaaaaa | 120 |
| gaattagaac tctaaactta agctaataga gtagcttatc gaaatattac ttagtcttaa | 180 |
| taatctaaga agatcttaag agataacatg aaggcttatt taaacagttt gaaaaaggaa | 240 |
| atgaggagaa aagtatttgt actgtataat ggaggctgac cagagcagtt taggagattg | 300 |
| taaagggagg ttttgtgaag ttctaaaagg ttctagtttg aaggtcggcc ttgtagatta | 360 |
| aaacgaaggt tacctaaaata gaatctaagt ggcatttaaa acagtaaagt tgtagagaat | 420 |
| agtttgaaaa tgaggtgtag ttttaaaaga ttgagaaaag taggttaagt tgacggccgt | 480 |

-continued

```
tataaaaatc cttcgactgg cgcatgtacg tttgaaggca tgagttggaa acagggaaga    540
tggaagtgtt aggctagccg ggcgatggtg gcgcacgcct ttaatcctag cacttgggag    600
gcagaggcag gcggatttct gagttcgagg ccagcctggt ctacagagtg agttccagga    660
cagccagggc tacacagaga aaccctgtct tgaaaaaaca aaaaggttag gctagtattt    720
ggagaaagaa gattagaaaa tggaagtgaa agacgaagaa gacatacagg aaggtgaaga    780
aaaagctgtt agagaagata ggaaaataga agacaaagca tctttagaag acagaaaagg    840
tacttaaagg cacaggtagt aggaagccga agaatagaag atagaaagaa gcaagataga    900
aaaacaaaat ggaagttaag acaactttgg atgccagcat tcaagatagg caagaagat     960 aagattgagg ccaaaaggtt ggataagata taaagtcaga aggaaattat ctttaaagcc   1020
ataagttcaa atttctgatg gagcgagcag tttagaagag tctttagaca gccacataca   1080
agattgaagc tagcaatcaa agctactagg actgaagtaa aaagttaagg cagaatgcct   1140
ttgaagagtt agaagaatat taaaagcctt aacttgtagc ttaattttgc ttgatgacaa   1200
aaggactttt gataacagtt tcaagattgt cagcattttg cattggactt gagctgaggt   1260
gcttttaaaa tcctaacgac tagcattggc agctgaccca ggtctacaca gaagtgcatt   1320
cagtgaacta ggaagacagg agcggcagac aggagtcccg aagccagttt ggtgaagcta   1380
ggaaggactg aggagccagc agcagcagtg catggtgaag atagcccagg aaagagtgcg   1440
gttcggtgga ggaagctagg aagaaggagc catacggatg tggtggtgaa gctgggaaag   1500
ggttccagga tggtggagcg agagcgagtt ggtgatgaag ctagctggcg gcttggcttg   1560
tcaactgcgc ggaggaggcg agcaggcatt gtggagagga tagatagcgg ctcctagacc   1620
agcatgccag tgtgcaagaa aggctgcagg gagagcatgc ggtgcggtaa cattccttga   1680
ggtcggcaac atggtggtgg ttttctgtaa cttggatggt aacttgttta ctttgtctta   1740
atagttatgg gggagttgta ggcttctgtg taaagagata tatctggggc tgtatgtagg   1800
cctttgcggg tgttgtaggt ttttcttttt cagggttatg tcctcttgca tcttgtcaga   1860 agctttgag ggctgactgc caaggcccag aaagaagaat ggtagatggc aagttgtctt   1920
taaccgctca gagggaatg aatggtagag ccagcacaac ctcccagttt tgtaagacgt   1980
tgtagtttga acagatgacc taccacaagc ctcactcctg tgtagggag gtaattgggc    2040 aaagtgcttt tggggaatg ggggcaaaat atattttgag ttcttttccc cttaggtctg    2100
tctagaatcc taaaggcaga tgactcaagg gaaccagaaa aaaggaaatc cactctcagg   2160
ataagcagag ctcgccaggt ttacagtttg taggaagtag aggatggatg ctagctttca   2220
cactgagtgt ggaggagctg gccatggcgg aattgctggt agtttactct ttccccctcc    2280
cttaatgaga tttgtaaaat cctaaacact tttacttgaa atatttggga gtggtcttaa   2340
cagggaggag tgggtggggg aaacgttttt tttctaagat tttccacaga tgctatagtt   2400
gtgttgacac actgggttag agaaggcgtg tactgctatg ctgttggcac gacaccttca   2460
gggactggag ctgccttttg tccttggaag agttttccca gttgccgctg aagtcagcac   2520
agtgcggctt tggttcacag tcacctcagg agaacctcag gagcttggct aggccagagg   2580
ttgaagttaa gttttacagc accgtgattt aaaatatttc attaagggg agggtaaaa    2640 cttagttggc tgtggccttg tgtttgggtg gtgggggtg ttaggtaatt gtttagttta    2700
tgatttcaga taatcatacc agagaactta aatatttgga aaaacaggaa atctcagctt   2760
tcaagttggc aagtaactcc caatccagtt tttgcttctt ttttcctttt tcttttttg    2820
```

-continued

```
aggcgggcag ctaaggaagg ttggttcctc tgccggtccc tcgaaagcgt agggcttggg     2880
ggttggtctg gtccactggg atgatgtgat gctacagtgg ggactcttct gaagctgttg     2940
gatgaatata gattgtagtg tgtggttctc ttttgaaatt ttttttcaggt gacttaatgt    3000 atcttaataa ctactatagg aacaaaggaa gtggctttaa tgaccctgaa ggaatttctt     3060
ctggtgatag ctttttatatt atcaagtaag agatactatc tcagttttgt ataagcaagt    3120 cttttttccta gtgtaggaga aatgattttc cttgtgacta acaagatgt aaaggtatgc     3180 ttttttttctt cttgtgcatt gtatacttgt gtttatttgt aacttataat ttaagaatta   3240
tgataattca gcctgaatgt cttttagagg gtgggctttt gttgatgagg gaggggaaac    3300 ctttttttttt ctgtagacct ttttcagata acaccatctg agtcataacc agcctggcag   3360
tgtgatgacg tagatgcaga gggagcagct ccttggtgaa tgagtgataa gtaaaggcag    3420
aaaaaataat gtcatgtctc catggggaat gagcatgagc cagagattgt tcctactgat    3480
gaaaagctgc atatgcaaaa atttaagcaa atgaaagcaa ccagtataaa gttatggcaa    3540
tacctttaaa agttatggct tatctaccaa gctttatcca caaaagtaaa gaattgatga    3600
aaaacagtga agatcaaatg ttcatctcaa aactgctttt acaaaagcag aatagaaatg    3660
aagtgaaaat gctgcattaa gcctggagta aaaagaagct gagcttgttg agatgagtgg    3720
gatcgagcgg ctgcgaggcg gtgcagtgtg ccaatgtttc gtttgcctca gacaggtttc    3780
tcttcataag cagaagagtt gcttcattcc atctcggagc aggaaacagc agactgctgt    3840
tgacagataa gtgtaacttg gatctgcagt attgcatgtt agggatagat aagtgccttt    3900
tttctctttt tccaaaaaga cctgtagagc tgttgaatgt ttgcagctgg cccctcttag    3960
gcagttcaga attttgagta gttttcccat ccagcctctt aaaaattcct aagccttgca    4020
ccgatgggct ttcatgatgg gatagctaat aggcttttgc atcgtaaact tcaacacaaa    4080
agcctacatg attaatgcct actttaatta cattgcttac aagattaagg aatctttatc    4140
ttgaagaccc catgaaaggg atcattatgt gctgaaaatt agatgttcat attgctaaaa    4200
tttaaatgtg ctccaatgta cttgtgctta aaatcattaa attatacaaa ttaataaaat    4260
acttcactag agaatgtatg tatttagaag gctgtctcct tatttaaata agtcttgtt    4320 tgttgtctgt agttagtgtg ggcaattttg gggggatgtt cttctctaat cttttcagaa    4380
acttgacttc gaacacttaa gtggaccaga tcaggatttg agccagaaga ccgaaattaa    4440
ctttaaggca ggaaagacaa attttattct ccatgcagtg atgagcattt ataaattgca   4500
ggcctggcat agaggccgtc taactaagga ctaagtacct taggcaggtg ggagatgatg    4560
gtcagagtaa aaggtaacta catattttgt ttccagaaag tcagggtct aatttgacca     4620 tggctaaaca tctagggtaa gacacttttc ccccacattt ccaaatatgc atgttgagtt    4680
taaatgctta cgatcatctc atccacttta gccttttgtc acctcacttg agccacgagt    4740
ggggtcaggc atgtgggttt aaagagtttt ccttttgcaga gcctcatttc atccttcatg   4800
gagctgctca ggactttgca tataagcgct tgcctctgtc ttctgttctg ctagtgagtg    4860
tgtgatgtga gaccttgcag tgagtttgtt tttcctggaa tgtggaggga gggggggatg    4920
gggcttactt gttctagctt tttttttaca gaccacacag aatgcaggtg tcttgacttc    4980
aggtcatgtc tgttctttgg caagtaatat gtgcagtact gttccaatct gctgctatta    5040
gaatgcattg tgacgcgact ggagtatgat taaagaaagt tgtgtttccc caagtgtttg    5100
gagtagtggt tgtggagga aaagccatga gtaacaggct gagtgttgag gaaatggctc    5160
tctgcagctt taagtaaccc gtgtttgtga ttggagccga gtcccttttgc tgtgctgcct   5220
```

| | |
|---|---|
| taggtaaatg tttttgttca tttctggtga gggggggttgg gagcactgaa gcctttagtc | 5280 |
| tcttccagat tcaacttaaa atctgacaag aaataaatca gacaagcaac attcttgaag | 5340 |
| aaattttaac tggcaagtgg aaatgttttg aacagttccg tggtctttag tgcattatct | 5400 |
| ttgtgtaggt gttctctctc ccctcccttg gtcttaattc ttacatgcag gaacattgac | 5460 |
| aacagcagac atctatctat tcaaggggcc agagaatcca gacccagtaa ggaaaaatag | 5520 |
| cccatttact ttaaatcgat aagtgaagca gacatgccat tttcagtgtg gggattggga | 5580 |
| agccctagtt ctttcagatg tacttcagac tgtagaagga gcttccagtt gaattgaaat | 5640 |
| tcaccagtgg acaaaatgag gacaacaggt gaacgagcct tttcttgttt aagattagct | 5700 |
| actggtaatc tagtgttgaa tcctctccag cttcatgctg gagcagctag catgtgatgt | 5760 |
| aatgttggcc ttggggtgga ggggtgaggt gggcgctaag cctttttta agattttca | 5820 |
| ggtacccctc actaaaggca ctgaaggctt aatgtaggac agcggagcct tcctgtgtgg | 5880 |
| caagaatcaa gcaagcagta ttgtatcgag accaaagtgg tatcatggtc ggttttgatt | 5940 |
| agcagtgggg actaccctac cgtaacacct tgttggaatt gaagcatcca agaaaatac | 6000 |
| ttgagaggcc ctgggcttgt tttaacatct ggaaaaaagg ctgttttat agcagcggtt | 6060 |
| accagcccaa acctcaagtt gtgcttgcag gggagggaaa aggggggaaag cgggcaacca | 6120 |
| gtttccccag ctttttccaga atcctgttac aaggtctccc cacaagtgat ttctctgcca | 6180 |
| catcgccacc atgggccttt ggcctaatca cagacccttc acccctcacc ttgatgcagc | 6240 |
| cagtagctgg atccttgagg tcacgttgca tatcggtttc aaggtaacca tggtgccaag | 6300 |
| gtcctgtggg ttgcaccaga aaaggccatc aatttccccc ttgcctgtaa tttaacatta | 6360 |
| aaaccatagc taagatgttt tatacatagc acctatgcag agtaaacaaa ccagtatggg | 6420 |
| tatagtatgt ttgataccag tgctgggtgg gaatgtagga agtcggatga aaagcaagcc | 6480 |
| tttgtaggaa gttgttgggg tgggattgca aaaattctct gctaagactt tttcaggtgg | 6540 |
| acataacaga cttggccaag ctagcatctt agtggaagca gattcgtcag tagggttgta | 6600 |
| aaggtttttc ttttcctgag aaaacaacct tttgtttttct caggttttgc ttttttggcct | 6660 |
| ttccctagct ttaaaaaaaa aaaagcaaaa gacgctggtg gctggcactc ctggtttcca | 6720 |
| ggacggggtt caagtccctg cggtgtcttt gcttgactct tatatcatga ggccattaca | 6780 |
| ttttttcttgg agggttctaa aggctctggg tatggtagct gatatcactg gaacactccc | 6840 |
| cagcctcagt gttgaactct tgataattaa ctgcattgtc tttcaggtta tgcccaattc | 6900 |
| gtcttattac ctctgagtcg acacacctcc tactatttat tgaatacttt gattttatga | 6960 |
| aataaaaact aaatatctct ca | 6982 |

<210> SEQ ID NO 11
<211> LENGTH: 6689
<212> TYPE: DNA
<213> ORGANISM: Mus musculus

<400> SEQUENCE: 11

| | |
|---|---|
| aggcattcag gcagcgagag cagagcagcg tagagcagca cagctgagct cgtgaggcag | 60 |
| gagactcagc ccgaggaaat cgcagataag ttttaatta aaaagattga gcagtaaaaa | 120 |
| gaattagaac tctaaactta agctaataga gtagcttatg aaatattact tagtcttaat | 180 |
| aatctaagaa gatcttaaga gataacatga aggcttattt aaacagtttg aaaaaggaaa | 240 |
| tgaggagaaa agtatttgta ctgtataatg gaggctgacc agagcagttt aggagattgt | 300 |

```
aaagggaggt tttgtgaagt tctaaaaggt tctagtttga aggtcggcct tgtagattaa    360
aacgaaggtt acctaaatag aatctaagtg gcatttaaaa cagtaaagtt gtagagaata    420
gtttgaaaat gaggtgtagt tttaaaagat tgagaaaagt aggttaagtt gacggccgtt    480
ataaaaatcc ttcgactggc gcatgtacgt ttgaaggcat gagttggaaa cagggaagat    540
ggaagtgtta ggctagccgg gcgatggtgg cgcacgcctt taatcctagc acttgggagg    600
cagaggcagg cggatttctg agttcgaggc cagcctggtc tacagagtga gttccaggac    660
agccagggct acacagagaa accctgtctt gaaaaaacaa aaaggttagg ctagtatttg    720
gagaaagaag attagaaaat ggaagtgaaa gacgaagaag acatacagga aggtgaagaa    780
aaagctgtta gagaagatag gaaaatagaa gacaaagcat ctttagaaga cagaaaaggt    840
acttaaaggc acaggtagta ggaagccgaa gaatagaaga tagaaagaag caagatagaa    900
aaacaaaatg gaagttaaga caactttgga tgccagcatt caagataggc aaagaagata    960
agattgaggc caaaaggttg gataagatat aaagtcagaa ggaaattatc tttaaagcca   1020
taagttcaaa tttctgatgg agcgagcagt ttagaagagt ctttagacag ccacatacaa   1080
gattgaagct agcaatcaaa gctactagga ctgaagtaaa aagttaaggc agaatgcctt   1140
tgaagagtta gaagaatatt aaaagcctta acttgtagct taattttgct tgatgacaaa   1200
aggactttg ataacagttt caagattgtc agcattttgc attggacttg agctgaggtg   1260
cttttaaaat cctaacgact agcattggca gctgacccag gtctacacag aagtgcattc   1320
agtgaactag gaagacagga gcggcagaca ggagtcccga agccagtttg gtgaagctag   1380
gaaggactga ggagccagca gcagcagtgc atggtgaaga tagcccagga aagagtgcgg   1440
ttcggtggag gaagctagga agaaggagcc atacggatgt ggtggtgaag ctgggaaagg   1500
gttccaggat ggtggagcga gagcgagttg gtgatgaagc tagctggcgg cttggcttgt   1560
caactgcgcg gaggaggcga gcaggcattg tggagaggat agatagcggc tcctagacca   1620
gcatgccagt gtgcaagaaa ggctgcaggg agagcatgcg gtgcggtaac attccttgag   1680
gtcggcaaca tggtggtggt tttctgtaac ttggatggta acttgtttac tttgtcttaa   1740
tagttatggg ggagttgtag gcttctgtgt aaagagatat atctggggct gtatgtaggc   1800
cttttgcgggt gttgtaggtt tttctttttc agggttatgt cctcttgcat cttgtcagaa   1860
gcttttgagg gctgactgcc aaggcccaga aagaagaatg gtagatggca agttgtcttt   1920
aaccgctcag aggggaatga atggtagagc cagcacaacc tcccagtttt gtaagacgtt   1980
gtagtttgaa cagatgacct accacaagcc tcactcctgt gtaggggagg taattgggca   2040
aagtgctttt gggggaatgg gggcaaaata tattttgagt tcttttcccc ttaggtctgt   2100
ctagaatcct aaaggcagat gactcaaggg aaccagaaaa aaggaaatcc actctcagga   2160
taagcagagc tcgccaggtt tacagtttgt aggaagtaga ggatggatgc tagcttttcac  2220
actgagtgtg gaggagctgg ccatggcgga attgctggta gtttactctt tccccctccc   2280
ttaatgagat ttgtaaaatc ctaaacactt ttacttgaaa tatttgggag tggtcttaac   2340
agggaggagt gggtggggga aacgtttttt ttctaagatt ttccacagat gctatagttg   2400
tgttgacaca ctgggttaga gaaggcgtgt actgctatgc tgttggcacg acacctttcag  2460
ggactggagc tgccttttgt ccttggaaga gttttcccag ttgccgctga agtcagcaca   2520
gtgcggcttt ggttcacagt cacctcagga gaacctcagg agcttggcta ggccagaggt   2580
tgaagttaag ttttacagca ccgtgattta aaatatttca ttaaagggga ggggtaaaac   2640
ttagttggct gtggccttgt gtttgggtgg gtggggtgt taggtaattg tttagtttat    2700
```

```
gatttcagat aatcatacca gagaacttaa atatttggaa aaacaggaaa tctcagcttt    2760
caagttggca agtaactccc aatccagttt ttgcttcttt tttcctttt ctttttttga    2820 ggcgggcagc taaggaaggt tggttcctct gccggtccct cgaaagcgta gggcttgggg    2880
gttggtctgg tccactggga tgatgtgatg ctacagtggg gactcttctg aagctgttgg    2940
atgaatatag attgtagtgt gtggttctct tttgaaattt ttttcaggtg acttaatgta    3000
tcttaataac tactatagga acaaggaag tggctttaat gaccctgaag gaatttcttc    3060
tggtgatagc ttttatatta tcaagtaaga gatactatct cagttttgta taagcaagtc    3120 ttttttcctag tgtaggagaa atgatttttcc ttgtgactaa acaagatgta aaggtatgct    3180
ttttttcttc ttgtgcattg tatacttgtg tttatttgta acttataatt taagaattat    3240
gataattcag cctgaatgtc ttttagaggg tgggcttttg ttgatgaggg aggggaaacc    3300
tttttttttc tgtagacctt tttcagataa caccatctga gtcataacca gcctggcagt    3360
gtgatgacgt agatgcagag ggagcagctc cttggtgaat gagtgataag taaaggcaga    3420
aaaaataatg tcatgtctcc atggggaatg agcatgagcc agagattgtt cctactgatg    3480
aaaagctgca tatgcaaaaa tttaagcaaa tgaaagcaac cagtataaag ttatggcaat    3540
acctttaaaa gttatggctt atctaccaag ctttatccac aaaagtaaag aattgatgaa    3600
aaacagtgaa gatcaaatgt tcatctcaaa actgctttta caaaagcaga atagaaatga    3660
agtgaaaatg ctgcattaag cctggagtaa aaagaagctg agcttgttga gatgagtggg    3720
atcgagcggc tgcgaggcgg tgcagtgtgc caatgtttcg tttgcctcag acaggtttct    3780
cttcataagc agaagagttg cttcattcca tctcggagca ggaaacagca gactgctgtt    3840
gacagataag tgtaacttgg atctgcagta ttgcatgtta gggatagata agtgccttt    3900 ttctctttt ccaaaaagac ctgtagagct gttgaatgtt tgcagctggc ccctcttagg    3960
cagttcagaa ttttgagtag ttttcccatc cagcctctta aaaattccta agccttgcac    4020
cgatgggctt tcatgatggg atagctaata ggcttttgca tcgtaaactt caacacaaaa    4080
gcctacatga ttaatgccta ctttaattac attgcttaca agattaagga atctttatct    4140
tgaagacccc atgaaaggga tcattatgtg ctgaaaatta gatgttcata ttgctaaaat    4200
ttaaatgtgc tccaatgtac ttgtgcttaa aatcattaaa ttatacaaat taataaaata    4260
cttcactaga gaatgtatgt atttagaagg ctgtctcctt atttaaataa agtcttgttt    4320
gttgtctgta gttagtgtgg gcaattttgg ggggatgttc ttctctaatc ttttcagaaa    4380
cttgacttcg aacacttaag tggaccagat caggatttga gccagaagac cgaaattaac    4440
tttaaggcag gaaagacaaa ttttattctc catgcagtga tgagcattta ataattgcag    4500
gcctggcata gaggccgtct aactaaggac taagtacctt aggcaggtgg gagatgatgg    4560
tcagagtaaa aggtaactac atattttgtt tccagaaagt caggggtcta atttgaccat    4620
ggctaaacat ctagggtaag acacttttcc cccacatttc caaatatgca tgttgagttt    4680
aaatgcttac gatcatctca tccactttag ccttttgtca cctcacttga gccacgagtg    4740
gggtcaggca tgtgggttta aagagttttc ctttgcagag cctcatttca tccttcatgg    4800
agctgctcag gactttgcat ataagcgctt gcctctgtct tctgttctgc tagtgagtgt    4860
gtgatgtgag accttgcagt gagtttgttt ttcctggaat gtggagggag gggggatgg    4920 ggcttacttg ttctagcttt tttttttacag accacacaga atgcaggtgt cttgacttca    4980
ggtcatgtct gttctttggc aagtaatatg tgcagtactg ttccaatctg ctgctattag    5040
```

| | |
|---|---|
| aatgcattgt gacgcgactg gagtatgatt aaagaaagtt gtgtttcccc aagtgtttgg | 5100 |
| agtagtggtt gttggaggaa aagccatgag taacaggctg agtgttgagg aaatggctct | 5160 |
| ctgcagcttt aagtaacccg tgtttgtgat tggagccgag tccctttgct gtgctgcctt | 5220 |
| aggtaaatgt ttttgttcat ttctggtgag ggggggttggg agcactgaag cctttagtct | 5280 |
| cttccagatt caacttaaaa tctgacaaga ataaatcag acaagcaaca ttcttgaaga | 5340 |
| aattttaact ggcaagtgga aatgttttga acagttccgt ggtctttagt gcattatctt | 5400 |
| tgtgtaggtg ttctctctcc cctcccttgg tcttaattct tacatgcagg aacattgaca | 5460 |
| acagcagaca tctatctatt caaggggcca gagaatccag acccagtaag gaaaaatagc | 5520 |
| ccatttactt taaatcgata agtgaagcag acatgccatt ttcagtgtgg ggattgggaa | 5580 |
| gccctagttc tttcagatgt acttcagact gtagaaggag cttccagttg aattgaaatt | 5640 |
| caccagtgga caaaatgagg acaacaggtg aacgagcctt ttcttgttta agattagcta | 5700 |
| ctggtaatct agtgttgaat cctctccagc ttcatgctgg agcagctagc atgtgatgta | 5760 |
| atgttggcct tggggtggag gggtgaggtg ggcgctaagc cttttttttaa gattttttcag | 5820 |
| gtaccccctca ctaaaggcac tgaaggctta atgtaggaca gcggagcctt cctgtgtggc | 5880 |
| aagaatcaag caagcagtat tgtatcgaga ccaaagtggt atcatggtcg gttttgatta | 5940 |
| gcagtgggga ctaccctacc gtaacaccctt gttggaattg aagcatccaa agaaaatact | 6000 |
| tgagaggccc tgggcttgtt ttaacatctg gaaaaaggc tgttttttata gcagcggtta | 6060 |
| ccagcccaaa cctcaagttg tgcttgcagg ggagggaaaa ggggggaaagc gggcaaccag | 6120 |
| tttccccagc ttttccagaa tcctgttaca aggtctcccc acaagtgatt tctctgccac | 6180 |
| atcgccacca tgggcctttg gcctaatcac agacccttca cccctcacct tgatgcagcc | 6240 |
| agtagctgga tccttgaggt cacgttgcat atcggtttca aggtaaccat ggtgccaagg | 6300 |
| tcctgtgggt tgcaccagaa aaggccatca atttcccct tgcctgtaat ttaacattaa | 6360 |
| aaccatagct aagatgtttt atacatagca cctatgcaga gtaaacaaac cagtatgggt | 6420 |
| atagtatgtt tgataccagt gctgggtggg aatgtaggaa gtcggatgaa aagcaagcct | 6480 |
| ttgtaggaag ttgttggggt gggattgcaa aaattctctg ctaagacttt ttcaggtgga | 6540 |
| cataacagac ttggccaagc tagcatctta gtggaagcag attcgtcagt agggttgtaa | 6600 |
| aggtttttct tttcctgaga aaacaacctt ttgttttctc aggttttgct ttttggcctt | 6660 |
| tccctagctt taaaaaaaaa aaagcaaaa | 6689 |

<210> SEQ ID NO 12
<211> LENGTH: 10001
<212> TYPE: DNA
<213> ORGANISM: Mus musculus

<400> SEQUENCE: 12

| | |
|---|---|
| tgactatcag cctgtatggt cattaagttc tgtctaccct gggaaagcct ctgcccaaac | 60 |
| ctccctattc acaggtccta gaacgtagag gtggggagca ggacggtgcc gccaggccgt | 120 |
| gtgcgatcgc gagctctgga tctcaatgcg ccccggggcg ctgtttccca cgactccagc | 180 |
| agcttttcta aaaatccagg cagcctccag tttacgggat caacccgaga ctcgcttccc | 240 |
| tttgaaaatt ctagagtata agtaaacgt acgagcaaag tatgtgtctt aacacttaat | 300 |
| ggatgacata gagaccaaaa aagccatgtc cgtgggccca gtaggccgca ataagggggcg | 360 |
| accaggaaac tgcagcacag cccccccgcag ccgccctgct cccacaccag tcattccagc | 420 |
| accgtggtga aggcgcttgg gggcggggcg gggcgcgcct gcgcagcgag gctctgcagc | 480 |

```
agaaactttg cctagaccgg ctggaaccgg ttagaaccgg tcgaacccgg ccggctgcca    540
gccctcgatt cagcagctca caaagggagg cggcgactca cgacccgcgt atccttgcgc    600
ctctccccac cccctttgtc ctcgcgacgg gttccgcggt cctccccgcc ctccctggcg    660
cggccccgc tttctgcgcc cagtgacgct ttctccatgg tcctgggaga aagagaaaaa    720
catccttcc cctccgtcgt agttttagga agcgatgaga tagacctggg gaccttgccg    780
ccacgggccg ggctctgacg gttattagcg cagtgcgggt ggtgctcggc atggccgcca    840
aggtcgccgt gccctcacct gcagcgacca tggccttgct gggctgagac cgcagcctaa    900
catggcggac gtaggcaagc accaaagcgc tcgtgtaccc gggctcggaa aagtggcccc    960
gagagcagcc ggaggctgca ggtcgtccct acaggagcat tcccagtata aaccagtaca   1020
aagtgtcacc acctcagaag ccactcgcag ggccggtcac tttccgagag acctccatct   1080
tgtttcgcat gaaatggcag ccgctcgggg agttacaaaa tgggaagtgg aagctgaagc   1140
tgtgggaaag cctgttttaa cacttgcaac atacgctata ccctctgtcc tcccaggaaa   1200
acgcaaaagg tgttgaaaca tctgaaaaac ttggggctcc cattttaat agctattagt    1260
tcatgttttt tctccttgtg accagaaatt ttaaacctat ttgtacctat ttagctggta   1320
caagctaaac atttctctgt attagcaagg tccaagaggc ccacacgacg tcaagaaaaa   1380
tctagaaact tggaagtcag gatctatttt taactctctg aggaactatt tttcttcctt   1440
caccaaggtg gtggagggtt actaggttcc ggtggagtga cgtgtccctt tgcaataaat   1500
accggcgctc cgggctctgc gtcaggcatt caggcagcga gagcagagca gcgtagagca   1560
gcacagctga gctcgtgagg caggagactc agcccgagga aatcgcagat aagtttttaa   1620
ttaaaaagat tgagcagtaa aaagaattag aactctaaac ttaagctaat agagtagctt   1680
atcgaaatat tacttagtct taataatcta agaagatctt aagagataac atgaaggctt   1740
atttaaacag tttgaaaaag gaaatgagga gaaaagtatt tgtactgtat aatggaggct   1800
gaccagagca gtttaggaga ttgtaaaggg aggttttgtg aagttctaaa aggttctagt   1860
ttgaaggtcg gccttgtaga ttaaaacgaa ggttacctaa atagaatcta agtggcattt   1920
aaaacagtaa agttgtagag aatagtttga aaatgaggtg tagttttaaa agattgagaa   1980
aagtaggtta agttgacggc cgttataaaa atccttcgac tggcgcatgt acgtttgaag   2040
gcatgagttg gaaacaggga agatggaagt gttaggctag ccgggcgatg gtggcgcacg   2100
cctttaatcc tagcacttgg gaggcagagg caggcggatt tctgagttcg aggccagcct   2160
ggtctacaga gtgagttcca ggacagccag ggctacacag agaaaccctg tcttgaaaaa   2220
acaaaaggt taggctagta tttggagaaa gaagattaga aaatggaagt gaaagacgaa   2280
gaagacatac aggaaggtga agaaaaagct gttagagaag ataggaaaat agaagacaaa   2340
gcatctttag aagacagaaa aggtacttaa aggcacaggt agtaggaagc cgaagaatag   2400
aagatagaaa gaagcaagat agaaaaacaa aatggaagtt aagacaactt tggatgccag   2460
cattcaagat aggcaaagaa gataagattg aggccaaaag gttggataag atataaagtc   2520
agaaggaaat tatctttaaa gccataagtt caaatttctg atggagcgag cagtttagaa   2580
gagtctttag acagccacat acaagattga agctagcaat caaagctact aggactgaag   2640
taaaaagtta aggcagaatg cctttgaaga gttagaagaa tattaaaagc cttaacttgt   2700
agcttaattt tgcttgatga caaaaggact tttgataaca gtttcaagat tgtcagcatt   2760
ttgcattgga cttgagctga ggtgctttta aaatcctaac gactagcatt ggcagctgac   2820
```

```
ccaggtctac acagaagtgc attcagtgaa ctaggaagac aggagcggca gacaggagtc    2880
ccgaagccag tttggtgaag ctaggaagga ctgaggagcc agcagcagca gtgcatggtg    2940
aagatagccc aggaaagagt gcggttcggt ggaggaagct aggaagaagg agccatacgg    3000
atgtggtggt gaagctggga aagggttcca ggatggtgga gcgagagcga gttggtgatg    3060
aagctagctg gcggcttggc ttgtcaactg cgcggaggag gcgagcaggc attgtggaga    3120
ggatagatag cggctcctag accagcatgc cagtgtgcaa gaaaggctgc agggagagca    3180
tgcggtgcgg taacattcct tgaggtcggc aacatggtgg tggttttctg taacttggat    3240
ggtaacttgt ttactttgtc ttaatagtta tgggggagtt gtaggcttct gtgtaaagag    3300
atatatctgg ggctgtatgt aggcctttgc gggtgttgta ggttttttctt tttcagggtt    3360
atgtcctctt gcatcttgtc agaagctttt gagggctgac tgccaaggcc agaaagaaag    3420
aatggtagat ggcaagttgt ctttaaccgc tcagagggga atgaatggta gagccagcac    3480
aacctcccag ttttgtaaga cgttgtagtt tgaacagatg acctaccaca agcctcactc    3540
ctgtgtaggg gaggtaattg ggcaaagtgc ttttggggga atgggggcaa aatatatttt    3600
gagttctttt ccccttaggt ctgtctagaa tcctaaaggc agatgactca agggaaccag    3660
aaaaaaggaa atccactctc aggataagca gagctcgcca ggtttacagt ttgtaggaag    3720
tagaggatgg atgctagctt tcacactgag tgtggaggag ctggccatgg cggaattgct    3780
ggtagtttac tctttccccc tcccttaatg agatttgtaa aatcctaaac acttttactt    3840
gaaatatttg ggagtggtct taacagggag gagtgggtgg gggaaacgtt ttttttctaa    3900
gattttccac agatgctata gttgtgttga cacactgggt tagagaaggc gtgtactgct    3960
atgctgttgg cacgacacct tcagggactg gagctgcctt ttgtccttgg aagagttttc    4020
ccagttgccg ctgaagtcag cacagtgcgg ctttggttca cagtcacctc aggagaacct    4080
caggagcttg gctaggccag aggttgaagt taagttttac agcaccgtga tttaaaatat    4140
ttcattaaag gggagggta aaacttagtt ggctgtggcc ttgtgtttgg gtgggtgggg    4200
gtgttaggta attgtttagt ttatgatttc agataatcat accagagaac ttaaatatt    4260
ggaaaaacag gaaatctcag cttttcaagtt ggcaagtaac tcccaatcca gtttttgctt    4320
cttttttcct ttttctttttt ttgaggcggg cagctaagga aggttggttc ctctgccggt    4380
ccctcgaaag cgtagggctt gggggttggt ctggtccact gggatgatgt gatgctacag    4440
tggggactct tctgaagctg ttggatgaat atagattgta gtgtgtggtt ctcttttgaa    4500
attttttca ggtgacttaa tgtatcttaa taactactat aggaacaaag gaagtggctt    4560
taatgaccct gaaggaattt cttctggtga tagcttttat attatcaagt aagagatact    4620
atctcagttt tgtataagca agtctttttc ctagtgtagg agaaatgatt ttccttgtga    4680
ctaaacaaga tgtaaaggta tgctttttt cttcttgtgc attgtatact tgtgtttatt    4740
tgtaacttat aatttaagaa ttatgataat tcagcctgaa tgtctttttag agggtgggct    4800
tttgttgatg agggagggga aaccttttt tttctgtaga ccttttttcag ataacaccat    4860
ctgagtcata accagcctgg cagtgtgatg acgtagatgc agagggagca gctccttggt    4920
gaatgagtga taagtaaagg cagaaaaaat aatgtcatgt ctccatgggg aatgagcatg    4980
agccagagat tgttcctact gatgaaaagc tgcatatgca aaaatttaag caaatgaaag    5040
caaccagtat aaagttatgg caatacctt aaaagttatg gcttatctac caagctttat    5100
ccacaaaagt aaagaattga tgaaaacag tgaagatcaa atgttcatct caaaactgct    5160
tttacaaaag cagaatagaa atgaagtgaa aatgctgcat taagcctgga gtaaaaagaa    5220
```

```
gctgagcttg ttgagatgag tgggatcgag cggctgcgag gcggtgcagt gtgccaatgt   5280
ttcgtttgcc tcagacaggt ttctcttcat aagcagaaga gttgcttcat tccatctcgg   5340
agcaggaaac agcagactgc tgttgacaga taagtgtaac ttggatctgc agtattgcat   5400
gttagggata gataagtgcc ttttttctct ttttccaaaa agacctgtag agctgttgaa   5460
tgtttgcagc tggcccctct taggcagttc agaattttga gtagttttcc catccagcct   5520
cttaaaaatt cctaagcctt gcaccgatgg gctttcatga tgggatagct aataggcttt   5580
tgcatcgtaa acttcaacac aaaagcctac atgattaatg cctactttaa ttacattgct   5640
tacaagatta aggaatcttt atcttgaaga ccccatgaaa gggatcatta tgtgctgaaa   5700
attagatgtt catattgcta aaatttaaat gtgctccaat gtacttgtgc ttaaaatcat   5760
taaattatac aaattaataa aatacttcac tagagaatgt atgtatttag aaggctgtct   5820
ccttatttaa ataaagtctt gtttgttgtc tgtagttagt gtgggcaatt ttgggggat    5880 gttcttctct aatcttttca gaaacttgac ttcgaacact taagtggacc agatcaggat   5940
ttgagccaga agaccgaaat taactttaag gcaggaaaga caaattttat tctccatgca   6000
gtgatgagca tttaataatt gcaggcctgg catagaggcc gtctaactaa ggactaagta   6060
ccttaggcag gtgggagatg atggtcagag taaaaggtaa ctacatattt tgtttccaga   6120
aagtcagggg tctaatttga ccatggctaa acatctaggg taagacactt ttcccccaca   6180
tttccaaata tgcatgttga gtttaaatgc ttacgatcat ctcatccact ttagcctttt   6240
gtcacctcac ttgagccacg agtggggtca ggcatgtggg tttaaagagt tttccttgc    6300 agagcctcat ttcatccttc atggagctgc tcaggacttt gcatataagc gcttgcctct   6360
gtcttctgtt ctgctagtga gtgtgtgatg tgagaccttg cagtgagttt gttttcctg    6420 gaatgtggag ggagggggg atgggctta cttgttctag ctttttttt acagaccaca     6480 cagaatgcag gtgtcttgac ttcaggtcat gtctgttctt tggcaagtaa tatgtgcagt   6540
actgttccaa tctgctgcta ttagaatgca ttgtgacgcg actggagtat gattaaagaa   6600
agttgtgttt ccccaagtgt ttggagtagt ggttgttgga ggaaaagcca tgagtaacag   6660
gctgagtgtt gaggaaatgg ctctctgcag ctttaagtaa cccgtgtttg tgattggagc   6720
cgagtccctt tgctgtgctg ccttaggtaa atgttttgt tcatttctgg tgagggggt     6780 tgggagcact gaagccttta gtctcttcca gattcaactt aaaatctgac aagaaataaa   6840
tcagacaagc aacattcttg aagaaatttt aactggcaag tggaaatgtt ttgaacagtt   6900
ccgtggtctt tagtgcatta tctttgtgta ggtgttctct ctcccctccc ttggtcttaa   6960
ttcttacatg caggaacatt gacaacagca gacatctatc tattcaaggg gccagagaat   7020
ccagacccag taaggaaaaa tagcccattt actttaaatc gataagtgaa gcagacatgc   7080
cattttcagt gtggggattg ggaagcccta gttcttcag atgtacttca gactgtagaa    7140
ggagcttcca gttgaattga aattcaccag tggacaaaat gaggacaaca ggtgaacgag   7200
ccttttcttg tttaagatta gctactggta atctagtgtt gaatcctctc cagcttcatg   7260
ctggagcagc tagcatgtga tgtaatgttg gccttggggt ggaggggtga ggtgggcgct   7320
aagccttttt ttaagatttt tcaggtaccc ctcactaaag gcactgaagg cttaatgtag   7380
gacagcggag ccttcctgtg tggcaagaat caagcaagca gtattgtatc gagaccaaag   7440
tggtatcatg gtcggttttg attagcagtg gggactaccc taccgtaaca ccttgttgga   7500
attgaagcat ccaaagaaaa tacttgagag gccctgggct tgttttaaca tctggaaaaa   7560
```

```
aggctgtttt tatagcagcg gttaccagcc caaacctcaa gttgtgcttg caggggaggg        7620
aaaaggggga aagcgggcaa ccagtttccc cagcttttcc agaatcctgt tacaaggtct        7680
ccccacaagt gatttctctg ccacatcgcc accatgggcc tttggcctaa tcacagaccc        7740
ttcacccctc accttgatgc agccagtagc tggatccttg aggtcacgtt gcatatcggt        7800
ttcaaggtaa ccatggtgcc aaggtcctgt gggttgcacc agaaaaggcc atcaattttc        7860
cccttgcctg taatttaaca ttaaaaccat agctaagatg tttttatacat agcacctatg       7920
cagagtaaac aaaccagtat gggtatagta tgtttgatac cagtgctggg tgggaatgta        7980
ggaagtcgga tgaaaagcaa gcctttgtag aagttgttg gggtgggatt gcaaaaattc         8040
tctgctaaga cttttttcagg tggacataac agacttggcc aagctagcat cttagtggaa       8100
gcagattcgt cagtagggtt gtaaaggttt ttcttttcct gagaaaacaa ccttttgttt        8160
tctcaggttt tgcttttttgg cctttcccta gctttaaaaa aaaaaaagca aaagacgctg       8220
gtggctggca ctcctggttt ccaggacggg gttcaagtcc ctgcggtgtc tttgcttgac        8280
tcttatatca tgaggccatt acatttttct tggagggttc taaaggctct gggtatggta       8340
gctgatatca ctggaacact ccccagcctc agtgttgaac tcttgataat taactgcatt       8400
gtctttcagg ttatgcccaa ttcgtcttat tacctctgag tcgacacacc tcctactatt       8460
tattgaatac tttgatttta tgaaataaaa actaaatatc tctcattgtg tgcttctttg       8520
tgcataaaac acaggcttat tttaagccta aagagaccaa atgtctgatc tacctcagct       8580
tctccgatta gtgaggcctt ccctgttttcc ttgggctgca tggctctttc atgcagatgg      8640
ctctaaagtt gggcttgggt cctaggtggc cactcttgca cctcaggaac acaaggcctt       8700
tccctgctgt tcaggctctc ctccctgaga aacattctg gattgtctat gaggaagttg        8760
ggaaaagatg gtgtcgaaaa gaggtggtgt gcattgctcc tctgttccta acactggatg       8820
gaagactagt tttcatgtag tttagggaaa tagttataca tggtctaaag gcccaaaaac       8880
attcccagag tgtatgcaat actgtgtgta agtgtgcact gcgtgtgttt ggaggtcaga        8940
acttctctga ggttctagag atgaagcaag tcctcagcca tggcccaaga atgggaagga       9000
actgggtcct gctgtaccac ttcccattcc ttaaggaaca gtttggcccg gtgtggtgca       9060
agcatggtcg gtcactgaaa aagaaaacc cacttaggtt tcacaggctt gaagagctgc       9120
atgtcatcca gcaaattact ggctgctgta aggacaggcc cctaggtccc agtcccaggt      9180
gcccttcctg ccactcaatc aagccttaca ccctgggcaa aaacatcctg cgttgaaggt      9240
tcagctccca gggctggaaa cttgtgctgg catctacccc agttcaaagg ggctcagcac      9300
attgacaact aaaactaagc cctcaggtga gcaaaatggt ctccttaagg caatcatggt      9360
cattggtgtt cctgcagtaa aggacagcat cacagctgat gtctgtgtac tggctagttt      9420
tgtatcaact tgacacagct ggaattatca cagagaaagc ttcagttggg gaagtgcctc      9480
caagagatcc tccacgagat cctgctctaa ggcattttct caattagtga tcaaggggga      9540
aagacccctt gtgtgtggga ccatctctgg gctggtagtc ttggttcagt tctataagag      9600
agcaggctga gcaagccagg ggaagcaagc cagtaaagaa catccctcca tggcctctgc      9660
atcagctcct gcttcctgac ctgcttgagt tccagtcctg acttccttgg tgatgaacag      9720
cagtatggaa gtgtaagccg aataaaccct gtcctcccca acttgcttct tggtcatgtt      9780
tgtgcaggaa tagaaaccct gactaagaca gtctgagacc tgacagatct gtgctaaagt      9840
ctggtaccaa ctgagctaga ccctgccaca cacctcagta atggcccatt ctgaattcac      9900
ccagagctga ggctttgccg aggtgaggca caaagacttc actggagagc aggagatatg      9960
```
aacagaggtt ggggctcaca cttcctgatt gggggccagg a         10001

```
<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
```
ccaggctggt tatgactcag         20

```
<210> SEQ ID NO 14
<211> LENGTH: 20
<212> TYPE: DNA
<213> ORGANISM: Artificial sequeance
<220> FEATURE:
<223> OTHER INFORMATION: Synthetic oligonucleotide

<400> SEQUENCE: 14
```
gggtcagctg ccaatgctag         20

```
<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
```
cggtgcaagg cttaggaatt         20

```
<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
```
ccttccctga aggttcctcc         20

```
<210> SEQ ID NO 17
<211> LENGTH: 23
<212> TYPE: DNA
<213> ORGANISM: Artificial sequence
<220> FEATURE:
<223> OTHER INFORMATION: Primer

<400> SEQUENCE: 17
```
tgggttagag aaggcgtgta ctg         23

```
<210> SEQ ID NO 18
<211> LENGTH: 18
<212> TYPE: DNA
<213> ORGANISM: Artificial sequence
<220> FEATURE:
<223> OTHER INFORMATION: Primer

<400> SEQUENCE: 18
```
tcagcggcaa ctgggaaa         18

```
<210> SEQ ID NO 19
<211> LENGTH: 25
<212> TYPE: DNA
```

```
<213> ORGANISM: Artificial sequence
<220> FEATURE:
<223> OTHER INFORMATION: Probe

<400> SEQUENCE: 19
cgttggcacg acaccttcag ggact                                          25

<210> SEQ ID NO 20
<211> LENGTH: 15
<212> TYPE: DNA
<213> ORGANISM: Artificial sequence
<220> FEATURE:
<223> OTHER INFORMATION: Primer

<400> SEQUENCE: 20
tcgccgcttg ctgca                                                     15

<210> SEQ ID NO 21
<211> LENGTH: 17
<212> TYPE: DNA
<213> ORGANISM: Artificial sequence
<220> FEATURE:
<223> OTHER INFORMATION: Primer

<400> SEQUENCE: 21
atcggccgtg atgtcga                                                   17

<210> SEQ ID NO 22
<211> LENGTH: 23
<212> TYPE: DNA
<213> ORGANISM: Artificial sequence
<220> FEATURE:
<223> OTHER INFORMATION: Probe

<400> SEQUENCE: 22
ccatggtcaa ccccaccgtg ttc                                            23

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
tcttatgttt ccgaaccgtt                                                20

<210> SEQ ID NO 24
<211> LENGTH: 23
<212> TYPE: DNA
<213> ORGANISM: Artificial sequence
<220> FEATURE:
<223> OTHER INFORMATION: Primer

<400> SEQUENCE: 24
gtaggttaag ttgacggccg tta                                            23

<210> SEQ ID NO 25
<211> LENGTH: 23
<212> TYPE: DNA
<213> ORGANISM: Artificial sequence
<220> FEATURE:
<223> OTHER INFORMATION: Primer

<400> SEQUENCE: 25
atcttccctg tttccaactc atg                                            23
```

```
<210> SEQ ID NO 26
<211> LENGTH: 27
<212> TYPE: DNA
<213> ORGANISM: Artificial sequence
<220> FEATURE:
<223> OTHER INFORMATION: Probe

<400> SEQUENCE: 26
aaaaatcctt cgactggcgc atgtacg                                              27

<210> SEQ ID NO 27
<211> LENGTH: 21
<212> TYPE: DNA
<213> ORGANISM: Artificial sequence
<220> FEATURE:
<223> OTHER INFORMATION: Primer

<400> SEQUENCE: 27
aaagcaaggt ctccccacaa g                                                    21

<210> SEQ ID NO 28
<211> LENGTH: 24
<212> TYPE: DNA
<213> ORGANISM: Artificial sequence
<220> FEATURE:
<223> OTHER INFORMATION: Primer

<400> SEQUENCE: 28
tgaagggtct gtgctagatc aaaa                                                 24

<210> SEQ ID NO 29
<211> LENGTH: 19
<212> TYPE: DNA
<213> ORGANISM: Artificial sequence
<220> FEATURE:
<223> OTHER INFORMATION: Probe

<400> SEQUENCE: 29
tgccacatcg ccaccccgt                                                       19
```

METHODS FOR MODULATING METASTASIS-ASSOCIATED-IN-LUNG-ADENOCARCINOMA-TRANSCRIPT-1 (MALAT-1) EXPRESSION

CROSS REFERENCED TO RELATED APPLICATIONS

This application is a U.S. National Phase filing under 35 U.S.C. §371 claiming priority to International Serial No. PCT/US2012/071371 filed Dec. 21, 2012, which claims priority to U.S. Provisional Application 61/579,343, filed Dec. 22, 2011, each of which is incorporated herein by reference in its entirety.

SEQUENCE LISTING

The present application is being filed along with a Sequence Listing in electronic format. The Sequence Listing is provided as a file entitled BIOL0181USASEQ_ST25.TXT, created Jun. 23, 2014, which is 124 Kb in size. The information in the electronic format of the sequence listing is incorporated herein by reference in its entirety.

FIELD

The present embodiments relate to the field of cancer biology. More particularly, embodiments provided herein are drawn to compounds and methods for reducing expression of Metastasis-Associated-in-Lung-Adenocarcinoma-Transcript-1 (MALAT-1) RNA and/or protein in an animal. Such methods are useful to treat cancer, such as colon cancer, intestinal cancer, lung cancer (e.g. non-small cell lung cancer), liver cancer, and/or prostate cancer. In various aspects, the cancer is a primary cancer.

BACKGROUND

MALAT, also known as noncoding nuclear-enriched abundant transcript 2 (NEAT2) is a large, infrequently spliced non-coding RNA that is highly conserved amongst mammals. MALAT-1 is expressed in the nucleus and positively regulates cell motility by transcriptional and/or post-transcriptional regulation of motility-related genes. Additionally, MALAT-1 has been implicated in the regulation of alternative splicing. However, the functional role of MALAT-1 in carcinogenesis is largely unknown.

SUMMARY

Embodiments provided herein relate to the discovery that MALAT-1 specific inhibitors can treat cancer in vivo. Several embodiments are drawn to MALAT-1 specific inhibitors, such as antisense compounds, and methods for modulating expression of MALAT-1 RNA and protein using the same. In certain embodiments, MALAT-1 specific inhibitors modulate MALAT-1 RNA and/or protein expression or activity.

Also provided are methods of treating cancer with MALAT-1 specific inhibitors, such as antisense compounds. In some embodiments, methods of treating cancer in an animal include administering to the animal an antisense compound which reduces expression of MALAT-1. Types of cancers that can be treated with the MALAT-1 specific inhibitors provided herein include but are not limited to colon cancer, intestinal cancer, lung cancer (e.g. non-small cell lung cancer), liver cancer, and/or prostate cancer. In various aspects, the cancer is a primary cancer.

In several embodiments, a method of treating cancer in an animal includes administering to the animal an antisense compound which reduces expression of MALAT-1. In one aspect, the antisense compound comprises a modified oligonucleotide consisting of 12 to 30 linked nucleosides, wherein the modified oligonucleotide is at least 85% complementary to a MALAT-1 nucleic acid.

Several embodiments are directed to the use of a compound including a modified oligonucleotide consisting of 12 to 30 linked nucleosides at least 85% complementary to a MALAT-1 nucleic acid in the manufacture of a medicament for treating cancer.

Further embodiments relate to compounds for use in the treatment of cancer including a modified oligonucleotide consisting of 12 to 30 linked nucleosides at least 85% complementary to a MALAT-1 nucleic acid.

In various aspects of any of the aforementioned embodiments, expression of MALAT-1 RNA is reduced; expression of MALAT-1 protein is reduced; the animal is a human; the MALAT-1 nucleic acid is a human MALAT-1 nucleic acid (e.g. any one of SEQ ID NOs:1-9); the modified oligonucleotide is 100% complementary to a human MALAT-1 nucleic acid (e.g. any one of SEQ ID NOs:1-9); the modified oligonucleotide inhibits cancer growth and/or metastasis; the modified oligonucleotide increases survival of the animal; the cancer is colon cancer, intestinal cancer, lung cancer, liver cancer, or prostate cancer; the cancer is a primary cancer; the expression of MALAT-1 is reduced in cancer cells of the animal compared to control or untreated animals; the modified oligonucleotide is a single-stranded oligonucleotide; the modified oligonucleotide comprises at least one modified internucleoside linkage such as a phosphorothioate internucleoside linkage; at least one nucleoside comprises a modified sugar; the modified sugar is a bicyclic sugar such as a 4'-CH(CH$_3$)—O-2' bridge; the modified oligonucleotide includes at least one tetrahydropyran modified nucleoside wherein a tetrahydropyran ring replaces the furanose ring; the modified sugar comprises a 2'-O-methoxyethyl group; and/or at least one nucleoside comprises a modified nucleobase such as a 5-methylcytosine.

DETAILED DESCRIPTION

It is to be understood that both the foregoing general description and the following detailed description are explanatory only and are not restrictive of the invention as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting.

All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"5-methylcytosine" means a cytosine modified with a methyl group attached to the 5' position. A 5-methylcytosine is a modified nucleobase.

"About" means within ±7% of a value. For example, if it is stated, "the compounds inhibited MALAT-1 by about 70%", it is implied that the MALAT-1 levels are inhibited within a range of 63% and 77%.

"Active target region" or "target region" means a region to which one or more active antisense compounds is targeted. "Active antisense compounds" means antisense compounds that reduce target nucleic acid levels or protein levels.

"Administering" means providing a pharmaceutical agent to an individual, and includes, but is not limited to administering by a medical professional and self-administering.

"Amelioration" or "ameliorate" or "ameliorating" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, and miRNAs.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Metastasis-Associated-in-Lung-Adenocarcinoma-Transcript-1 (MALAT-1)" means any nucleic acid or protein of MALAT-1. "MALAT-1 nucleic acid" means any nucleic acid encoding MALAT-1. For example, in certain embodiments, a MALAT-1 nucleic acid includes a DNA sequence encoding MALAT-1, an RNA sequence transcribed from DNA encoding MALAT-1 (including genomic DNA comprising introns and exons), including a non-protein encoding (i.e. non-coding) RNA sequence, and an mRNA sequence encoding MALAT-1. "MALAT-1 mRNA" means an mRNA encoding a MALAT-1 protein.

"MALAT-1 specific inhibitor" refers to any agent capable of specifically inhibiting MALAT-1 RNA and/or MALAT-1 protein expression or activity at the molecular level. For example, MALAT-1 specific inhibitors include nucleic acids (including antisense compounds), peptides, antibodies, small molecules, and other agents capable of inhibiting the expression of MALAT-1 RNA and/or MALAT-1 protein.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Inhibiting MALAT-1" means reducing expression of MALAT-1 RNA and/or protein levels in the presence of a MALAT-1 specific inhibitor, including a MALAT-1 antisense oligonucleotide, as compared to expression of MALAT-1 RNA and/or protein levels in the absence of a MALAT-1 specific inhibitor, such as a MALAT-1 antisense oligonucleotide.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provided herein relate to methods for decreasing MALAT-1 RNA and/or protein expression in an animal.

Certain embodiments provide methods for the treatment or amelioration of diseases, disorders, and conditions associated with MALAT-1, such as cancer, in an animal in need thereof. In several embodiments, the cancer can be colon cancer, lung cancer (e.g. non-small cell lung cancer), liver cancer, and/or prostate cancer.

Certain embodiments provide for the use of a MALAT-1 specific inhibitor for treating cancer in an animal by administering a MALAT-1 specific inhibitor, such as nucleic acids (including antisense compounds) capable of reducing the levels of MALAT-1 RNA and/or MALAT-1 protein.

Certain embodiments provide for methods of treating cancer in an animal, comprising administering to the animal a therapeutically effective amount of a MALAT-1 specific inhibitor. In certain embodiments, the animal is a human.

In certain embodiments, the MALAT-1 specific inhibitor is an antisense compound. In certain embodiments, the antisense compound is a modified oligonucleotide.

In certain embodiments, the MALAT-1 specific inhibitor is a nucleic acid. In certain embodiments, the nucleic acid is a modified oligonucleotide.

In certain embodiments, the MALAT-1 specific inhibitor is a modified oligonucleotide.

In certain embodiments, the modified oligonucleotide consists of 12 to 30 linked nucleosides.

In certain embodiments, the modified oligonucleotide is a single-stranded oligonucleotide.

In certain embodiments, the modified oligonucleotide consists of 15, 16, 17, 18, 19, or 20 linked nucleosides.

In certain embodiments, the modified oligonucleotide has a nucleobase sequence that is 80%, 85%, 90%, 95%, or 100% complementary to a human MALAT-1 nucleic acid.

In certain embodiments, the modified oligonucleotide comprises at least one modified internucleoside linkage. In certain embodiments, each modified internucleoside linkage is a phosphorothioate internucleoside linkage.

In certain embodiments, at least one nucleoside of the modified oligonucleotide comprises a modified sugar. In certain embodiments, the modified sugar is a bicyclic sugar. In certain embodiments, the bicyclic sugar comprises a 4'-CH(CH$_3$)—O-2' bridge.

In certain embodiments, the modified sugar comprises a 2'-O-methoxyethyl group.

In certain embodiments, at least one nucleoside of the modified oligonucleotide comprises a modified nucleobase. In certain embodiments, the modified nucleobase is a 5'-methylcytosine.

In certain embodiments, at least one nucleoside of the modified oligonucleotide comprises at least one tetrahydropyran modified nucleoside wherein a tetrahydropyran ring replaces the furanose ring. In certain embodiments, each of the at least one tetrahydropyran modified nucleoside has the structure:

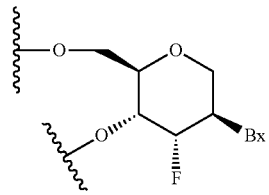

wherein Bx is an optionally protected heterocyclic base moiety.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned immediately adjacent to and between the 5' wing segment and the 3' wing segment and wherein each nucleoside of each wing segment comprises a modified sugar. In some such embodiments, each cytosine in the modified oligonucleotide is a 5-methylcytosine.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

Several embodiments described herein provide for methods comprising administering to an animal having cancer a therapeutically effective amount of a modified oligonucleotide consisting of 12 to 30 linked nucleosides, wherein the modified oligonucleotide is at least 80% complementary to a human MALAT-1 nucleic acid. In certain embodiments, the modified oligonucleotide is at least 90% complementary to a human MALAT-1 nucleic acid. In certain embodiments, the modified oligonucleotide is 100% complementary to a human MALAT-1 nucleic acid.

In certain embodiments, the modified oligonucleotide targets a human MALAT-1 nucleic acid which may be selected from, but not limited to, one or more of GENBANK Accession No. EF177381.1 (incorporated herein as SEQ ID NO: 1), GENBANK Accession No. BK001411.1 1 (incorporated herein as SEQ ID NO: 2), GENBANK Accession No. BQ429080.1 (incorporated herein as SEQ ID NO: 3), GENBANK Accession No. BQ428957.1 (incorporated herein as SEQ ID NO: 4), GENBANK Accession No. NT_033903.7 truncated from nucleobases 10569000 to 10582000 (incorporated herein as SEQ ID NO: 5), GEN- BANK Accession No. XR_001309.1 (incorporated herein as SEQ ID NO: 6), or GENBANK Accession No. NR_002819.2 (incorporated herein as SEQ ID NO: 7), GENBANK Accession No. NC_000011.9 from nucleobases 65265233 to 65273940 (incorporated herein as SEQ ID NO: 8) or the complement thereof, and GENBANK Accession No. AC_000143.1 from nucleobases 61592326 to 61601033 (incorporated herein as SEQ ID NO: 9) or the complement thereof.

In certain embodiments, the modified oligonucleotide targets a mouse MALAT-1 nucleic acid which may be selected from, but not limited to, one or more of GENBANK Accession No. NR_002847.2 (incorporated herein as SEQ ID NO: 10), GENBANK Accession No. FJ209304.1 (incorporated herein as SEQ ID NO: 11), and the complement of GENBANK Accession No. NT_082868.4 truncated from nucleobases 2689000 to 2699000 (incorporated herein as SEQ ID NO: 12).

In certain embodiments, antisense compounds may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

In certain embodiments, antisense compounds may comprise a modified oligonucleotide comprising a nucleobase sequence 100% complementary to an equal length portion of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

In certain embodiments, the nucleobase sequence of the modified oligonucleotide is 100% complementary to a nucleobase sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

Antisense Compounds

Antisense compounds provided herein refer to oligomeric compounds capable of undergoing hybridization to a target nucleic acid through hydrogen bonding Examples of antisense compounds include single-stranded and double-stranded compounds, such as, antisense oligonucleotides, siRNAs, shRNAs, and miRNAs.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a MALAT-1 nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In several embodiments an antisense compound targeted to a MALAT-1 nucleic acid can have antisense portions of 10 to 50 nucleobases in length. One having ordinary skill in the art will appreciate that this embodies antisense compounds having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length, or any range therewithin.

In several embodiments, an antisense compound targeted to a MALAT-1 nucleic acid can have antisense portions of 12 to 30 nucleobases in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleobases in length, or any range therewithin.

In some embodiments, an antisense compound targeted to a MALAT-1 nucleic acid can have antisense portions of 12 or 13 to 24 nucleobases in length. One having ordinary skill in the art will appreciate that this embodies antisense compounds having antisense portions of 12, 13, 14, 15, 16, 17, 18, 19, 20, 21, 22, 23 or 24 nucleobases in length, or any range therewithin.

In some embodiments, an antisense compound targeted to a MALAT-1 nucleic acid can have antisense portions of 19 to 23 nucleobases in length. One having ordinary skill in the art will appreciate that this embodies antisense compounds having antisense portions of 19, 20, 21, 22 or 23 nucleobases in length, or any range therewithin.

In certain embodiments antisense compounds targeted to a MALAT-1 nucleic acid may be shortened or truncated. For example, a single subunit may be deleted from the 5' end (5' truncation), or alternatively from the 3' end (3' truncation). A shortened or truncated antisense compound targeted to a MALAT-1 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases. Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to a MALAT-1 nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:

each A is independently a 2'-substituted nucleoside;

each B is independently a bicyclic nucleoside;

each J is independently either a 2'-substituted nucleoside or a 2'-deoxynucleoside;

each D is a 2'-deoxynucleoside;

m is 0-4; n is 0-2; p is 0-2; r is 0-2; t is 0-2; v is 0-2; w is 0-4; x is 0-2; y is 0-2; z is 0-4; g is 6-14; provided that:

at least one of m, n, and r is other than 0;

at least one of w and y is other than 0;

the sum of m, n, p, r, and t is from 2 to 5; and the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

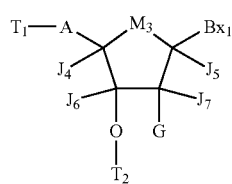

IIc wherein:

$T_1$ is an optionally protected phosphorus moiety;

$T_2$ is an internucleoside linking group linking the compound of Formula IIc to the oligomeric compound;

A has one of the formulas:

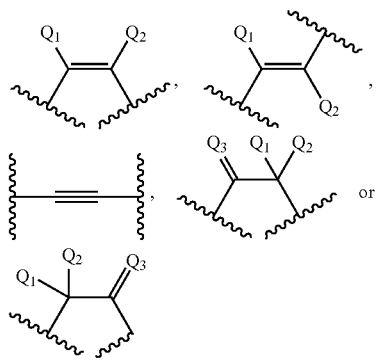

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, $C[$=$C(R_{20})(R_{21})]$ and $C($=$O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C$=$O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, $CN$, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

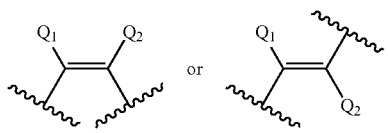

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

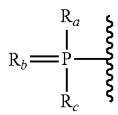

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

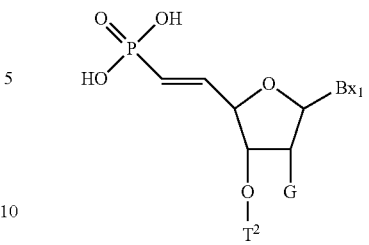

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

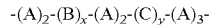

wherein: A is a first type of modified nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

5'-(Q)-(AB)$_x$A$_y$-(D)$_z$ wherein:

Q is a nucleoside comprising a stabilized phosphate moiety. In certain embodiments, Q is a nucleoside having Formula IIc or IIe;

A is a first type of modified nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

5'-(Q)-(A)$_x$-(D)$_z$ wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
| --- | --- | --- |
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is MALAT-1. In certain embodiment, the degradation of the targeted MALAT-1 is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target MALAT-1 by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

"Targeting" an oligomeric compound to a particular nucleic acid molecule can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In several embodiments provided herein, the target nucleic acid encodes MALAT-1.

Nucleotide sequences that encode human MALAT-1 are target nucleic acids in several embodiments include, without limitation, the following: GENBANK Accession No. EF177381.1 (incorporated herein as SEQ ID NO: 1), GENBANK Accession No. BK001411.1 1 (incorporated herein as SEQ ID NO: 2), GENBANK Accession No. BQ429080.1 (incorporated herein as SEQ ID NO: 3), GENBANK Accession No. BQ428957.1 (incorporated herein as SEQ ID NO: 4), GENBANK Accession No. NT_033903.7 truncated from nucleobases 10569000 to 10582000 (incorporated herein as SEQ ID NO: 5), GENBANK Accession No. XR_001309.1 (incorporated herein as SEQ ID NO: 6), or GENBANK Accession No. NR_002819.2 (incorporated herein as SEQ ID NO: 7), GENBANK Accession No. NC_000011.9 from nucleobases 65265233 to 65273940 (incorporated herein as SEQ ID NO: 8), GENBANK Accession No. AC_000143.1 from nucleobases 61592326 to 61601033 (incorporated herein as SEQ ID NO: 9).

Nucleotide sequences that encode mouse MALAT-1 are target nucleic acids in several embodiments include, without limitation, the following: GENBANK Accession No. NR_002847.2 (incorporated herein as SEQ ID NO: 10), GENBANK Accession No. FJ209304.1 (incorporated herein as SEQ ID NO: 11), and the complement of GENBANK Accession No. NT_082868.4 truncated from nucleobases 2689000 to 2699000 (incorporated herein as SEQ ID NO: 12).

It is understood that the sequence set forth in each SEQ ID NO in the Detailed Description and/or Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

The targeting process usually also includes determination of at least one target region, segment, or site within the target nucleic acid for the antisense interaction to occur such that the desired effect, e.g., modulation of expression, will result. Within the context of the present embodiments, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Generally, suitable target segments may be found within a 5' UTR, a coding region, a 3' UTR, an intron, an exon, or an exon/intron junction. Target segments containing a start codon or a stop codon generally are also suitable target segments. A suitable target segment may specifically exclude a certain structurally defined region such as the start codon or stop codon. However, as MALAT-1 transcripts are considered non-coding, suitable target segments may be found throughout the length of the transcript, which is believed to be untranslated.

Nonetheless, target segments including possible MALAT-1 coding transcripts and any structurally defined regions are still contemplated in several embodiments. For example, a target region may encompass a 3' UTR, a 5' UTR, an exon, an intron, an exon/intron junction, a coding region, a translation initiation region, translation termination region, or other defined nucleic acid region. The structurally defined regions for MALAT-1 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding tyrosinase, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also possible target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in MALAT-1 mRNA levels are indicative of inhibition of MALAT-1 expression. Reductions in levels of MALAT-1 protein are also indicative of inhibition of target mRNA expression.

Hybridization

In some embodiments, hybridization occurs between an antisense compound disclosed herein and a MALAT-1 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a MALAT-1 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a MALAT-1 nucleic acid).

Non-complementary nucleobases between an antisense compound and a MALAT-1 nucleic acid may be tolerated provided that the antisense compound remains able to specifically hybridize to a target nucleic acid. Moreover, an antisense compound may hybridize over one or more segments of a MALAT-1 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a MALAT-1 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a MALAT-1 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a MALAT-1 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a MALAT-1 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a MALAT-1 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_1$)—(CH$_2$)$_2$—N(R$_m$)(R$_n$), where each R$_1$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' (also referred to as constrained ethyl or cEt) and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)$_n$]—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)$_n$—O—, —C($R_a R_b$)—N(R)—O— or —C($R_a R_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2) BNA, (B) β-D-methyleneoxy (4'-CH$_2$—O-2) BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2) BNA, and (F) methyl(methyleneoxy) (4'-CH(CH$_3$)—O-2) BNA, (G) methylene-thio (4'-CH$_2$—S-2) BNA, (H) methylene-amino (4'-CH$_2$—N(R)-2') BNA, (I) methyl carbocyclic (4'-CH$_2$—CH(CH$_3$)-2) BNA, (J) propylene carbocyclic (4'-(CH$_2$)$_3$-2') BNA and (K) vinyl BNA as depicted below:

(A)

(B)
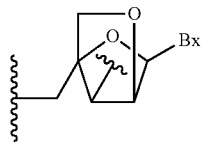

(C)
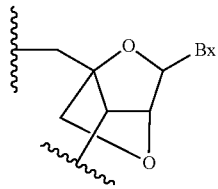

(D)
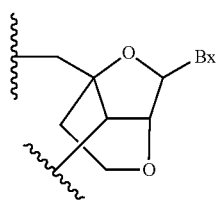

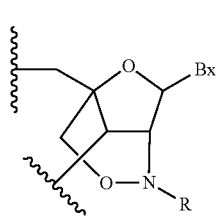

-continued (E)
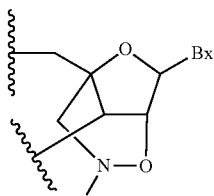

(F)
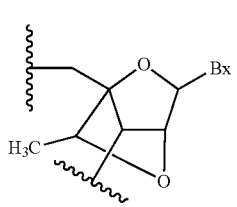

(G)
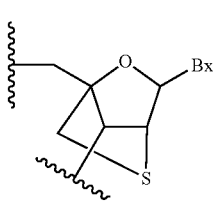

(H)
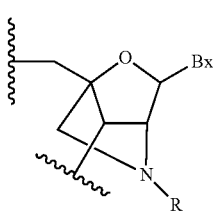

(I)
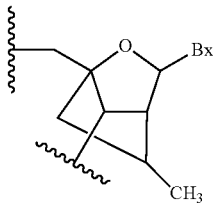

(J)
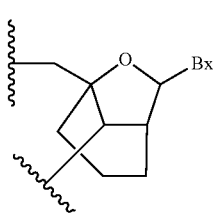

(K)
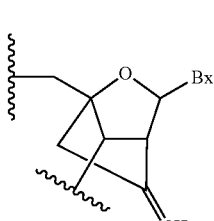

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

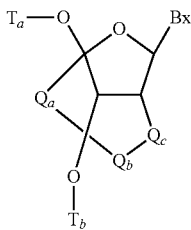

wherein:

Bx is a heterocyclic base moiety;

-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

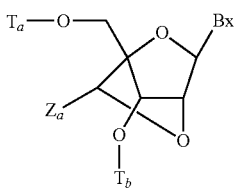

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC$(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

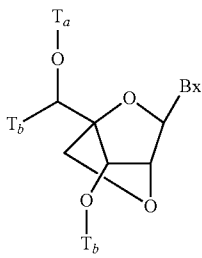

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

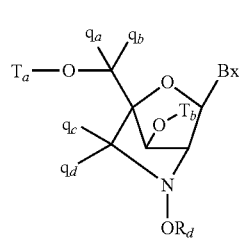

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

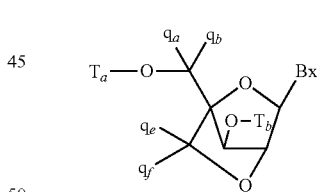

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)—$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-CH₂—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH₂—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

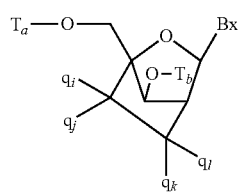

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH₂)₃-2' bridge and the alkenyl analog bridge 4'-CH=CH—CH₂-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH₂)ₙO]ₘCH₃, O(CH₂)ₙNH₂, O(CH₂)ₙCH₃, O(CH₂)ₙF, O(CH₂)ₙONH₂, OCH₂C(=O)N(H)CH₃, and O(CH₂)ₙON[(CH₂)ₙCH₃]₂, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH₃, OCN, Cl, Br, CN, F, CF₃, OCF₃, SOCH₃, SO₂CH₃, ONO₂, NO₂, N₃, NH₂, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F—HNA) having a tetrahydropyran ring system as illustrated below:

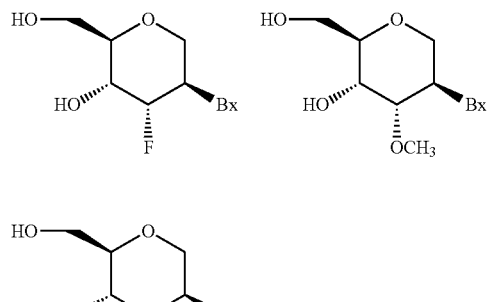

In certain embodiments, sugar surrogates are selected having Formula VII:

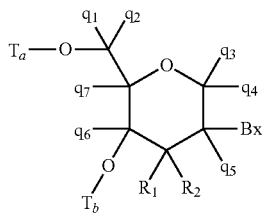

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

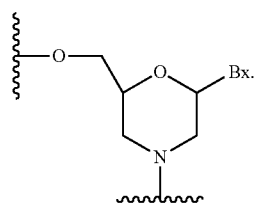

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horváth et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

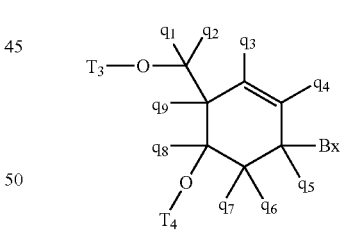

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

For additional conjugates including those useful for ssRNA and their placement within antisense compounds, see e.g., U.S. Application No. 61/583,963.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a MALAT-1 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a MALAT-1 nucleic acid and a pharmaceutically acceptable diluent. In certain embodiments, the pharmaceutically acceptable diluent is PBS. In certain embodiments, the antisense compound is an antisense oligonucleotide.

Treatment of Cancer

In several embodiments, the antisense compounds provided herein are useful for the treatment of cancer in an animal. Examples of certain types of cancers that can be treated with the antisense compounds described herein include, but are not limited to, colon cancer, intestinal cancer, lung cancer (e.g. non-small cell lung cancer), liver cancer, and/or prostate cancer.

As used herein, the terms "tumor cells," "cancer cells," "malignant cells," and "neoplastic cells" are used interchangeably and do not require a particular distinction as to the extent or degree of transformation or malignancy relative to a "normal cell." Accordingly, "tumor cells," "cancer cells," and "neoplastic cells" are transformed and/or malignant cells, whereas "normal cells" are not transformed and/or malignant.

The term "treating cancer" refers to performing actions that lead to amelioration of cancer or of the symptoms accompanied therewith to a significant extent. The combination of said actions is encompassed by the term "treatment." Amelioration of a cancer includes but is not limited to reducing in the number of cancer cells in an animal or reducing the number of cancer cells at a specific site in the body of an animal. Said treatment as used herein also includes an entire restoration of the health with respect to the cancers referred to herein. It is to be understood that treatment as used in accordance with embodiments provided herein may not be effective in all subjects to be treated. However, a statistically significant portion of subjects suffering from a cancer referred to herein can be successfully treated. Whether a portion is statistically significant can be determined without by a person of ordinary skill in the art using various well known statistic evaluation tools, e.g., determination of confidence intervals, p-value determination, Student's t-test, Mann-Whitney test, etc.

The term "administration" or "administering" includes routes of introducing a MALAT-1 specific inhibitor to an animal to perform its intended function. An example of a route of administration that can be used includes, but is not limited to parenteral administration, such as subcutaneous, intravenous, intramuscular, intraarterial, intraperitoneal, or intracranial injection or infusion.

When a MALAT-1 specific inhibitor is administered parenterally, such as by subcutaneous or intravenous injection or other injection, it can be in the form of a pyrogen-free, parenterally acceptable aqueous solution or suspension. Suspensions can be formulated using suitable dispersing or wetting agents and suspending agents. Compositions for injection can contain a vehicle such as water, saline (e.g., physiological buffered saline), or other isotonic vehicles such as isotonic sodium chloride solution, Ringer's solution, dextrose solution, or other vehicles known in the art.

As used herein, the term "treatment of cancer" or "treating cancer" can be described by a number of different parameters including, but not limited to, reduction in the size of a tumor in an animal having cancer, reduction in the growth or proliferation of a tumor in an animal having cancer, preventing metastasis or reducing the extent of metastasis, and/or extending the survival of an animal having cancer compared to control. In the context of colon cancer, treating colon cancer can also be measured by a reduction in the number of colon polyps of an animal having colon cancer. In several embodiments, the cancer can be a primary cancer.

Several embodiments are drawn to methods of reducing tumor volume or number in an animal comprising administering a MALAT-1 specific inhibitor to the animal. In various aspects of such embodiments, the MALAT-1 specific inhibitor can be an antisense compound which reduces expression of MALAT-1. It will be understood that any of the MALAT-1 specific inhibitors described herein can be used in embodiments relating to methods of reducing tumor volume or number in an animal. Furthermore, any antisense compound targeting MALAT-1 as described herein can be used in methods of reducing tumor volume or number in an animal. For example, an antisense compound useful for reducing tumor volume can include a modified oligonucleotide consisting of 12 to 30 linked nucleosides, wherein the modified oligonucleotide is at least 85% complementary to a MALAT-1 nucleic acid. In several embodiments, the tumor volume can refer to the volume of a primary tumor.

Various embodiments are drawn to methods of inhibiting tumor growth or proliferation in an animal comprising administering a MALAT-1 specific inhibitor to the animal. In several aspects, the growth or proliferation of a primary tumor can be inhibited by administering a MALAT-1 specific inhibitor to the animal. In various aspects of such embodiments, the MALAT-1 specific inhibitor can be an antisense compound which reduces expression of MALAT-1. It will be understood that any of the MALAT-1 specific inhibitors described herein can be used in embodiments relating to methods of inhibiting tumor growth or proliferation in an animal. Furthermore, any antisense compound targeting MALAT-1 as described herein can be used in methods of inhibiting tumor growth or proliferation in an animal. For example, an antisense compound useful for inhibiting tumor growth or proliferation can include a modified oligonucleotide consisting of 12 to 30 linked nucleosides, wherein the modified oligonucleotide is at least 85% complementary to a MALAT-1 nucleic acid.

Certain embodiments are drawn to methods of inhibiting cancer metastasis in an animal comprising administering a MALAT-1 specific inhibitor to the animal. In various aspects of such embodiments, the MALAT-1 specific inhibitor can be an antisense compound which reduces expression of MALAT-1. It will be understood that any of the MALAT-1 specific inhibitors described herein can be used in embodiments relating to methods of inhibiting cancer metastasis in an animal. Furthermore, any antisense compound targeting MALAT-1 as described herein can be used in methods of inhibiting cancer metastasis in an animal. For example, an antisense compound useful for inhibiting cancer metastasis can include a modified oligonucleotide consisting of 12 to 30 linked nucleosides, wherein the modified oligonucleotide is at least 85% complementary to a MALAT-1 nucleic acid.

Several embodiments are drawn to methods of increasing survival of an animal having cancer comprising administering a MALAT-1 specific inhibitor to the animal. In various aspects of such embodiments, the MALAT-1 specific inhibitor can be an antisense compound which reduces expression of MALAT-1. It will be understood that any of the MALAT-1 specific inhibitors described herein can be used in embodiments relating to methods of increasing survival of an animal having cancer. Furthermore, any antisense compound targeting MALAT-1 as described herein can be used in methods of increasing survival of an animal having cancer. For example, an antisense compound useful for increasing survival in an animal having cancer can include a modified oligonucleotide consisting of 12 to 30 linked nucleosides, wherein the modified oligonucleotide is at least 85% complementary to a MALAT-1 nucleic acid.

Certain embodiments are directed to the use of a MALAT-1 specific inhibitor in the manufacture of a medicament for treating cancer. In several aspects, the cancer can be a primary cancer. It will be understood that any of the MALAT-1 specific inhibitors described herein can be used in embodiments relating to use of such inhibitors in the manufacture of a medicament for treating cancer. In some aspects, the MALAT-1 specific inhibitor can comprise a compound including a modified oligonucleotide consisting of 12 to 30 linked nucleosides at least 85% complementary to a MALAT-1 nucleic acid. It will also be understood that MALAT-1 specific inhibitors can be used in the manufacture of a medicament for reducing tumor volume or number, inhibiting tumor growth or proliferation, inhibiting cancer metastasis, and/or increasing survival of an animal having cancer.

Similarly, various embodiments relate to a MALAT-1 specific inhibitor for use in the treatment of cancer. In various aspects the cancer can be a primary cancer. It will be understood that any of the MALAT-1 specific inhibitors described herein can be for use in the treatment of cancer. In some aspects, the MALAT-1 specific inhibitor can comprise a compound including a modified oligonucleotide consisting of 12 to 30 linked nucleosides at least 85% complementary to a MALAT-1 nucleic acid. It will also be understood that MALAT-1 specific inhibitors can be used for reducing tumor volume or number, inhibiting tumor growth or proliferation, inhibiting cancer metastasis, and/or increasing survival of an animal having cancer.

MALAT-1 specific inhibitors of several embodiments can be provided to an administering physician or other health care professional in the form of a kit. The kit is a package which houses a container which contains the MALAT-1 specific inhibitor in a suitable pharmaceutical composition, and instructions for administering the pharmaceutical composition to an animal. The kit can also contain separate doses of a MALAT-1 specific inhibitor for serial or sequential administration. The kit can contain suitable delivery devices, e.g., syringes, and the like, along with instructions for administering the MALAT-1 specific inhibitor. The kit can optionally contain instructions for storage, reconstitution (if applicable), and administration. The kit can include a plurality of containers reflecting the number of administrations to be given to an animal.

Cell Culture and Antisense Compounds Treatment

The effects of antisense compounds on the level, activity or expression of MALAT-1 nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). As an example, b.END cells can be used to test antisense compounds on the activity or expression of MALAT-1 nucleic acids.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a MALAT-1 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a MALAT-1 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of MALAT-1 nucleic acids can be assessed by measuring MALAT-1 protein levels. Protein levels of MALAT-1 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of MALAT-1 are commercially available

EXAMPLES

Having generally described embodiments drawn to compounds and methods for treating cancer in an animal including administering an antisense compound that targets MALAT-1, a further understanding can be obtained by reference to certain specific examples which are provided herein for purposes of illustration only, and are not intended to be limiting.

Example 1

Antisense Inhibition of Murine Metastasis Associated Lung Adenocarcinoma Transcript 1 (MALAT-1) Non-Coding RNA in b.END Cells Antisense oligonucleotides targeted to a murine MALAT-1 nucleic acid were tested for their effects on MALAT-1 RNA in vitro. Cultured b.END cells were plated at a density of 4,000 cells per well and transfected using Cytofectin reagent with 3.125 nM, 6.25 nM, 12.5 nM, 25.0 nM, 50.0 nM, or 100.0 nM concentrations of antisense oligonucleotide, as specified in Table 1. After a treatment period of approximately 16 hours, RNA was isolated from the cells and MALAT-1 RNA levels were measured by quantitative real-time PCR.

ISIS 395251 (CCAGGCTGGTTATGACTCAG; SEQ ID NO: 13), targeting murine MALAT-1 gene sequence, SEQ ID NO: 10 (GENBANK Accession No. NR_002847.2) at start site 3338; ISIS 399462 (GGGTCAGCTGCCAAT-GCTAG; SEQ ID NO: 14), targeting SEQ ID NO: 10 at start site 1280; and ISIS 399479 (CGGTGCAAGGCTTAG-GAATT; SEQ ID NO: 15) targeting SEQ ID NO: 10 at start site 4004, were three of the antisense oligonucleotides tested in the assay. ISIS 395251 is also cross-reactive with human MALAT-1 gene sequence (GENBANK Accession No. NR_002819.2; SEQ ID NO: 7) at start site 4897. The antisense oligonucleotides were designed as 5-10-5 MOE gapmers, and are 20 nucleosides in length, wherein the central gap segment comprises ten 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout the gapmer are phosphorothioate (P=S) linkages. All cytosine residues throughout the gapmer are 5-methylcytosines. The half maximal inhibitory concentration ($IC_{50}$) of each oligonucleotide is also presented in Table 1. As illustrated in Table 1, MALAT-1 RNA levels were significantly reduced in a dose-dependent manner in antisense oligonucleotide treated cells.

TABLE 1

| Dose-dependent inhibition of MALAT-1 RNA in b.END cells | | | | | | | |
|---|---|---|---|---|---|---|---|
| ISIS No | 3.125 nM | 6.25 nM | 12.5 nM | 25.0 nM | 50.0 nM | 100.0 nM | $IC_{50}$ (nM) |
| 399479 | 14 | 31 | 55 | 71 | 84 | 91 | 12.6 |
| 399462 | 20 | 36 | 50 | 68 | 81 | 92 | 12.3 |
| 395251 | 23 | 45 | 57 | 66 | 85 | 90 | 10.1 |

Example 2

Effect of Antisense Inhibition of MALAT-1 in an ApcMin Mouse Model

ApcMin (Min, multiple intestinal neoplasia) is a point mutation in the murine homolog of the APC gene. Min/+ mice develop intestinal adenomas and are considered a standard model that mirrors the human condition (Moser, A. R. et al., Proc. Natl. Acad. Sci. USA. 90: 8977, 1993). The effect of inhibition of MALAT-1 RNA expression with antisense oligonucleotides on small intestinal polyps load was examined in ApcMin mice.

Treatment

ApcMin mice, 9 weeks in age, were randomly divided into three treatment groups of 4 mice each. The first treatment group was injected with 50 mg/kg of ISIS 399479 (SEQ ID NO: 15), administered subcutaneously 5 days per week for 4 weeks. The second treatment group was injected with 50 mg/kg of control oligonucleotide, ISIS 141923 (5'-CCTTCCCTGAAGGTTCCTCC-3', a 5-10-5 MOE gapmer, designated herein as SEQ ID NO: 16, having no known homology to any mouse gene), administered subcutaneously 5 days per week for 4 weeks. The third group was injected with PBS, administered subcutaneously 5 days per week for 4 weeks. On day 28, the mice were euthanized with isoflurane followed by cervical dislocation. Small intestines, colons, and liver tissue were collected and processed for further analysis.

RNA Analysis

RNA isolation was performed using the Invitrogen PureLink™ Total RNA Purification Kit, according to the manufacturer's protocol. RT-PCR was performed using the Step One Plus system from Applied Biosystems. MALAT-1 RNA expression was measured using primer probe set mMALAT1#2 (forward sequence TGGGTTAGAGAAGGCGTGTACTG, designated herein as SEQ ID NO: 17; reverse sequence TCAGCGGCAACTGGGAAA, designated herein as SEQ ID NO: 18; probe sequence CGTTGGCACGACACCTTCAGGGACT, designated herein as SEQ ID NO: 19) and normalized to Cyclophilin mRNA expression. The primer probe set for Cyclophilin was m_Cyclo24 (forward sequence TCGCCGCTTGCTGCA, designated herein as SEQ ID NO: 20; reverse sequence ATCGGCCGTGATGTCGA, designated herein as SEQ ID NO: 21; probe sequence CCATGGTCAACCCCACCGTGTTC, designated herein as SEQ ID NO: 22).

MALAT-1 RNA expression was assessed in the liver and intestines. As shown in Table 2, MALAT-1 RNA expression in mice treated with ISIS 399479 was significantly inhibited compared to the control oligonucleotide-treated group. The mRNA expression levels are expressed as percent inhibition of expression levels compared to that in the PBS control.

TABLE 2

Percent inhibition of MALAT-1 RNA levels (%) compared to the PBS control

|  | ISIS 399479 | ISIS 141923 |
|---|---|---|
| Liver | 98 | 0 |
| Intestines | 94 | 6 |

Cell Proliferation Analysis

The BrdU cell proliferation assay (Rothaeusler, K. and Baumgarth, N. Curr. Protoc. Cytom. 2007. Chapter 7: Unit 7.31) detects 5-bromo-2'-deoxyuridine (BrdU) incorporated into cellular DNA during cell proliferation. The quantity of BrdU incorporated into cells is a direct indicator of cell proliferation and was measured using an anti-BrdU antibody (Sigma Aldrich).

BrdU, at a concentration of 50 mg/kg, was injected intraperitoneally for 5 consecutive days starting at day 24. The animals were euthanized on day 28. The entire small intestine from each animal was made in a 'Swiss roll', a standard technique for histological studies of rodent intestine (Moolenbeek, C. and Ruitenberg, E. J. Lab Anim. 1981. 15: 57-9). Two sections of the intestine at least 500 μm apart were excised from each roll. BrdU positive tumor cells were measured from all the polyps in both sections.

The results are presented in Table 3, as the percentage of BrdU positive cells detected. As shown in Table 3, there was a decrease in the percentage of positive cells in the ISIS 399479-treated mice compared to the control. This result corresponds with the reduction in MALAT-1 expression, measured using ViewRNA software and as shown in Table 4. The data is presented as the signal density of MALAT-1 mRNA expression levels multiplied by the total BrdU positive cells, presented in arbitrary units.

Therefore, treatment of ApcMin mice with antisense oligonucleotides targeting MALAT-1 shows decrease in tumor cell proliferation compared to the control group.

TABLE 3

BrdU positive cells (%) in ApcMin mice

|  | % |
|---|---|
| ISIS 399479 | 23 |
| ISIS 141923 | 51 |
| PBS | 48 |

TABLE 4

MALAT-1 expression levels in ApcMin mice (signal density of MALAT-1 mRNA expression levels multiplied by the total BrdU positive cells presented as arbitrary units (a.u.))

|  | a.u. |
|---|---|
| ISIS 399479 | 9.6 |
| ISIS 141923 | 16.2 |

Measurement of Tumor Polyps Load

The entire small intestine from each animal was made in a 'Swiss roll' and processed for paraffin embedding. Two sections of the intestine at least 500 μm apart were collected from each roll. The sections were stained with haematoxylin and eosin, and the number of polyps were counted in both sections, and then divided by two. As shown in Table 5, tumor polyps load was decreased in ApcMin mice treated with antisense oligonucleotides targeting MALAT-1 compared to that of the control oligonucleotide group.

TABLE 5

Tumor polyps load in ApcMin mice

|  | Polpys/animal |
|---|---|
| ISIS 399479 | 1.6 |
| ISIS 141923 | 4.5 |
| PBS | 5.8 |

Example 3

Effect of Antisense Inhibition of MALAT-1 in a DEN-Induced Hepatocellular Carcinoma Mouse Model Diethyl nitrosamine (DEN) is a standard chemical carcinogen for inducing hepatocellular carcinoma (HCC) in rodents (Park, D. H. et al., Toxicol. Lett. 2009. 191: 321-6). The effect of inhibition of MALAT-1 RNA expression with antisense oligonucleotides on HCC development and progression was examined in this model.

Treatment

C57BL/6 male mice, 2 weeks in age, were given 25 mg/ml of DEN via intraperitoneal injection to induce HCC development. Five months after the DEN injection, the mice were randomly divided into three treatment groups. The first treatment group was given 50 mg/kg of ISIS 399479, administered subcutaneously twice a week for 16 weeks. The second treatment group was injected with 50 mg/kg of control oligonucleotide, ISIS 141923, administered subcutaneously twice a week for 16 weeks. The third group was injected with PBS, administered subcutaneously twice a week for 16 weeks. Mice were sacrificed on day 111 (first oligonucleotide treatment counted as day 1). DEN-induced HCCs on the liver surface were counted and collected and processed for further analysis.

RNA Analysis

RNA was isolated from each HCC using an RNA extraction kit from Qiagen. MALAT-1 RNA expression was measured by qPCR using primer probe set mMALAT1#2 and normalized to cyclophilin mRNA expression.

MALAT-1 RNA expression in mice treated with ISIS 399479 was significantly inhibited by 94% compared to the PBS-treated group.

Measurement of Tumor Load

The tumors of the surface of the liver in mice from all groups were counted at the end of experiment. As shown in Table 6, tumor number was significantly decreased in mice treated with antisense oligonucleotides targeting MALAT-1 compared to that of PBS group (p=0.017) or the control oligonucleotide group (p=0.02).

TABLE 6

Tumor number in the DEN-induced HCC mouse model

| Treatment groups | Tumors/mouse |
|---|---|
| ISIS 399479 | 1.9 |
| ISIS 141923 | 4.0 |
| PBS | 4.3 |

Example 4

Effect of Antisense Inhibition of MALAT-1 in a C26 Xenograft Mouse Model

The effect of inhibition of MALAT-1 RNA expression with antisense oligonucleotides on HCC progression was examined in murine C26 colon cancer xenograft model.

Treatment

C26 colon carcinoma cells were cultured in RPMI medium containing fetal bovine serum at a final concentration of 10%, and with 5% $CO_2$ at 37° C. Five million cells were subcutaneously implanted in male CD2F1 mice.

Four days after tumor implantation, the mice were randomly divided into three treatment groups. The first treatment group was injected with 50 mg/kg of ISIS 399462 (SEQ ID NO: 14), administered subcutaneously 5 days per week for 3 weeks. The second treatment group was injected with 50 mg/kg of ISIS 395251 (SEQ ID NO: 13), administered subcutaneously 5 days per week for 3 weeks. The third treatment group was injected with 50 mg/kg of control oligonucleotide, ISIS 347526 (TCTTATGTTTCCGAACCGTT; 5-10-5 MOE gapmer with no known murine or human target) (SEQ ID NO: 23) administered subcutaneously 5 days per week for 3 weeks. Mice were sacrificed on day 26. Liver and tumor tissue were collected and processed for further analysis. The data presented is the average of 2 independent experiments with similar results.

RNA Analysis

RNA extraction and analyses was performed using an RNA extraction kit from Qiagen. MALAT-1 RNA expression was measured using primer probe set mMALAT1 (forward sequence GTAGGTTAAGTTGACGGCCGTTA, designated herein as SEQ ID NO: 24; reverse sequence ATCTTCCCTGTTTCCAACTCATG, designated herein as SEQ ID NO: 25; probe sequence AAAAATCCTTCGACTGGCGCATGTACG, designated herein as SEQ ID NO: 26) and normalized to Cyclophilin mRNA expression.

MALAT-1 RNA expression was assessed in the liver. As shown in Table 7, MALAT-1 RNA expression in mice treated with either ISIS 395251 or ISIS 399462 was inhibited compared to the control oligonucleotide-treated group. The mRNA expression levels are expressed as percent inhibition of expression levels compared to that in the control group (normalized to 0%).

TABLE 7

Percent inhibition of MALAT-1 RNA levels (%) compared to the PBS control

|  | % inhibition |
|---|---|
| ISIS 395251 | 57 |
| ISIS 399462 | 71 |

Measurement of Tumor Weight and Volume

Tumor volumes were measured on a regular basis throughout the study period, using Vernier calipers. As shown in Table 8, tumor volumes were significantly decreased in mice treated with ISIS 395251 or ISIS 399462.

The weight of the tumor in each mouse from all groups was also assessed on day 26. As shown in Table 9, tumor weight was decreased in mice treated with antisense oligonucleotides targeting MALAT-1 compared to that of the control oligonucleotide group. These results demonstrate that antisense oligonucleotides targeting MALAT-1 reduced colon cancer growth.

TABLE 8

Tumor volume ($mm^3$) in the C26 xenograft model

| ISIS No | day 8 | day 11 | day 14 | day 19 | day 22 | day 25 |
|---|---|---|---|---|---|---|
| 399462 | 406 | 615 | 960 | 1365 | 1802 | 2275 |
| 395251 | 341 | 501 | 877 | 1480 | 1635 | 1641 |
| 347526 | 408 | 803 | 1493 | 2437 | 2647 | 3405 |

TABLE 9

Tumor weight in the C26 xenograft model

| ISIS No | Weight (g) |
|---|---|
| 395251 | 1.6 |
| 399462 | 1.7 |
| 347526 | 2.6 |

Example 5

Effect of Antisense Inhibition of MALAT-1 in a Hep3B Liver Orthotopic Mouse Model An orthotopic xenograft tumor model of hepatocellular carcinoma created by injection of Hep3B cells directly into the liver parenchyma of nude mice is a standard model for studying HCC (Yao, X. et al., Clin. Cancer Res. 2003. 9: 2719). The effect of inhibition of MALAT-1 RNA expression with antisense oligonucleotides on animal survival was examined in the Hep3B liver orthotopic model.

Treatment

The human HCC cell line Hep3B was purchased from ATCC. Hep3B cells were maintained in MEM media containing fetal bovine serum at a final concentration of 10%, and with 5% $CO_2$ at 37° C. Exponentially growing Hep3B cells were collected by trypsin-EDTA (Gibco-BRL) treatment and washed once with PBS. The cell pellet was suspended in PBS and kept in ice before intrahepatic injection in mice.

Female BALB/c athymic (nu/nu) nude mice, 4-6 weeks in age, were anesthetized with isoflurane. A small transverse incision below the sternum was made to expose the liver. A PBS suspension of $2 \times 10^6$ Hep3B cells was slowly injected into the upper left lobe of the liver using a 28-gauge needle. The cells were injected at a 30-degree angle into the liver. After injection, a small piece of sterile gauze was placed on the injection site, and light pressure was applied for 1 min to prevent bleeding. The abdomen was then closed with a 6-0 silk suture. The mice were allowed to recover in a warm cage.

After 10 days, the expression level of alpha-fetoprotein (AFP), which used as a positive marker of tumor growth in the mice, was analyzed. Those mice that tested positive for the marker were then randomly divided into two treatment groups. The first treatment group was injected with 50 mg/kg of ISIS 395251 (SEQ ID NO: 13), administered intraperitoneally 2 days per week for 7 weeks. The second treatment group was injected with 50 mg/kg of control oligonucleotide, ISIS 347526 (SEQ ID NO: 23) administered intraperitonally 2 days per week for 7 weeks.

Median Survival

Each group was monitored and deaths were recorded. At the end of the study, the median survival of each group was calculated using the statistical formula of Kaplan-Meier and the data is presented in Table 10. As shown in Table 10, the median survival was significantly increased in mice treated with ISIS 395251 compared to the control group. These data demonstrate that antisense oligonucleotides targeting MALAT-1 increased survival of animals having cancer.

TABLE 10

Median survival in the Hep3B liver orthotopic model

| ISIS No | days |
|---|---|
| 395251 | 88 |
| 347526 | 49 |

Example 6

Effect of Antisense Inhibition of MALAT-1 in a Metastatic EBC-1 Xenograft Mouse Model The effect of inhibition of MALAT-1 RNA expression with antisense oligonucleotides on metastasis was examined in EBC-1 lung cancer xenograft mouse model.

Treatment

The human cell line EBC-1 was purchased from the Health Sciences Foundation, Japan. EBC-1 cells were maintained in RPMI media containing fetal bovine serum at a final concentration of 10%, and with 5% $CO_2$ at 37° C. Exponentially growing EBC-1 cells were collected by trypsin-EDTA (Gibco-BRL) and washed once with PBS. The cell pellet was suspended in PBS and one million cells were implanted by subcutaneous injection into BALB/c nude mice.

Two weeks after implantation of the EBC-1 human tumor, the mice were randomly divided into two treatment groups. The first treatment group was injected with 50 mg/kg 5 days a week of ISIS 395251 (SEQ ID NO: 13), administered subcutaneously for 5 weeks. The second treatment group was injected with 50 mg/kg 5 days a week of control oligonucleotide, ISIS 347526 (SEQ ID NO: 23) administered subcutaneously for 5 weeks. On week 7, the subcutaneous tumor was surgically removed and the wound closed with a 4-0 suture. Mice were euthanized on week 12 after the start of antisense oligonucleotide treatment. Lung tissue was collected and processed for further analysis. The data presented is the average of 3 independent experiments with similar results.

Measurement of Primary Tumor Volume and Lung Tumor Multiplicity

Primary tumor volumes were measured along the course of the study period, using Vernier calipers. As shown in Table 11, at week 7 right before removal of the xenograft, tumor volumes were significantly decreased in mice treated with ISIS 395251 compared to the control group (p=0.00006).

The tumor multiplicity was also counted using a light microscope. As shown in Table 12, the tumor multiplicity was decreased in mice treated with ISIS 395251 compared to the control. These data demonstrate that antisense oligonucleotides targeting MALAT-1 inhibited metastasis.

TABLE 11

Tumor volume in the EBC-1 xenograft model

| ISIS No | Volume ($mm^3$) |
|---|---|
| 395251 | 1755 |
| 347526 | 2838 |

TABLE 12

Tumor multiplicity in the EBC-1 xenograft model

| ISIS No | Tumor count |
|---|---|
| 395251 | 68 |
| 347526 | 167 |

Example 7

Effect of Antisense Inhibition of MALAT-1 in the TRAMP Mouse Model

The transgenic adenocarcinoma of the mouse prostate (TRAMP) model closely mirrors the pathogenesis of human prostate cancer (Hurwitz, A. A. et al., Curr. Protoc. Immunol. 2001. Chapter 20: Unit 20.5). The effect of inhibition of MALAT-1 RNA expression with antisense oligonucleotides on tumor progression was examined in TRAMP mice.

Treatment

TRAMP mice, 23 weeks old, were randomly divided into two treatment groups. The first treatment group was injected with 50 mg/kg of ISIS 395251 (SEQ ID NO: 13), administered subcutaneously 5 days per week for 3 weeks. The second treatment group was injected with PBS administered subcutaneously 5 days per week for 3 weeks. Mice were sacrificed at the end of 26 weeks. Prostate tissue were collected and processed for further analysis.

RNA Analysis

RNA extraction was performed using an RNA extraction kit from Qiagen. MALAT-1 RNA expression was measured using primer probe set mMALAT1 and normalized to Cyclophilin mRNA expression.

MALAT-1 RNA expression was assessed in the tumor. MALAT-1 RNA expression in mice treated with ISIS 395251 was inhibited by 80% compared to the control group.

Measurement of Tumor Weight

Tumor tissue was excised from the prostate. Tumor weights were measured on a regular basis throughout the study period, using Vernier calipers. As shown in Table 13, tumor weight was decreased in mice treated with ISIS 395251 compared to the control group.

TABLE 13

Tumor weight in the TRAMP

| | Weight (g) |
|---|---|
| ISIS 395251 | 1.0 |
| PBS | 9.3 |

Example 8

Effect of Antisense Inhibition of MALAT-1 in a Patient-Derived Non-Small Cell Lung Cancer Xenograft Mouse Model Biopsy of tumor mass was done in a non-small cell lung cancer patient (at the University of California, Davis) and this was directly implanted into male NOD.Cg-Prkdc$^{scid}$Il2rg$^{tm1Wjl}$ISzJ (NSG; Jackson Laboratories) mice. After 2 in vivo passages, the tumor cells from the xenograft were banked at Jackson Laboratories (designated herein as LG-476 P2). The effect of inhibition of MALAT-1 RNA expression with antisense oligonucleotides on tumor progression of this tumor in mice was examined.

Treatment

Two NSG mice were implanted with the LG-476 P2 tumor and monitored three times weekly. Once the tumors reached 1,000 mm$^3$ in volume, the tumors were harvested and fragmented into 3-5 mm$^3$ size. Each fragment was then implanted subcutaneously into the right hind flank of 30 NSG mice. The mice were observed three times a week and once the tumors reached 200-250 mm$^3$ in size, the mice were randomly divided into two treatment groups. The first treatment group was injected with 50 mg/kg of ISIS 395251 (SEQ ID NO: 13), administered subcutaneously 5 days per week for 3 weeks. The second treatment group was injected with PBS administered subcutaneously 5 days per week for 3 weeks. Mice were euthanized by $CO_2$ inhalation 24 hrs after the last dose. Tumor tissue were collected and processed for further analysis.

RNA Analysis

RNA extraction was performed using an RNA extraction kit from Qiagen. MALAT-1 RNA expression was measured using primer probe set RTS2736 and normalized to Cyclophilin mRNA expression.

MALAT-1 RNA expression was assessed in the tumor. MALAT-1 RNA expression in mice treated with ISIS 395251 was inhibited by 76% compared to the control group.

Measurement of Tumor Volume

Tumor volumes were measured on a regular basis throughout the study period, using Vernier calipers. As shown in Table 14, tumor volumes were decreased in mice treated with ISIS 395251 compared to the control group.

TABLE 14

Tumor volume (mm$^3$) on different days in the small cell lung cancer xenograft model

| | Day 1 | Day 3 | Day 6 | Day 8 | Day 10 | Day 13 | Day 15 | Day 17 | Day 20 |
|---|---|---|---|---|---|---|---|---|---|
| ISIS 395251 | 227 | 376 | 391 | 448 | 529 | 681 | 661 | 747 | 715 |
| PBS | 225 | 314 | 384 | 494 | 568 | 696 | 917 | 1047 | 2049 |

Example 9

Effect of Antisense Inhibition of MALAT-1 in a Colo201 Xenograft Mouse Model

The effect of inhibition of MALAT-1 RNA expression with antisense oligonucleotides on tumor progression was examined in the Colo201 xenograft mouse model.

Treatment

The human colorectal adenocarcinoma cell line Colo201 was purchased from ATCC. Colo201 cells were maintained in RPMI media containing fetal bovine serum at a final concentration of 10%, and with 5% $CO_2$ at 37° C. Exponentially growing Colo201 cells were collected by trypsin-EDTA (Gibco-BRL) and washed once with PBS. The cell pellet was suspended in PBS and kept in ice before intrahepatic injection in female BALB/c nude mice.

Four days after tumor implantation, the mice were randomly divided into three treatment groups. The first treatment group was injected with 50 mg/kg of ISIS 395251 (SEQ ID NO: 13), administered subcutaneously 5 days per week for 3.5 weeks. The second treatment group was injected with 50 mg/kg of ISIS 347526 (SEQ ID NO: 23), administered subcutaneously 5 days per week for 3.5 weeks. The third group was injected with PBS administered subcutaneously 5 days per week for 3.5 weeks. Mice were sacrificed on day 29. Tumor tissue were collected and processed for further analysis.

RNA Analysis

RNA extraction was performed using an RNA extraction kit from Qiagen. MALAT-1 RNA expression was measured using primer probe set RTS2736 and normalized to Cyclophilin mRNA expression.

MALAT-1 RNA expression was assessed in the liver. MALAT-1 RNA expression in mice treated with ISIS 395251 was inhibited by 39% compared to the control group.

Measurement of Tumor Volume

Tumor volumes were measured on a regular basis throughout the study period, using Vernier calipers. As shown in Table 15, tumor volumes were decreased in mice treated with ISIS 395251 compared to the control group.

TABLE 15

Tumor volume on different days in the Colo201 cancer xenograft model

|  | Day 4 | Day 7 | Day 10 | Day 15 | Day 18 | Day 21 | Day 24 | Day 29 |
| --- | --- | --- | --- | --- | --- | --- | --- | --- |
| ISIS 395251 | 138 | 132 | 186 | 207 | 241 | 247 | 288 | 341 |
| ISIS 347526 | 148 | 156 | 209 | 238 | 354 | 439 | 428 | 476 |
| PBS | 159 | 142 | 184 | 240 | 373 | 393 | 404 | 495 |

What is claimed is:

1. A method of treating a primary cancer in an animal comprising administering to the animal a therapeutically effective amount of a single-stranded modified oligonucleotide 12 to 30 linked nucleosides in length having a nucleobase sequence at least 85% complementary to a Metastasis-Associated-in-Lung-Adenocarcinoma-Transcript-1 (MALAT-1) nucleic acid, thereby treating the primary cancer in the animal.

2. The method of claim 1, wherein administering the modified oligonucleotide reduces expression of MALAT-1.

3. The method of claim 2, wherein expression of MALAT-1 RNA is reduced.

4. The method of claim 1, wherein the animal is a human.

5. The method of claim 1, wherein the MALAT-1 nucleic acid is a human MALAT-1 nucleic acid.

6. The method of claim 5, wherein the human MALAT-1 nucleic acid has a nucleotide sequence of SEQ ID NO: 1.

7. The method of claim 1, wherein the modified oligonucleotide has a nucleobase sequence 100% complementary to a human MALAT-1 nucleic acid.

8. The method of claim 1, wherein administering the therapeutically effective amount of the modified oligonucleotide inhibits cancer growth.

9. The method of claim 1, wherein administering the therapeutically effective amount of the modified oligonucleotide increases survival of the animal.

10. The method of claim 1, wherein the therapeutically effective amount of the modified oligonucleotide is administered to an animal identified as having primary cancer.

11. The method of claim 1, wherein the cancer is colon cancer, lung cancer, liver cancer, prostate cancer, or intestinal cancer.

12. The method of claim 1, wherein the modified oligonucleotide comprises at least one modified internucleoside linkage.

13. The method of claim 12, wherein the modified internucleoside linkage is a phosphorothioate internucleoside linkage.

14. The method of claim 1, wherein at least one nucleoside of the modified oligonucleotide comprises a modified sugar.

15. The method of claim 14, wherein the modified sugar is a bicyclic sugar.

16. The method of claim 15, wherein the bicyclic sugar comprises a 4'-CH(CH$_3$)—O-2', 4'-(CH$_2$)—O-2', or 4'-(CH$_2$)$_2$—O-2' bridge.

17. The method of claim 14, wherein the modified sugar comprises a 2'-O-methoxyethyl group.

18. The method of claim 1, wherein at least one nucleoside of the modified oligonucleotide comprises a modified nucleobase.

19. The method of claim 18, wherein the modified nucleobase is a 5-methylcytosine.

20. The method of claim 1, wherein the modified oligonucleotide comprises:
- a gap segment consisting of linked deoxynucleosides;
- a 5' wing segment consisting of linked nucleosides; and
- a 3' wing segment consisting of linked nucleosides, wherein the gap segment is positioned immediately adjacent to and between the 5' wing segment and the 3' wing segment and wherein each nucleoside of each wing segment comprises a modified sugar.

* * * * *